US006503734B1

(12) United States Patent
Craft et al.

(10) Patent No.: US 6,503,734 B1
(45) Date of Patent: Jan. 7, 2003

(54) **CYTOCHROME B5 GENE AND PROTEIN OF *CANDIDA TROPICALIS* AND METHODS RELATING THERETO**

(75) Inventors: David L. Craft, Fort Thomas, KY (US); Krishna M. Madduri, Westfield, IN (US); John C. Loper, Cincinnati, OH (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/912,161

(22) Filed: Jul. 24, 2001

Related U.S. Application Data

(60) Provisional application No. 60/220,958, filed on Jul. 26, 2000.

(51) Int. Cl.$^7$ ........................ C12D 21/02; C07H 21/04; C12N 1/15; C12N 1/19; C12N 15/00

(52) U.S. Cl. ................ 435/69.1; 536/23.2; 435/254.11; 435/255.4; 435/320.1

(58) Field of Search .................... 536/23.2; 435/254.11, 435/255.1, 255.2, 255.4, 255.5, 320.1, 71.1, 171, 69.1, 189

(56) References Cited

FOREIGN PATENT DOCUMENTS

WO 0065061 11/2000
WO WO 00/65061 * 11/2000

OTHER PUBLICATIONS

Kobayashi et al., Genetics analysis of cytochrome b5 from arachidonic acid–producing fungus, Mortierella alpina 1S–4: Cloning, RNA editing and expression . . . , 1999, J. Biochem., vol. 125, pp. 1094–1103.*

Bertrand, J.C. et al., (1982) "Isolation and characterization of cytochrome b5 from *Candida tropicalis* grown on alkane", *Biochimie*, 64:1041–1048.

Truan, Gilles et al., (1994) "Cloning and characterization of a yeast cytochrome b5–encoding gene which suppresses ketoconazole hypersensitivity in a NADPH–P–450 reductase–deficient strain", *Gene*, 149:123–127.

* cited by examiner

*Primary Examiner*—James Ketter
*Assistant Examiner*—Daniel Sullivan
(74) *Attorney, Agent, or Firm*—John E. Drach

(57) ABSTRACT

A novel gene has been isolated which encodes cytochrome b5 (CYTb5) protein of the ω-hydroxylase complex of *C. tropicalis* 20336. Vectors including this gene, and transformed host cells are provided. Methods of increasing the production of a CYTb5 protein are also provided which involve transforming a host cell with a gene encoding this protein and culturing the cells. Methods of increasing the production of a dicarboxylic acid are also provided which involve increasing in the host cell the number of genes encoding this protein.

22 Claims, 56 Drawing Sheets

```
        10         20         30         40         50         60
ACATACTTCA AGCAGTTTGG CGACATAGTG AACCTCAAGT TATCACGGAA CAAGACGACG

        70         80         90        100        110        120
GGCAAGAGCA AGCACTACGG GTTTATAGAG TTCACGTCGC CTGAAGTTGC CCAGATCGCG

       130        140        150        160        170        180
GCGGAGACGA TGAACAACTA CTTGTTGTTT GGACACTTGA TCAAATGTGA GGTTGTCAGC

       190        200        210        220        230        240
GAGCCGTTCA AGGACTTGTT CAAGGACTCG AAGAGGAAGT TCAAGGTGAT TCCCTGGAAG

       250        260        270        280        290        300
AAGATCGCGA AGGATAAGCA CGATAAGCCA AAGTCCGCGA AGGAGTGGGC GAAGTTGGTG

       310        320        330        340        350        360
GAGAAGTTCG AAGAGTCCAA GAAGAAGAAG CAGGAGGAGT TGAAGAGTAA AGGTATTGAT

       370        380        390        400        410        420
TTTGATTTGG CTGCTATATA AAGGAGATAA GAGAGGAGGA TGACAAGCGC AAACGAGCAT

       430        440        450        460        470        480
TCTGTTGATG TGTAAAGCAG GTATAGATAA TAGCGGATAA CGTAAAATAA GAGATCTCCA

       490        500        510        520        530        540
ACTTCCAACT TCCAACTTCC GACCCTCATC TTTTGGGGGA GAGGGATTGG TATGTAGTGG

       550        560        570        580        590        600
TGAGGGAGAG GAGGATATTT TGTTTTGCCT AATTGGGATA AATTATCCCA GTCAGTTGAA

       610        620        630        640        650        660
AGAGCGAGGC GTAAGCCATT TCTTTTTCTA ACTGCAAATA GCATACAGAT GCGATAGTTA

       670        680        690        700        710        720
ACGAAGAGAG AAATCAAGAG CAGGTGACTA CATACATAGA TAGTGACATT ATAATAACAT

       730        740        750        760        770        780
GGCGCATCAT TGGTTCTATG TAGCTGGCAG GGTTATTATC AAGCTTGAAT AGTTTAATAA

       790        800        810        820        830        840
AAATCGTACC ATGAATGTAT GCATAGAAGC AATAAGGAAG CCTGTGCCTG TGAGTAGTAG

       850        860        870        880        890        900
CAGTAGCGGG GGGAGACGCT AGTTTAGGGG TAAAATGTCA GCACATGAAC AGCAGTTGAA

       910        920        930        940        950        960
GTGGGTGCCA ATCAAGTAAG AACATCTTGT GAAAAATCAA AAGCAATGGT ATATGTGTTC

       970        980        990       1000       1010       1020
CTGCATACAG TGCTGGAGTC AACGAGCCAA AAAAAAAAAA GAAAGAAAGA GAGAAAAACT

      1030       1040       1050       1060       1070       1080
TATCGTATAA AAACCACACA AAAATTTCCC AATCCCAATT CCTTCATTCT TCTTCTTTTA

      1090       1100       1110          1120           1130
CTGATTTAAC CCACAGATAC ATACAATT ATG ACC GAC ACA GAC ACC ACG ACC ACC
                               M   T   D   T   D   T   T   T   T>

1140         1150          1160          1170          1180
ATC TAC ACC CAC GAA GAG GTT GCC CAG CAC ACC ACC CAC GAC GAC TTG
I   Y   T   H   E   E   V   A   Q   H   T   T   H   D   D   L>
```

FIG. 1A 1190 1200 1210 1220 1230  
TGG GTT ATT CTC AAT GGT AAG GTC TAC AAC ATC TCC AAC TAT ATA GAC  
W V I L N G K V Y N I S N Y I D>

1240 1250 1260 1270  
GAG CAC CCA GGT GGT GAA GAA GTC ATT CTT GAT TGC GCC GGC ACA GAC  
E H P G G E E V I L D C A G T D>

1280 1290 1300 1310 1320  
GCC ACT GAA GCC TTT GAC GAC ATT GGC CAC TCC GAC GAG GCC CAC GAG  
A T E A F D D I G H S D E A H E>

1330 1340 1350 1360 1370  
ATC TTG GAA AAG TTG TAC ATT GGT AAC TTG AAG GGC GCT AAG ATT GTT  
I L E K L Y I G N L K G A K I V>

1380 1390 1400 1410 1420  
GAG GCC AAG CAC GCG CAG TCG TTC AGC ACG GAA GAA GAC TCG GGT ATC  
E A K H A Q S F S T E E D S G I>

1430 1440 1450 1460 1470  
AAC TTC CCA TTG ATT GCT GTT GGT GTG TTT TTG GCT GCT TTC GGT GTC  
N F P L I A V G V F L A A F G V>

1480 1490 1500 1510 1520  
TAC TAC TAC AAG ACC AAC TTT GCC TAAGC ATAACAAGCA GTACAGTTGA  
Y Y Y K T N F A>

1530 1540 1550 1560 1570 1580  
AGGACAGGGT AGAGGAGATG AGAAAAAACG GGAACCCAAC AAAGATTATT TTCACACATC 1590 1600 1610 1620 1630 1640  
ACATGGAGGG GCTGATCCCA CTTTTTGACG TCAATATCCA CAGCACGAAG AAAGAAAGAA 1650 1660 1670 1680 1690 1700  
AGAAAGAAAG TCTATGGAAG AGGAAATGGA TCACATTAGA GCTTTTCTTT ATGTAACATA 1710 1720 1730 1740 1750 1760  
TATATATATA TAAACTAATA CAGATTTACA GATACACCAC ATCACCGCAG GGCTTATCAT 1770 1780 1790 1800 1810 1820  
CTGATGGTGC CCAAAAAAAA AAATCCACTG TGGATGAGCC TAGTTAGGAG ATATCGGAGT 1830 1840 1850 1860 1870 1880  
AGCTCATTCT TTTGATATCT AGGTCTTCCT CTCTTGGATT CTACGTTGGT ACTTGGTGCT 1890 1900 1910 1920 1930 1940  
ACACGATGAG ATCACCAGGT GTCATTCTGG AGTTTGGTGG AAAGTGTGTT GATTTTTTTA 1950 1960 1970 1980 1990 2000  
GTAAGCAAGA ATTTGTTGAG TTCTATTGGA TGTTCTGGTG CGGCCACTTC CATCCCCCCA 2010 2020 2030 2040 2050 2060  
CCCCTTGTCT TGTCTTGTCT TGTCTTATTT TTTTGGGTCG GTTGGCGGAA GTAAGACGCA 2070 2080 2090 2100 2110 2120  
CGCACAGGAG GAGCACGACG GATAAATATC CACTTTTTTC ACACGCGTCG ATTGACGGCT 2130 2140 2150 2160 2170 2180  
TGTGTGAATT GTGGGGAATA CGGATAAGGG GGTATACCAC ACACACACAT ATCTAACATA 2190 2200 2210 2220 2230 2240  
TCAGACCACT TTCTATAACA GATCTCATGA TCCCCTTGAG AGTTGATGCA AGTCTATGCT

FIG. 1B

| 2250 | 2260 | 2270 | 2280 | 2290 | 2300 |
|---|---|---|---|---|---|
| CCTGTGATAT | TGCCCCCCCC | CCCCCAAGGA | AGGGCGGGGC | ATGTTATCAG | GGACCTGGAT |
| 2310 | 2320 | 2330 | 2340 | 2350 | 2360 |
| GAACCCTTGA | TGGCGGTGTG | AGTAGATGCA | AGAGAGGTTG | TGCTTTGGAA | GTAGCTGAAG |
| 2370 | 2380 | 2390 | 2400 | 2410 | 2420 |
| GTGTAGGGAC | ATCCGGTACT | ATAGTTCTCT | TGAAGGATCA | TGCCAGCTCC | CTTTCTGTGG |
| 2430 | 2440 | 2450 | 2460 | 2470 | 2480 |
| CTCTCTGGAA | GCTCTGCATC | TTCTCTTCGT | TGAAACAGCG | TGGAGTTACG | AAAGGTACCC |
| 2490 | 2500 | 2510 | 2520 | 2530 | 2540 |
| TGTGGTGAGT | TCAAACAAGA | CATGGCTCTA | CAAGCTGTCG | AGGATAAAAG | TAATTAAACA |
| 2550 | 2560 | 2570 | 2580 | 2590 | 2600 |
| ACATGTATAT | ATATTAATAA | ACGGATCCGT | GGTGCTAGAT | TGTGGTAGAT | GTTTAGTATC |
| 2610 | 2620 | 2630 | 2640 | 2650 | 2660 |
| GTTTATCACC | TCTAGTGAAA | ACTAGCATTT | GATTCCATTA | GTCATCAGTA | CTTGATGTTA |
| 2670 | 2680 | 2690 | 2700 | 2710 | |
| CATTCAACCA | AATGAAGGTC | GGTCCAAGAT | CCAAAGAATT | CAAAAAGCTT | |

FIG. 1C

```
catcaagatc atctatgggg ataattacga cagcaacatt gcagaaagag cgttggtcac 60
aatcgaaaga gcctatggcg ttgccgtcgt tgaggcaaat gacagcacca acaataacga 120
tggtcccagt gaagagcctt cagaacagtc cattgttgac gcttaaggca cggataatta 180
cgtggggcaa aggaacgcgg aattagttat gggggatca aaagcggaag atttgtgttg 240
cttgtgggtt ttttccttta tttttcatat gatttctttg cgcaagtaac atgtgccaat 300
ttagtttgtg attagcgtgc cccacaattg gcatcgtgga cgggcgtgtt ttgtcatacc 360
ccaagtctta actagctcca cagtctcgac ggtgtctcga cgatgtcttc ttccacccct 420
cccatgaatc attcaaagtt gttgggggat ctccaccaag ggcaccggag ttaatgctta 480
tgtttctccc actttggttg tgattggggt agtctagtga gttggagatt ttcttttttt 540
cgcaggtgtc tccgatatcg aaatttgatg aatatagaga gaagccagat cagcacagta 600
gattgccttt gtagttagag atgttgaaca gcaactagtt gaattacacg ccaccacttg 660
acagcaagtg cagtgagctg taaacgatgc agccagagtg tcaccaccaa ctgacgttgg 720
gtggagttgt tgttgttgtt gttggcaggg ccatattgct aaacgaagac aagtagcaca 780
aaacccaagc ttaagaacaa aaataaaaaa aattcatacg acaattccaa agccattgat 840
ttacataatc aacagtaaga cagaaaaaac tttcaacatt tcaaagttcc ctttttccta 900
ttacttcttt tttttcttct ttccttcttt ccttctgttt ttcttacttt atcagtcttt 960
tacttgtttt tgcaattcct catcctcctc ctactcctcc tcaccatggc tttagacaag 1020
ttagatttgt atgtcatcat aacattggtg gtcgctgtag ccgcctattt tgctaagaac 1080
cagttccttg atcagcccca ggacaccggg ttcctcaaca cggacagcgg aagcaactcc 1140
agagacgtct tgctgacatt gaagaagaat aataaaaaca cgttgttgtt gtttgggtcc 1200
cagacgggta cggcagaaga ttacgccaac aaattgtcca gagaattgca ctccagattt 1260
ggcttgaaaa cgatggttgc agatttcgct gattacgatt gggataactt cggagatatc 1320
accgaagaca tcttggtgtt tttcattgtt gccacctatg gtgagggtga acctaccgat 1380
aatgccgacg agttccacac ctggttgact gaagaagctg acactttgag taccttgaaa 1440
tacaccgtgt tcgggttggg taactccacg tacgagttct tcaatgccat tggtagaaag 1500
tttgacagat tgttgagcga gaaaggtggt gacaggtttg ctgaatacgc tgaaggtgat 1560
gacggtactg gcaccttgga cgaagatttc atggcctgga aggacaatgt ctttgacgcc 1620
ttgaagaatg atttgaactt tgaagaaaag gaattgaagt acgaaccaaa cgtgaaattg 1680
actgagagag acgacttgtc tgctgctgac tcccaagttt ccttgggtga gccaaacaag 1740
aagtacatca actccgaggg catcgacttg accaagggtc cattcgacca cacccaccca 1800
tacttggcca gaatcaccga gacgagagag ttgttcagct ccaaggacag acactgtatc 1860
cacgttgaat ttgacatttc tgaatcgaac ttgaaataca ccaccggtga ccatctagct 1920
atctggccat ccaactccga cgaaaacatt aagcaatttg ccaagtgttt cggattggaa 1980
gataaactcg acactgttat tgaattgaag gcgttggact ccacttacac catcccattc 2040
ccaaccccaa ttacctacgg tgctgtcatt agacaccatt tagaaatctc cggtccagtc 2100
tcgagacaat tctttttgtc aattgctggg tttgctcctg atgaagaaac aaagaaggct 2160
tttaccagac ttggtggtga caagcaagaa ttcgccgcca aggtcacccg cagaaagttc 2220
aacattgccg atgccttgtt atattcctcc aacaacgctc catggtccga tgttcctttt 2280
gaattcctta ttgaaaacgt tccacacttg actccacgtt actactccat ttcgtcttcg 2340
tcattgagtg aaaagcaact catcaacgtt actgcagttg ttgaagccga agaagaagct 2400
gatggcagac cagtcactgg tgttgtcacc aacttgttga agaacgttga aattgtgcaa 2460
aacaagactg gcgaaaagcc acttgtccac tacgatttga gcggcccaag aggcaagttc 2520
aacaagttca agttgccagt gcatgtgaga agatccaact ttaagttgcc aaagaactcc 2580
accaccccag ttatcttgat tggtccaggt actggtgttg ccccattgag aggttttgtc 2640
agagaaagag ttcaacaagt caagaatggt gtcaatgttg gcaagacttt gttgttttat 2700
ggttgcagaa actccaacga ggactttttg tacaagcaag aatgggccga gtacgcttct 2760
gttttgggtg aaaactttga gatgttcaat gccttctcca gacaagaccc atccaagaag 2820
gtttacgtcc aggataagat tttagaaaac agccaacttg tgcacgagtt gttgactgaa 2880
ggtgccatta tctacgtctg tggtgatgcc agtagaatgg ctagagacgt gcagaccaca 2940
atttccaaga ttgttgctaa aagcagagaa attagtgaag acaaggctgc tgaattggtc 3000
aagtcctgga aggtccaaaa tagataccaa gaagatgttt ggtagactca aacgaatctc 3060
```

FIG. 2A

```
tctttctccc aacgcattta tgaatcttta ttctcattga agctttacat atgttctaca 3120
ctttattttt tttttttttt ttattattat attacgaaac ataggtcaac tatatatact 3180
tgattaaatg ttatagaaac aataactatt atctactcgt ctacttcttt ggcattgaca 3240
tcaacattac cgttcccatt accgttgccg ttggcaatgc cgggatattt agtacagtat 3300
ctccaatccg gatttgagct attgtagatc agctgcaagt cattctccac cttcaaccag 3360
tacttatact tcatctttga cttcaagtcc aagtcataaa tattacaagt tagcaagaac 3420
ttctggccat ccacgatata gacgttattc acgttattat gcgacgtatg gatgtggtta 3480
tccttattga acttctcaaa cttcaaaaac aaccccacgt cccgcaacgt cattatcaac 3540
gacaagttct ggctcacgtc gtcggagctc gtcaagttct caattagatc gttcttgtta 3600
ttgatcttct ggtactttct caattgctgg aacacattgt cctcgttgtt caaatagatc 3660
ttgaacaact ttttcaacgg gatcaacttc tcaatctggg ccaagatctc cgccgggatc 3720
ttcagaaaca agtcctgcaa cccctggtcg atggtctccg ggtacaacaa gtccaagggg 3780
cagaagtgtc taggcacgtg tttcaactgg ttcaacgaac atgttcgaca gtagttcgag 3840
ttatagttat cgtacaacca ttttggtttg atttcgaaaa tgacggagct gatgccatca 3900
ttctcctggt tcctctcata gtacaactgg cacttcttcg agaggctcaa ttcctcgtag 3960
ttcccgtcca agatattcgg caacaagagc ccgtaccgct cacggagcat caagtcgtgg 4020
ccctggttgt tcaacttgtt gatgaagtcc gaggtcaaga caatcaactg gatgtcgatg 4080
atctggtgcg ggaacaagtt cttgcatttt agctcgatga agtcgtacaa ctcacacgtc 4140
gagatatact cctgttcctc cttcaagagc cggatccgca agagcttgtg cttcaagtag 4200
tcgttg                                                            4206
```

FIG. 2B

```
Met Ala Leu Asp Lys Leu Asp Leu Tyr Val Ile Ile Thr Leu Val Val
 1               5                  10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu  X  Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Lys Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255
```

FIG. 3A

Lys Gly Pro Phe Asp His Thr His Pro Tyr Leu Ala Arg Ile Thr Glu
260 265 270

Thr Arg Glu Leu Phe Ser Ser Lys Asp Arg His Cys Ile His Val Glu
275 280 285

Phe Asp Ile Ser Glu Ser Asn Leu Lys Tyr Thr Thr Gly Asp His Leu
290 295 300

Ala Ile Trp Pro Ser Asn Ser Asp Glu Asn Ile Lys Gln Phe Ala Lys
305 310 315 320

Cys Phe Gly Leu Glu Asp Lys Leu Asp Thr Val Ile Glu Leu Lys Ala
325 330 335

Leu Asp Ser Thr Tyr Thr Ile Pro Phe Pro Thr Pro Ile Thr Tyr Gly
340 345 350

Ala Val Ile Arg His His Leu Glu Ile Ser Gly Pro Val Ser Arg Gln
355 360 365

Phe Phe Leu Ser Ile Ala Gly Phe Ala Pro Asp Glu Glu Thr Lys Lys
370 375 380

Ala Phe Thr Arg Leu Gly Gly Asp Lys Gln Glu Phe Ala Ala Lys Val
385 390 395 400

Thr Arg Arg Lys Phe Asn Ile Ala Asp Ala Leu Leu Tyr Ser Ser Asn
405 410 415

Asn Ala Pro Trp Ser Asp Val Pro Phe Glu Phe Leu Ile Glu Asn Val
420 425 430

Pro His Leu Thr Pro Arg Tyr Tyr Ser Ile Ser Ser Ser Ser Leu Ser
435 440 445

Glu Lys Gln Leu Ile Asn Val Thr Ala Val Val Glu Ala Glu Glu Glu
450 455 460

Ala Asp Gly Arg Pro Val Thr Gly Val Val Thr Asn Leu Leu Lys Asn
465 470 475 480

Val Glu Ile Val Gln Asn Lys Thr Gly Glu Lys Pro Leu Val His Tyr
485 490 495

Asp Leu Ser Gly Pro Arg Gly Lys Phe Asn Lys Phe Lys Leu Pro Val
500 505 510

His Val Arg Arg Ser Asn Phe Lys Leu Pro Lys Asn Ser Thr Thr Pro
515 520 525

FIG. 3B

Val Ile Leu Ile Gly Pro Gly Thr Gly Val Ala Pro Leu Arg Gly Phe
530 535 540

Val Arg Glu Arg Val Gln Gln Val Lys Asn Gly Val Asn Val Gly Lys
545 550 555 560

Thr Leu Leu Phe Tyr Gly Cys Arg Asn Ser Asn Glu Asp Phe Leu Tyr
565 570 575

Lys Gln Glu Trp Ala Glu Tyr Ala Ser Val Leu Gly Glu Asn Phe Glu
580 585 590

Met Phe Asn Ala Phe Ser Arg Gln Asp Pro Ser Lys Lys Val Tyr Val
595 600 605

Gln Asp Lys Ile Leu Glu Asn Ser Gln Leu Val His Glu Leu Leu Thr
610 615 620

Glu Gly Ala Ile Ile Tyr Val Cys Gly Asp Ala Ser Arg Met Ala Arg
625 630 635 640

Asp Val Gln Thr Thr Ile Ser Lys Ile Val Ala Lys Ser Arg Glu Ile
645 650 655

Ser Glu Asp Lys Ala Ala Glu Leu Val Lys Ser Trp Lys Val Gln Asn
660 665 670

Arg Tyr Gln Glu Asp Val Trp
675

FIG. 3C

```
tatatgatat atgatatatc ttcctgtgta attattattc gtattcgtta atacttacta 60
catttttttt tctttattta tgaagaaaag gagagttcgt aagttgagtt gagtagaata 120
ggctgttgtg catacgggga gcagaggaga gtatccgacg aggaggaact gggtgaaatt 180
tcatctatgc tgttgcgtcc tgtactgtac tgtaaatctt agatttccta gaggttgttc 240
tagcaaataa agtgtttcaa gatacaattt tacaggcaag ggtaaaggat caactgatta 300
gcggaagatt ggtgttgcct gtggggttct tttatttttc atatgatttc tttgcgcgag 360
taacatgtgc caatctagtt tatgattagc gtacctccac aattggcatc ttggacgggc 420
gtgttttgtc ttacccccaag ccttatttag ttccacagtc tcgacggtgt ctcgccgatg 480
tcttctccca cccctcgcag gaatcattcg aagttgttgg gggatctcct ccgcagttta 540
tgttcatgtc tttcccactt tggttgtgat tggggtagcg tagtgagttg gtgattttct 600
tttttcgcag gtgtctccga tatcgaagtt tgatgaatat aggagccaga tcagcatggt 660
atattgcctt tgtagataga gatgttgaac aacaactagc tgaattacac accaccgcta 720
aacgatgcgc acagggtgtc accgccaact gacgttgggt ggagttgttg ttggcagggc 780
catattgcta aacgaagaga agtagcacaa aacccaaggt taagaacaat taaaaaaatt 840
catacgacaa ttccacagcc atttacataa tcaacagcga caaatgagac agaaaaaact 900
ttcaacattt caaagttccc tttttcctat tacttctttt tttctttcct tcctttcatt 960
tcctttcctt ctgcttttat tactttacca gtcttttgct tgtttttgca attcctcatc 1020
ctcctcctca ccatggcttt agacaagtta gatttgtatg tcatcataac attggtggtc 1080
gctgtggccg cctattttgc taagaaccag ttccttgatc agccccagga caccgggttc 1140
ctcaacacgg acagcggaag caactccaga gacgtcttgc tgacattgaa gaagaataat 1200
aaaaacacgt tgttgttgtt tgggtcccag accggtacgg cagaagatta cgccaacaaa 1260
ttgtcaagag aattgcactc cagatttggc ttgaaaacca tggttgcaga tttcgctgat 1320
tacgattggg ataacttcgg agatatcacc gaagatatct tggtgttttt catcgttgcc 1380
acctacggtg agggtgaacc taccgacaat gccgacgagt tccacacctg gttgactgaa 1440
gaagctgaca ctttgagtac tttgagatat accgtgttcg ggttgggtaa ctccacctac 1500
gagttcttca atgctattgg tagaaagttt gacagattgt tgagtgagaa aggtggtgac 1560
agatttgctg aatatgctga aggtgacgac ggcactggca ccttggacga agatttcatg 1620
gcctggaagg ataatgtctt tgacgccttg aagaatgact tgaactttga agaaaaggaa 1680
ttgaagtacg aaccaaacgt gaaattgact gagagagatg acttgtctgc tgccgactcc 1740
caagtttcct tgggtgagcc aaacaagaag tacatcaact ccgagggcat cgacttgacc 1800
aagggtccat tcgaccacac ccacccatac ttggccagga tcaccgagac cagagagttg 1860
ttcagctcca aggaaagaca ctgtattcac gttgaatttg acatttctga atcgaacttg 1920
aaatacacca ccggtgacca tctagccatc tggccatcca actccgacga aaacatcaag 1980
caatttgcca agtgtttcgg attggaagat aaactcgaca ctgttattga attgaaggca 2040
ttggactcca cttacaccat tccattccca actccaatta cttacggtgc tgtcattaga 2100
caccatttag aaatctccgg tccagtctcg agacaattct tttgtcgat tgctgggttt 2160
gctcctgatg aagaaacaaa gaagactttc accagacttg gtggtgacaa acaagaattc 2220
gccaccaagg ttacccgcag aaagttcaac attgccgatg ccttgttata ttcctccaac 2280
aacactccat ggtccgatgt tcctttttgag ttccttattg aaaacatcca acacttgact 2340
ccacgttact actccatttc ttcttcgtcg ttgagtgaaa aacaactcat caatgttact 2400
gcagtcgttg aggccgaaga agaagccgat ggcagaccag tcactggtgt tgttaccaac 2460
ttgttgaaga acattgaaat tgcgcaaaac aagactggcg aaaagccact tgttcactac 2520
gatttgagcg gcccaagagg caagttcaac aagttcaagt tgccagtgca cgtgagaaga 2580
tccaacttta agttgccaaa gaactccacc accccagtta tcttgattgg tccaggtact 2640
ggtgttgccc cattgagagg tttcgttaga gaaagagttc aacaagtcaa gaatggtgtc 2700
aatgttggca agactttgtt gttttatggt tgcagaaact ccaacgagga ctttttgtac 2760
aagcaagaat gggccgagta cgcttctgtt ttgggtgaaa actttgagat gttcaatgcc 2820
ttctctagac aagacccatc caagaaggtt tacgtccagg ataagatttt agaaaacagc 2880
caacttgtgc acgaattgtt gaccgaaggt gccattatct acgtctgtgg tgacgccagt 2940
```

FIG. 4A

```
agaatggcca gagacgtcca gaccacgatc tccaagattg ttgccaaaag cagagaaatc 3000
agtgaagaca aggccgctga attggtcaag tcctggaaag tccaaaatag ataccaagaa 3060
gatgtttggt agactcaaac gaatctctct ttctcccaac gcatttatga atattctcat 3120
tgaagtttta catatgttct atatttcatt ttttttttat tatattacga aacataggtc 3180
aactatatat acttgattaa atgttataga aacaataatt attatctact cgtctacttc 3240
tttggcattg gcattggcat tggcattggc attgccgttg ccgttggtaa tgccgggata 3300
tttagtacag tatctccaat ccggatttga gctattgtaa atcagctgca agtcattctc 3360
caccttcaac cagtacttat acttcatctt tgacttcaag tccaagtcat aaatattaca 3420
agttagcaag aacttctggc catccacaat atagacgtta ttcacgttat tatgcgacgt 3480
atggatatgg ttatccttat tgaacttctc aaacttcaaa aacaacccca cgtcccgcaa 3540
cgtcattatc aacgacaagt tctgactcac gtcgtcggag ctcgtcaagt tctcaattag 3600
atcgttcttg ttattgatct tctggtactt tctcaactgc tggaacacat tgtcctcgtt 3660
gttcaaatag atcttgaaca acttcttcaa gggaatcaac ttttcgatct gggccaagat 3720
ttccgccggg atcttcagaa acaagtcctg caacccctgg tcgatggtct cggggtacaa 3780
caagtctaag gggcagaagt gtctaggcac gtgtttcaac tggttcaagg aacatgttcg 3840
acagtagttc gagttatagt tatcgtacaa ccactttggc ttgatttcga aaatgacgga 3900
gctgatccca tcattctcct ggttcctttc atagtacaac tggcatttct tcgagagact 3960
caactcctcg tagttcccgt ccaagatatt cggcaacaag agcccgtagc gctcacggag 4020
catcaagtcg tggccctggt tgttcaactt gttgatgaag tccgatgtca agacaatcaa 4080
ctggatgtcg atgatctggt gcggaaacaa gttcttgcac tttagctcga tgaagtcgta 4140
caact                                                             4145
```

FIG. 4B

Met Ala Leu Asp Lys Leu Asp Leu Tyr Val Ile Ile Thr Leu Val Val
1 5 10 15

Ala Val Ala Ala Tyr Phe Ala Lys Asn Gln Phe Leu Asp Gln Pro Gln
20 25 30

Asp Thr Gly Phe Leu Asn Thr Asp Ser Gly Ser Asn Ser Arg Asp Val
35 40 45

Leu X Thr Leu Lys Lys Asn Asn Lys Asn Thr Leu Leu Leu Phe Gly
50 55 60

Ser Gln Thr Gly Thr Ala Glu Asp Tyr Ala Asn Lys Leu Ser Arg Glu
65 70 75 80

Leu His Ser Arg Phe Gly Leu Lys Thr Met Val Ala Asp Phe Ala Asp
85 90 95

Tyr Asp Trp Asp Asn Phe Gly Asp Ile Thr Glu Asp Ile Leu Val Phe
100 105 110

Phe Ile Val Ala Thr Tyr Gly Glu Gly Glu Pro Thr Asp Asn Ala Asp
115 120 125

Glu Phe His Thr Trp Leu Thr Glu Glu Ala Asp Thr Leu Ser Thr Leu
130 135 140

Arg Tyr Thr Val Phe Gly Leu Gly Asn Ser Thr Tyr Glu Phe Phe Asn
145 150 155 160

Ala Ile Gly Arg Lys Phe Asp Arg Leu Leu Ser Glu Lys Gly Gly Asp
165 170 175

Arg Phe Ala Glu Tyr Ala Glu Gly Asp Asp Gly Thr Gly Thr Leu Asp
180 185 190

Glu Asp Phe Met Ala Trp Lys Asp Asn Val Phe Asp Ala Leu Lys Asn
195 200 205

Asp Leu Asn Phe Glu Glu Lys Glu Leu Lys Tyr Glu Pro Asn Val Lys
210 215 220

Leu Thr Glu Arg Asp Asp Leu Ser Ala Ala Asp Ser Gln Val Ser Leu
225 230 235 240

Gly Glu Pro Asn Lys Lys Tyr Ile Asn Ser Glu Gly Ile Asp Leu Thr
245 250 255

FIG. 5A

Lys Gly Pro Phe Asp His Thr His Pro Tyr Leu Ala Arg Ile Thr Glu
260 265 270

Thr Arg Glu Leu Phe Ser Ser Lys Glu Arg His Cys Ile His Val Glu
275 280 285

Phe Asp Ile Ser Glu Ser Asn Leu Lys Tyr Thr Thr Gly Asp His Leu
290 295 300

Ala Ile Trp Pro Ser Asn Ser Asp Glu Asn Ile Lys Gln Phe Ala Lys
305 310 315 320

Cys Phe Gly Leu Glu Asp Lys Leu Asp Thr Val Ile Glu Leu Lys Ala
325 330 335

Leu Asp Ser Thr Tyr Thr Ile Pro Phe Pro Thr Pro Ile Thr Tyr Gly
340 345 350

Ala Val Ile Arg His His Leu Glu Ile Ser Gly Pro Val Ser Arg Gln
355 360 365

Phe Phe Leu Ser Ile Ala Gly Phe Ala Pro Asp Glu Glu Thr Lys Lys
370 375 380

Thr Phe Thr Arg Leu Gly Gly Asp Lys Gln Glu Phe Ala Thr Lys Val
385 390 395 400

Thr Arg Arg Lys Phe Asn Ile Ala Asp Ala Leu Leu Tyr Ser Ser Asn
405 410 415

Asn Thr Pro Trp Ser Asp Val Pro Phe Glu Phe Leu Ile Glu Asn Ile
420 425 430

Gln His Leu Thr Pro Arg Tyr Tyr Ser Ile Ser Ser Ser Ser Leu Ser
435 440 445

Glu Lys Gln Leu Ile Asn Val Thr Ala Val Val Glu Ala Glu Glu Glu
450 455 460

Ala Asp Gly Arg Pro Val Thr Gly Val Val Thr Asn Leu Leu Lys Asn
465 470 475 480

Ile Glu Ile Ala Gln Asn Lys Thr Gly Glu Lys Pro Leu Val His Tyr
485 490 495

Asp Leu Ser Gly Pro Arg Gly Lys Phe Asn Lys Phe Lys Leu Pro Val
500 505 510

His Val Arg Arg Ser Asn Phe Lys Leu Pro Lys Asn Ser Thr Thr Pro
515 520 525

FIG. 5B

Val Ile Leu Ile Gly Pro Gly Thr Gly Val Ala Pro Leu Arg Gly Phe
530 535 540

Val Arg Glu Arg Val Gln Gln Val Lys Asn Gly Val Asn Val Gly Lys
545 550 555 560

Thr Leu Leu Phe Tyr Gly Cys Arg Asn Ser Asn Glu Asp Phe Leu Tyr
565 570 575

Lys Gln Glu Trp Ala Glu Tyr Ala Ser Val Leu Gly Glu Asn Phe Glu
580 585 590

Met Phe Asn Ala Phe Ser Arg Gln Asp Pro Ser Lys Lys Val Tyr Val
595 600 605

Gln Asp Lys Ile Leu Glu Asn Ser Gln Leu Val His Glu Leu Leu Thr
610 615 620

Glu Gly Ala Ile Ile Tyr Val Cys Gly Asp Ala Ser Arg Met Ala Arg
625 630 635 640

Asp Val Gln Thr Thr Ile Ser Lys Ile Val Ala Lys Ser Arg Glu Ile
645 650 655

Ser Glu Asp Lys Ala Ala Glu Leu Val Lys Ser Trp Lys Val Gln Asn
660 665 670

Arg Tyr Gln Glu Asp Val Trp
675

FIG. 5C

```
CATATGCGCT AATCTTCTTT TTCTTTTTAT CACAGGAGAA ACTATCCCAC CCCCACTTCG    60
AAACACAATG ACAACTCCTG CGTAACTTGC AAATTCTTGT CTGACTAATT GAAAACTCCG   120
GACGAGTCAG ACCTCCAGTC AAACGGACAG ACAGACAAAC ACTTGGTGCG ATGTTCATAC   180
CTACAGACAT GTCAACGGGT GTTAGACGAC GGTTTCTTGC AAAGACAGGT GTTGGCATCT   240
CGTACGATGG CAACTGCAGG AGGTGTCGAC TTCTCCTTTA GGCAATAGAA AAAGACTAAG   300
AGAACAGCGT TTTTACAGGT TGCATTGGTT AATGTAGTAT TTTTTTAGTC CCAGCATTCT   360
GTGGGTTGCT CTGGGTTTCT AGAATAGGAA ATCACAGGAG AATGCAAATT CAGATGGAAG   420
AACAAAGAGA TAAAAAACAA AAAAAAACTG AGTTTTGCAC CAATAGAATG TTTGATGATA   480
TCATCCACTC GCTAAACGAA TCATGTGGGT GATCTTCTCT TTAGTTTTGG TCTATCATAA   540
AACACATGAA AGTGAAATCC AAATACACTA CACTCCGGGT ATTGTCCTTC GTTTTACAGA   600
TGTCTCATTG TCTTACTTTT GAGGTCATAG GAGTTGCCTG TGAGAGATCA CAGAGATTAT   660
CACACTCACA TTTATCGTAG TTTCCTATCT CATGCTGTGT GTCTCTGGTT GGTTCATGAG   720
TTTGGATTGT TGTACATTAA AGGAATCGCT GGAAAGCAAA GCTAACTAAA TTTTCTTTGT   780
CACAGGTACA CTAACCTGTA AAACTTCACT GCCACGCCAG TCTTTCCTGA TTGGGCAAGT   840
GCACAAACTA CAACCTGCAA AACAGCACTC CGCTTGTCAC AGGTTGTCTC CTCTCAACCA   900
ACAAAAAAAT AAGATTAAAC TTTCTTTGCT CATGCATCAA TCGGAGTTAT CTCTGAAAGA   960
GTTGCCTTTG TGTAATGTGT GCCAAACTCA AACTGCAAAA CTAACCACAG AATGATTTCC  1020
CTCACAATTA TATAAACTCA CCCACATTTC CACAGACCGT AATTTCATGT CTCACTTTCT  1080
CTTTTGCTCT TCTTTTACTT AGTCAGGTTT GATAACTTCC TTTTTTATTA CCCTATCTTA  1140
TTTATTTATT TATTCATTTA TACCAACCAA CCAACCATGG CCACACAAGA AATCATCGAT  1200
TCTGTACTTC CGTACTTGAC CAAATGGTAC ACTGTGATTA CTGCAGCAGT ATTAGTCTTC  1260
CTTATCTCCA CAAACATCAA GAACTACGTC AAGGCAAAGA AATTGAAATG TGTCGATCCA  1320
CCATACTTGA AGGATGCCGG TCTCACTGGT ATTCTGTCTT TGATCGCCGC CATCAAGGCC  1380
AAGAACGACG GTAGATTGGC TAACTTTGCC GATGAAGTTT TCGACGAGTA CCCAAACCAC  1440
ACCTTCTACT TGTCTGTTGC CGGTGCTTTG AAGATTGTCA TGACTGTTGA CCCAGAAAAC  1500
ATCAAGGCTG TCTTGGCCAC CCAATTCACT GACTTCTCCT TGGGTACCAG ACACGCCCAC  1560
```

FIG. 6A

TTTGCTCCTT TGTTGGGTGA CGGTATCTTC ACCTTGGACG GAGAAGGTTG GAAGCACTCC 1620
AGAGCTATGT TGAGACCACA GTTTGCTAGA GACCAGATTG GACACGTTAA AGCCTTGGAA 1680
CCACACATCC AAATCATGGC TAAGCAGATC AAGTTGAACC AGGGAAAGAC TTTCGATATC 1740
CAAGAATTGT TCTTTAGATT TACCGTCGAC ACCGCTACTG AGTTCTTGTT TGGTGAATCC 1800
GTTCACTCCT TGTACGATGA AAAATTGGGC ATCCCAACTC CAAACGAAAT CCCAGGAAGA 1860
GAAAACTTTG CCGCTGCTTT CAACGTTTCC CAACACTACT TGGCCACCAG AAGTTACTCC 1920
CAGACTTTTT ACTTTTTGAC CAACCCTAAG GAATTCAGAG ACTGTAACGC CAAGGTCCAC 1980
CACTTGGCCA AGTACTTTGT CAACAAGGCC TTGAACTTTA CTCCTGAAGA ACTCGAAGAG 2040
AAATCCAAGT CCGGTTACGT TTTCTTGTAC GAATTGGTTA AGCAAACCAG AGATCCAAAG 2100
GTCTTGCAAG ATCAATTGTT GAACATTATG GTTGCCGGAA GAGACACCAC TGCCGGTTTG 2160
TTGTCCTTTG CTTTGTTTGA ATTGGCTAGA CACCCAGAGA TGTGGTCCAA GTTGAGAGAA 2220
GAAATCGAAG TTAACTTTGG TGTTGGTGAA GACTCCCGCG TTGAAGAAAT TACCTTCGAA 2280
GCCTTGAAGA GATGTGAATA CTTGAAGGCT ATCCTTAACG AAACCTTGCG TATGTACCCA 2340
TCTGTTCCTG TCAACTTTAG AACCGCCACC AGAGACACCA CTTTGCCAAG AGGTGGTGGT 2400
GCTAACGGTA CCGACCCAAT CTACATTCCT AAAGGCTCCA CTGTTGCTTA CGTTGTCTAC 2460
AAGACCCACC GTTTGGAAGA ATACTACGGT AAGGACGCTA ACGACTTCAG ACCAGAAAGA 2520
TGGTTTGAAC CATCTACTAA GAAGTTGGGC TGGGCTTATG TTCCATTCAA CGGTGGTCCA 2580
AGAGTCTGCT TGGGTCAACA ATTCGCCTTG ACTGAAGCTT CTTATGTGAT CACTAGATTG 2640
GCCCAGATGT TTGAAACTGT CTCATCTGAT CCAGGTCTCG AATACCCTCC ACCAAAGTGT 2700
ATTCACTTGA CCATGAGTCA CAACGATGGT GTCTTTGTCA AGATGTAAAG TAGTCGATGC 2760
TGGGTATTCG ATTACATGTG TATAGGAAGA TTTTGGTTTT TTATTCGTTC TTTTTTTTAA 2820
TTTTTGTTAA ATTAGTTTAG AGATTTCATT AATACATAGA TGGGTGCTAT TTCCGAAACT 2880
TTACTTCTAT CCCCTGTATC CCTTATTATC CCTCTCAGTC ACATGATTGC TGTAATTGTC 2940
GTGCAGGACA CAAACTCCCT AACGGACTTA AACCATAAAC AAGCTCAGAA CCATAAGCCG 3000
ACATCACTCC TTCTTCTCTC TTCTCCAACC AATAGCATGG ACAGACCCAC CCTCCTATCC 3060
GAATCGAAGA CCCTTATTGA CTCCATACCC ACCTGGAAGC CCCTCAAGCC ACACACGTCA 3120
TCCAGCCCAC CCATCACCAC ATCCCTCTAC TCGACAACGT CCAAAGACGG CGAGTTCTGG 3180

FIG. 6B

TGTGCCCGGA AATCAGCCAT CCCGGCCACA TACAAGCAGC CGTTGATTGC GTGCATACTC 3240

GGCGAGCCCA CAATGGGAGC CACGCATTCG GACCATGAAG CAAAGTACAT TCACGAGATC 3300

ACGGGTGTTT CAGTGTCGCA GATTGAGAAG TTCGACGATG GATGGAAGTA CGATCTCGTT 3360

GCGGATTACG ACTTCGGTGG GTTGTTATCT AAACGAAGAT TCTATGAGAC GCAGCATGTG 3420

TTTCGGTTCG AGGATTGTGC GTACGTCATG AGTGTGCCTT TTGATGGACC CAAGGAGGAA 3480

GGTTACGTGG TTGGGACGTA CAGATCCATT GAAAGGTTGA GCTGGGGTAA AGACGGGGAC 3540

GTGGAGTGGA CCATGGCGAC GACGTCGGAT CCTGGTGGGT TTATCCCGCA ATGGATAACT 3600

CGATTGAGCA TCCCTGGAGC AATCGCAAAA GATGTGCCTA GTGTATTAAA CTACATACAG 3660

AAATAAAAAC GTGTCTTGAT TCATTGGTTT GGTTCTTGTT GGGTTCCGAG CCAATATTTC 3720

ACATCATCTC CTAAATTCTC CAAGAATCCC AACGTAGCGT AGTCCAGCAC GCCCTCTGAG 3780

ATCTTATTTA ATATCGACTT CTCAACCACC GGTGGAATCC CGTTCAGACC ATTGTTACCT 3840

GTAGTGTGTT TGCTCTTGTT CTTGATGACA ATGATGTATT TGTCACGATA CCTGAAATAA 3900

TAAAACATCC AGTCATTGAG CTTATTACTC GTGAACTTAT GAAAGAACTC ATTCAAGCCG 3960

TTCCCAAAAA ACCCAGAATT GAAGATCTTG CTCAACTGGT CATGCAAGTA GTAGATCGCC 4020

ATGATCTGAT ACTTTACCAA GCTATCCTCT CCAAGTTCTC CCACGTACGG CAAGTACGGC 4080

AACGAGCTCT GGAAGCTTTG TTGTTTGGGG TCATA 4115

FIG. 6C

```
gacctgtgac gcttccggtg tcttgccacc agtctccaag ttgaccgacg cccaagtcat 60
gtaccacttt atttccggtt acacttccaa gatggctggt actgaagaag gtgtcacgga 120
accacaagct actttctccg cttgtttcgg tcaaccattc ttggtgttgc acccaatgaa 180
gtacgctcaa caattgtctg acaagatctc gcaacacaag gctaacgcct ggttgttgaa 240
caccggttgg gttggttctt ctgctgctag aggtggtaag agatgctcat tgaagtacac 300
cagagccatt ttggacgcta tccactctgg tgaattgtcc aaggttgaat acgaaacttt 360
cccagtcttc aacttgaatg tcccaacctc ctgtccaggt gtcccaagtg aaatcttgaa 420
cccaaccaag gcctggaccg gaaggtgttg actccttcaa caaggaaatc aagtctttgg 480
ctggtaagtt tgctgaaaac ttcaagacct atgctgacca agctaccgct gaagtgagag 540
ctgcaggtcc agaagcttaa agatatttat tcattattta gtttgcctat ttatttctca 600
ttacccatca tcattcaaca ctatatataa agttacttcg gatatcattg taatcgtgcg 660
tgtcgcaatt ggatgatttg gaactgcgct tgaaacggat tcatgcacga agcggagata 720
aaagattacg taatttatct cctgagacaa ttttagccgt gttcacacgc ccttctttgt 780
tctgagcgaa ggataaataa ttagacttcc acagctcatt ctaatttccg tcacgcgaat 840
attgaagggg ggtacatgtg gccgctgaat gtgggggcag taaacgcagt ctctcctctc 900
ccaggaatag tgcaacggag gaaggataac ggatagaaag cggaatgcga ggaaaatttt 960
gaacgcgcaa gaaaagcaat atccgggcta ccaggttttg agccagggaa cacactccta 1020
tttctgctca atgactgaac atagaaaaaa caccaagacg caatgaaacg cacatggaca 1080
tttagacctc cccacatgtg atagtttgtc ttaacagaaa agtataataa gaacccatgc 1140
cgtccctttt ctttcgccgc ttcaactttt ttttttttat cttacacaca tcacgaccat 1200
gactgtacac gatattatcg ccacatactt caccaaatgg tacgtgatag taccactcgc 1260
tttgattgct tatagagtcc tcgactactt ctatggcaga tacttgatgt acaagcttgg 1320
tgctaaacca tttttccaga aacagacaga cggctgtttc ggattcaaag ctccgcttga 1380
attgttgaag aagaagagcg acggtaccct catagacttc acactccagc gtatccacga 1440
tctcgatcgt cccgatatcc caactttcac attcccggtc ttttccatca accttgtcaa 1500
taccccttgag ccggagaaca tcaaggccat cttggccact cagttcaacg atttctcctt 1560
gggtaccaga cactcgcact ttgctccttt gttgggtgat ggtatcttta cgttggatgg 1620
cgccggctgg aagcacagca gatctatgtt gagaccacag tttgccagag aacagatttc 1680
ccacgtcaag ttgttggagc cacacgttca ggtgttcttc aaacacgtca gaaaggcaca 1740
gggcaagact tttgacatcc aggaattgtt tttcagattg accgtcgact ccgccaccga 1800
gtttttgttt ggtgaatccg ttgagtcctt gagagatgaa tctatcggca tgtccatcaa 1860
tgcgcttgac tttgacggca aggctggctt tgctgatgct tttaactatt cgcagaatta 1920
tttggcttcg agagcggtta tgcaacaatt gtactgggtg ttgaacggga aaaagtttaa 1980
ggagtgcaac gctaaagtgc acaagtttgc tgactactac gtcaacaagg ctttggactt 2040
gacgcctgaa caattggaaa agcaggatgg ttatgtgttt ttgtacgaat tggtcaagca 2100
aaccagagac aagcaagtgt tgagagacca attgttgaac atcatggttg ctggtagaga 2160
caccaccgcc ggtttgttgt cgtttgtttt ctttgaattg gccagaaacc cagaagttac 2220
caacaagttg agagaagaaa ttgaggacaa gtttggactc ggtgagaatg ctagtgttga 2280
agacatttcc tttgagtcgt tgaagtcctg tgaatacttg aaggctgttc tcaacgaaac 2340
cttgagattg tacccatccg tgccacagaa tttcagagtt gccaccaaga acactaccct 2400
cccaagaggt ggtggtaagg acgggttgtc tcctgttttg gtgagaaagg gtcagaccgt 2460
tatttacggt gtctacgcag cccacagaaa cccagctgtt tacggtaagg acgctcttga 2520
gtttagacca gagagatggt ttgagccaga gacaaagaag cttggctggg ccttcctccc 2580
attcaacggt ggtccaagaa tctgtttggg acagcagttt gccttgacag aagcttcgta 2640
tgtcactgtc aggttgctcc aggagtttgc acacttgtct atggacccag acaccgaata 2700
tccacctaag aaaatgtcgc atttgaccat gtcgcttttc gacggtgcca atattgagat 2760
gtattagagg gtcatgtgtt attttgattg tttagtttgt aattactgat taggttaatt 2820
catggattgt tatttattga taggggtttg cgcgtgttgc attcacttgg gatcgttcca 2880
ggttgatgtt tcctttccatc ctgtcgagtc aaaaggagtt ttgttttgta actccggacg 2940
```

FIG. 7A atgttttaaa tagaaggtcg atctccatgt gattgttttg actgttactg tgattatgta 3000
atctgcggac gttatacaag catgtgattg tggttttgca gccttttgca cgacaaatga 3060
tcgtcagacg attacgtaat ctttgttaga ggggtaaaaa aaaacaaaat ggcagccaga 3120
atttcaaaca ttctgcaaac aatgcaaaaa atgggaaact ccaacagaca aaaaaaaaaa 3180
ctccgcagca ctccgaaccc acagaacaat ggggcgccag aattattgac tattgtgact 3240
tttttacgct aacgctcatt gcagtgtagt gcgtcttaca cggggtattg ctttctacaa 3300
tgcaagggca cagttgaagg tttgcaccta acgttgcccc gtgtcaactc aatttgacga 3360
gtaacttcct aagctcgaat tatgcagctc gtgcgtcaac ctatgtgcag gaaagaaaaa 3420
atccaaaaaa atcgaaaatg cgactttcga ttttgaataa accaaaaaga aaaatgtcgc 3480
actttttctt cgctctcgct ctctcgaccc aaatcacaac aaatcctcgc gcgcagtatt 3540
tcgacgaaac cacaacaaat aaaaaaaaca aattctacac cacttctttt tcttcaccag 3600
tcaacaaaaa acaacaaatt atacaccatt tcaacgattt ttgctcttat aaatgctata 3660
taatggttta attcaactca ggtatgttta ttttactgtt ttcagctcaa gtatgttcaa 3720
atactaacta cttttgatgt ttgtcgcttt tctagaatca aaacaacgcc cacaacacgc 3780
cgagcttgtc gaatagacgg tttgtttact cattagatgg tcccagatta cttttcaagc 3840
caaagtctct cgagttttgt ttgctgtttc cccaattcct aactatgaag ggtttttata 3900
aggtccaaag accccaaggc atagtttttt tggttccttc ttgtcgtg 3948

FIG. 7B

```
GCTCAACAAT TGTCTGACAA GATCTCGCAA CACAAGGCTA ACGCCTGGTT GTTGAACACT     60
GGTTGGGTTG GTTCTTCTGC TGCTAGAGGT GGTAAGAGAT GTTCATTGAA GTACACCAGA    120
GCCATTTTGG ACGCTATCCA CTCTGGTGAA TTGTCCAAGG TTGAATACGA GACTTTCCCA    180
GTCTTCAACT TGAATGTCCC AACCTCCTGC CCAGGTGTCC CAAGTGAAAT CTTGAACCCA    240
ACCAAGGCCT GGACCGAAGG TGTTGACTCC TTCAACAAGG AAATCAAGTC TTTGGCTGGT    300
AAGTTTGCTG AAAACTTCAA GACCTATGCT GACCAAGCTA CCGCTGAAGT TAGAGCTGCA    360
GGTCCAGAAG CTTAAAGATA TTTATTCACT ATTTAGTTTG CCTATTTATT TCTCATCACC    420
CATCATCATT CAACAATATA TATAAAGTTA TTTCGGAACT CATATATCAT TGTAATCGTG    480
CGTGTTGCAA TTGGGTAATT TGAAACTGTA GTTGGAACGG ATTCATGCAC GATGCGGAGA    540
TAACACGAGA TTATCTCCTA AGACAATTTT GGCCTCATTC ACACGCCCTT CTTCTGAGCT    600
AAGGATAAAT AATTAGACTT CACAAGTTCA TTAAAATATC CGTCACGCGA AAACTGCAAC    660
AATAAGGAAG GGGGGGGTAG ACGTAGCCGA TGAATGTGGG GTGCCAGTAA ACGCAGTCTC    720
TCTCTCCCCC CCCCCCCCCC CCCCCTCAGG AATAGTACAA CGGGGGAAGG ATAACGGATA    780
GCAAGTGGAA TGCGAGGAAA ATTTTGAATG CGCAAGGAAA GCAATATCCG GGCTATCAGG    840
TTTTGAGCCA GGGGACACAC TCCTCTTCTG CACAAAAACT TAACGTAGAC AAAAAAAAAA    900
AACTCCACCA AGACACAATG AATCGCACAT GGACATTTAG ACCTCCCCAC ATGTGAAAGC    960
TTCTCTGGCG AAAGCAAAAA AAGTATAATA AGGACCCATG CCTTCCCTCT TCCTGGGCCG   1020
TTTCAACTTT TTCTTTTTCT TTGTCTATCA ACACACACAC ACCTCACGAC CATGACTGCA   1080
CAGGATATTA TCGCCACATA CATCACCAAA TGGTACGTGA TAGTACCACT CGCTTTGATT   1140
GCTTATAGGG TCCTCGACTA CTTTTACGGC AGATACTTGA TGTACAAGCT TGGTGCTAAA   1200
CCGTTTTTCC AGAAACAAAC AGACGGTTAT TTCGGATTCA AAGCTCCACT TGAATTGTTA   1260
AAAAAGAAGA GTGACGGTAC CCTCATAGAC TTCACTCTCG AGCGTATCCA AGCGCTCAAT   1320
CGTCCAGATA TCCCAACTTT TACATTCCCA ATCTTTTCCA TCAACCTTAT CAGCACCCTT   1380
GAGCCGGAGA ACATCAAGGC TATCTTGGCC ACCCAGTTCA ACGATTTCTC CTTGGGCACC   1440
AGACACTCGC ACTTTGCTCC TTTGTTGGGC GATGGTATCT TTACCTTGGA CGGTGCCGGC   1500
TGGAAGCACA GCAGATCTAT GTTGAGACCA CAGTTTGCCA GAGAACAGAT TTCCCACGTC   1560
```

FIG. 8A

```
AAGTTGTTGG AGCCACACAT GCAGGTGTTC TTCAAGCACG TCAGAAAGGC ACAGGGCAAG   1620
ACTTTTGACA TCCAAGAATT GTTTTTCAGA TTGACCGTCG ACTCCGCCAC TGAGTTTTTG   1680
TTTGGTGAAT CCGTTGAGTC CTTGAGAGAT GAATCTATTG GGATGTCCAT CAATGCACTT   1740
GACTTTGACG GCAAGGCTGG CTTTGCTGAT GCTTTTAACT ACTCGCAGAA CTATTTGGCT   1800
TCGAGAGCGG TTATGCAACA ATTGTACTGG GTGTTGAACG GGAAAAAGTT TAAGGAGTGC   1860
AACGCTAAAG TGCACAAGTT TGCTGACTAT TACGTCAGCA AGGCTTTGGA CTTGACACCT   1920
GAACAATTGG AAAAGCAGGA TGGTTATGTG TTCTTGTACG AGTTGGTCAA GCAAACCAGA   1980
GACAGGCAAG TGTTGAGAGA CCAGTTGTTG AACATCATGG TTGCCGGTAG AGACACCACC   2040
GCCGGTTTGT TGTCGTTTGT TTTCTTTGAA TTGGCCAGAA ACCCAGAGGT GACCAACAAG   2100
TTGAGAGAAG AAATCGAGGA CAAGTTTGGT CTTGGTGAGA ATGCTCGTGT TGAAGACATT   2160
TCCTTTGAGT CGTTGAAGTC ATGTGAATAC TTGAAGGCTG TTCTCAACGA AACTTTGAGA   2220
TTGTACCCAT CCGTGCCACA GAATTTCAGA GTTGCCACCA AAAACACTAC CCTTCCAAGG   2280
GGAGGTGGTA AGGACGGGTT ATCTCCTGTT TTGGTCAGAA AGGGTCAAAC CGTTATGTAC   2340
GGTGTCTACG CTGCCCACAG AAACCCAGCT GTCTACGGTA AGGACGCCCT TGAGTTTAGA   2400
CCAGAGAGGT GGTTTGAGCC AGAGACAAAG AAGCTTGGCT GGGCCTTCCT TCCATTCAAC   2460
GGTGGTCCAA GAATTTGCTT GGGACAGCAG TTTGCCTTGA CAGAAGCTTC GTATGTCACT   2520
GTCAGATTGC TCCAAGAGTT TGGACACTTG TCTATGGACC CCAACACCGA ATATCCACCT   2580
AGGAAAATGT CGCATTTGAC CATGTCCCTT TTCGACGGTG CCAACATTGA GATGTATTAG   2640
AGGATCATGT GTTATTTTTG ATTGGTTTAG TCTGTTTGTA GCTATTGATT AGGTTAATTC   2700
ACGGATTGTT ATTTATTGAT AGGGGGTGCG TGTGTGTGTG TGTGTTGCAT TCACATGGGA   2760
TCGTTCCAGG TTGTTGTTTC CTTCCATCCT GTTGAGTCAA AAGGAGTTTT GTTTTGTAAC   2820
TCCGGACGAT GTCTTAGATA GAAGGTCGAT CTCCATGTGA TTGTTTGACT GCTACTCTGA   2880
TTATGTAATC TGTAAAGCCT AGACGTTATG CAAGCATGTG ATTGTGGTTT TTGCAACCTG   2940
TTTGCACGAC AAATGATCGA CAGTCGATTA CGTAATCCAT ATTATTTAGA GGGGTAATAA   3000
AAAATAAATG GCAGCCAGAA TTTCAAACAT TTTGCAAACA ATGCAAAAGA TGAGAAACTC   3060
CAACAGAAAA AATAAAAAAA CTCCGCAGCA CTCCGAACCA ACAAAACAAT GGGGGGCGCC   3120
AGAATTATTG ACTATTGTGA CTTTTTTTTA TTTTTTCCGT TAACTTTCAT TGCAGTGAAG   3180
```

FIG. 8B

```
TGTGTTACAC GGGGTGGTGA TGGTGTTGGT TTCTACAATG CAAGGGCACA GTTGAAGGTT    3240
TCCACATAAC GTTGCACCAT ATCAACTCAA TTTATCCTCA TTCATGTGAT AAAAGAAGAG    3300
CCAAAAGGTA ATTGGCAGAC CCCCCAAGGG GAACACGGAG TAGAAAGCAA TGGAAACACG    3360
CCCATGACAG TGCCATTTAG CCCACAACAC ATCTAGTATT CTTTTTTTTT TTTGTGCGCA    3420
GGTGCACACC TGGACTTTAG TTATTGCCCC ATAAAGTTAA CAATCTCACC TTTGGCTCTC    3480
CCAGTGTCTC CGCCTCCAGA TGCTCGTTTT ACACCCTCGA GCTAACGACA ACACAACACC    3540
CATGAGGGGA ATGGGCAAAG TTAAACACTT TTGGTTTCAA TGATTCCTAT TTGCTACTCT    3600
CTTGTTTTGT GTTTTGATTT GCACCATGTG AAATAAACGA CAATTATATA TACCTTTTCG    3660
TCTGTCCTCC AATGTCTCTT TTTGCTGCCA TTTTGCTTTT TGCTTTTTGC TTTTGCACTC    3720
TCTCCCACTC CCACAATCAG TGCAGCAACA CACAA                               3755
```

FIG. 8C

GACATCATAA TGACCCGGTT ATTTCGCCCT CAGGTTGCTT ATTTGAGCCG TAAAGTGCAG 60
TAGAAACTTT GCCTTGGGTT CAAACTCTAG TATAATGGTG ATAACTGGTT GCACTCTTGC 120
CATAGGCATG AAAATAGGCC GTTATAGTAC TATATTTAAT AAGCGTAGGA GTATAGGATG 180
CATATGACCG GTTTTTCTAT ATTTTTAAGA TAATCTCTAG TAAATTTTGT ATTCTCAGTA 240
GGATTTCATC AAATTTCGCA ACCAATTCTG GCGAAAAAAT GATTCTTTTA CGTCAAAAGC 300
TGAATAGTGC AGTTTAAAGC ACCTAAAATC ACATATACAG CCTCTAGATA CGACAGAGAA 360
GCTCTTTATG ATCTGAAGAA GCATTAGAAT AGCTACTATG AGCCACTATT GGTGTATATA 420
TTAGGGATTG GTGCAATTAA GTACGTACTA ATAAACAGAA GAAAATACTT AACCAATTTC 480
TGGTGTATAC TTAGTGGTGA GGGACCTTTT CTGAACATTC GGGTCAAACT TTTTTTTGGA 540
GTGCGACATC GATTTTTCGT TTGTGTAATA ATAGTGAACC TTTGTGTAAT AAATCTTCAT 600
GCAAGACTTG CATAATTCGA GCTTGGGAGT TCACGCCAAT TTGACCTCGT TCATGTGATA 660
AAAGAAAAGC CAAAAGGTAA TTAGCAGACG CAATGGGAAC ATGGAGTGGA AAGCAATGGA 720
AGCACGCCCA GGACGGAGTA ATTTAGTCCA CACTACATCT GGGGGTTTTT TTTTTGTGCG 780
CAAGTACACA CCTGGACTTT AGTTTTTGCC CCATAAAGTT AACAATCTAA CCTTTGGCTC 840
TCCAACTCTC TCCGCCCCCA AATATTCGTT TTTACACCCT CAAGCTAGCG ACAGCACAAC 900
ACCCATTAGA GGAATGGGGC AAAGTTAAAC ACTTTTGGCT TCAATGATTC CTATTCGCTA 960
CTACATTCTT CTCTTGTTTT GTGCTTTGAA TTGCACCATG TGAAATAAAC GACAATTATA 1020
TATACCTTTT CATCCCTCCT CCTATATCTC TTTTTGCTAC ATTTTGTTTT TTACGTTTCT 1080
TGCTTTTGCA CTCTCCCACT CCCACAAAGA AAAAAAAACT ACACTATGTC GTCTTCTCCA 1140
TCGTTTGCCC AAGAGGTTCT CGCTACCACT AGTCCTTACA TCGAGTACTT TCTTGACAAC 1200
TACACCAGAT GGTACTACTT CATACCTTTG GTGCTTCTTT CGTTGAACTT TATAAGTTTG 1260
CTCCACACAA GGTACTTGGA ACGCAGGTTC CACGCCAAGC CACTCGGTAA CTTTGTCAGG 1320
GACCCTACGT TTGGTATCGC TACTCCGTTG CTTTTGATCT ACTTGAAGTC GAAAGGTACG 1380
GTCATGAAGT TTGCTTGGGG CCTCTGGAAC AACAAGTACA TCGTCAGAGA CCCAAAGTAC 1440
AAGACAACTG GGCTCAGGAT TGTTGGCCTC CCATTGATTG AAACCATGGA CCCAGAGAAC 1500
ATCAAGGCTG TTTTGGCTAC TCAGTTCAAT GATTTCTCTT TGGGAACCAG ACACGATTTC 1560

FIG. 9A

TTGTACTCCT TGTTGGGTGA CGGTATTTTC ACCTTGGACG GTGCTGGCTG GAAACATAGT 1620
AGAACTATGT TGAGACCACA GTTTGCTAGA GAACAGGTTT CTCACGTCAA GTTGTTGGAG 1680
CCACACGTTC AGGTGTTCTT CAAGCACGTT AGAAAGCACC GCGGTCAAAC GTTCGACATC 1740
CAAGAATTGT TCTTCAGGTT GACCGTCGAC TCCGCCACCG AGTTCTTGTT TGGTGAGTCT 1800
GCTGAATCCT TGAGGGACGA ATCTATTGGA TTGACCCCAA CCACCAAGGA TTTCGATGGC 1860
AGAAGAGATT TCGCTGACGC TTTCAACTAT TCGCAGACTT ACCAGGCCTA CAGATTTTTG 1920
TTGCAACAAA TGTACTGGAT CTTGAATGGC TCGGAATTCA GAAAGTCGAT TGCTGTCGTG 1980
CACAAGTTTG CTGACCACTA TGTGCAAAAG GCTTTGGAGT TGACCGACGA TGACTTGCAG 2040
AAACAAGACG GCTATGTGTT CTTGTACGAG TTGGCTAAGC AAACCAGAGA CCCAAAGGTC 2100
TTGAGAGACC AGTTATTGAA CATTTTGGTT GCCGGTAGAG ACACGACCGC CGGTTTGTTG 2160
TCATTTGTTT TCTACGAGTT GTCAAGAAAC CCTGAGGTGT TTGCTAAGTT GAGAGAGGAG 2220
GTGGAAAACA GATTTGGACT CGGTGAAGAA GCTCGTGTTG AAGAGATCTC GTTTGAGTCC 2280
TTGAAGTCTT GTGAGTACTT GAAGGCTGTC ATCAATGAAA CCTTGAGATT GTACCCATCG 2340
GTTCCACACA ACTTTAGAGT TGCTACCAGA AACACTACCC TCCCAAGAGG TGGTGGTGAA 2400
GATGGATACT CGCCAATTGT CGTCAAGAAG GGTCAAGTTG TCATGTACAC TGTTATTGCT 2460
ACCCACAGAG ACCCAAGTAT CTACGGTGCC GACGCTGACG TCTTCAGACC AGAAAGATGG 2520
TTTGAACCAG AAACTAGAAA GTTGGGCTGG GCATACGTTC CATTCAATGG TGGTCCAAGA 2580
ATCTGTTTGG GTCAACAGTT TGCCTTGACC GAAGCTTCAT ACGTCACTGT CAGATTGCTC 2640
CAGGAGTTTG CACACTTGTC TATGGACCCA GACACCGAAT ATCCACCAAA ATTGCAGAAC 2700
ACCTTGACCT TGTCGCTCTT TGATGGTGCT GATGTTAGAA TGTACTAAGG TTGCTTTTCC 2760
TTGCTAATTT TCTTCTGTAT AGCTTGTGTA TTTAAATTGA ATCGGCAATT GATTTTTCTG 2820
ATACCAATAA CCGTAGTGCG ATTTGACCAA AACCGTTCAA ACTTTTTGTT CTCTCGTTGA 2880
CGTGCTCGCT CATCAGCACT GTTTGAAGAC GAAAGAGAAA ATTTTTTGTA AACAACACTG 2940
TCCAAATTTA CCCAACGTGA ACCATTATGC AAATGAGCGG CCCTTTCAAC TGGTCGCTGG 3000
AAGCATTCGG GGATATCTAC AACGCCCTTA AGTTTGAAAC AGACATTGAT TTAGACACCA 3060
TAGATTTCAG CGGCATCAAG AATGACCTTG CCCACATTTT GACGACCCCA ACACCACTGG 3120
AAGAATCACG CCAGAAACTA GGCGATGGAT CCAAGCCTGT GACCTTGCCC AATGGAGACG 3180

FIG. 9B

AAGTGGAGTT GAACCAAGCG TTCCTAGAAG TTACCACATT ATTGTCGAAT GAGTTTGACT 3240

TGGACCAATT GAACGCGGCA GAGTTGTTAT ACTACGCTGG CGACATATCC TACAAGAAGG 3300

GCACATCAAT CGCAGACAGT GCCAGATTGT CTTATTATTT GAGAGCAAAC TACATCTTGA 3360

ACATACTTGG GTATTTGATT TCGAAGCAGC GATTGGATTT GATAGTCACG GACAACGACG 3420

CGTTGTTTGA TAGTATTTTG AAAAGTTTTG AAAAGATCTA CAAGTTGATA AGCGTGTTGA 3480

ACGATATGAT TGACAAGCAA AAGGTGACAA GCGACATCAA CAGTCTAGCA TTCATCAATT 3540

GCATCAACTA CTCGAGAGGT CAACTATTCT CCGCACACGA ACTTTTGGGA CTGGTTTTGT 3600

TTGGATTGGT CGACATCTAT TTCAACCAGT TTGGCACATT AGACAACTAC AAGAAGGTAT 3660

TGGCATTGAT ACTGAAGAAC ATCAGCGATG AAGACATCTT GATCATACAC TTCCTCCCAT 3720

CGACACTACA ATTGTTTAAG CTGGTGTTGG ACAAGAAAGA CGACGCTGCA GTTGAACAGT 3780

TCTACAAGTA CATCACTTCA ACAGTGTCAC GAGACTACAA CTCCAACATC GGCTCCACAG 3840

CCAAAGATGA TATCGATTTG TCCAAAACCA AACTCAGTGG CTTTGAGGTG TTGACGAGTT 3900

FIG. 9C

CCTGCAGAAT TCGCGGCCGC GTCGACAGAG TAGCAGTTAT GCAAGCATGT GATTGTGGTT 60
TTTGCAACCT GTTTGCACGA CAAATGATCG ACAGTCGATT ACGTAATCCA TATTATTTAG 120
AGGGGTAATA AAAAATAAAT GGCAGCCAGA ATTTCAAACA TTTTGCAAAC AATGCAAAAG 180
ATGAGAAACT CCAACAGAAA AAATAAAAAA ACTCCGCAGC ACTCCGAACC AACAAAACAA 240
TGGGGGGCGC CAGAATTATT GACTATTGTG ACTTTTTTTT ATTTTTTCCG TTAACTTTCA 300
TTGCAGTGAA GTGTGTTACA CGGGGTGGTG ATGGTGTTGG TTTCTACAAT GCAAGGGCAC 360
AGTTGAAGGT TTCCACATAA CGTTGCACCA TATCAACTCA ATTTATCCTC ATTCATGTGA 420
TAAAAGAAGA GCCAAAAGGT AATTGGCAGA CCCCCCAAGG GGAACACGGA GTAGAAAGCA 480
ATGGAAACAC GCCCATGACA GTGCCATTTA GCCCACAACA CATCTAGTAT TCTTTTTTTT 540
TTTTGTGCGC AGGTGCACAC CTGGACTTTA GTTATTGCCC CATAAAGTTA ACAATCTCAC 600
CTTTGGCTCT CCCAGTGTCT CCGCCTCCAG ATGCTCGTTT TACACCCTCG AGCTAACGAC 660
AACACAACAC CCATGAGGGG AATGGGCAAA GTTAAACACT TTTGGTTTCA ATGATTCCTA 720
TTTGCTACTC TCTTGTTTTG TGTTTTGATT TGCACCATGT GAAATAAACG ACAATTATAT 780
ATACCTTTTC GTCTGTCCTC CAATGTCTCT TTTTGCTGCC ATTTTGCTTT TTGCTTTTTG 840
CTTTTGCACT CTCTCCCACT CCCACAATCA GTGCAGCAAC ACACAAAGAA GAAAAATAAA 900
AAAACCTACA CTATGTCGTC TTCTCCATCG TTTGCTCAGG AGGTTCTCGC TACCACTAGT 960
CCTTACATCG AGTACTTTCT TGACAACTAC ACCAGATGGT ACTACTTCAT CCCTTTGGTG 1020
CTTCTTTCGT TGAACTTCAT CAGCTTGCTC CACACAAAGT ACTTGGAACG CAGGTTCCAC 1080
GCCAAGCCGC TCGGTAACGT CGTGTTGGAT CCTACGTTTG GTATCGCTAC TCCGTTGATC 1140
TTGATCTACT TAAAGTCGAA AGGTACAGTC ATGAAGTTTG CCTGGAGCTT CTGGAACAAC 1200
AAGTACATTG TCAAAGACCC AAAGTACAAG ACCACTGGCC TTAGAATTGT CGGCCTCCCA 1260
TTGATTGAAA CCATAGACCC AGAGAACATC AAAGCTGTGT TGGCTACTCA GTTCAACGAT 1320
TTCTCCTTGG GAACTAGACA CGATTTCTTG TACTCCTTGT TGGGCGATGG TATTTTTACC 1380
TTGGACGGTG CTGGCTGGAA ACACAGTAGA ACTATGTTGA GACCACAGTT TGCTAGAGAA 1440
CAGGTTTCCC ACGTCAAGTT GTTGGAACCA CACGTTCAGG TGTTCTTCAA GCACGTTAGA 1500
AAACACCGCG GTCAGACTTT TGACATCCAA GAATTGTTCT TCAGATTGAC CGTCGACTCC 1560

FIG. 10A

GCCACCGAGT TCTTGTTTGG TGAGTCTGCT GAATCCTTGA GAGACGACTC TGTTGGTTTG 1620

ACCCCAACCA CCAAGGATTT CGAAGGCAGA GGAGATTTCG CTGACGCTTT CAACTACTCG 1680

CAGACTTACC AGGCCTACAG ATTTTTGTTG CAACAAATGT ACTGGATTTT GAATGGCGCG 1740

GAATTCAGAA AGTCGATTGC CATCGTGCAC AAGTTTGCTG ACCACTATGT GCAAAAGGCT 1800

TTGGAGTTGA CCGACGATGA CTTGCAGAAA CAAGACGGCT ATGTGTTCTT GTACGAGTTG 1860

GCTAAGCAAA CTAGAGACCC AAAGGTCTTG AGAGACCAGT TGTTGAACAT TTTGGTTGCC 1920

GGTAGAGACA CGACCGCCGG TTTGTTGTCG TTTGTGTTCT ACGAGTTGTC GAGAAACCCT 1980

GAAGTGTTTG CCAAGTTGAG AGAGGAGGTG GAAAACAGAT TTGGACTCGG CGAAGAGGCT 2040

CGTGTTGAAG AGATCTCTTT TGAGTCCTTG AAGTCCTGTG AGTACTTGAA GGCTGTCATC 2100

AATGAAGCCT TGAGATTGTA CCCATCTGTT CCACACAACT TCAGAGTTGC CACCAGAAAC 2160

ACTACCCTTC CAAGAGGCGG TGGTAAAGAC GGATGCTCGC CAATTGTTGT CAAGAAGGGT 2220

CAAGTTGTCA TGTACACTGT CATTGGTACC CACAGAGACC CAAGTATCTA CGGTGCCGAC 2280

GCCGACGTCT TCAGACCAGA AAGATGGTTC GAGCCAGAAA CTAGAAAGTT GGGCTGGGCA 2340

TATGTTCCAT TCAATGGTGG TCCAAGAATC TGTTTGGGTC AGCAGTTTGC CTTGACTGAA 2400

GCTTCATACG TCACTGTCAG ATTGCTCCAA GAGTTTGGAA ACTTGTCCCT GGATCCAAAC 2460

GCTGAGTACC CACCAAAATT GCAGAACACC TTGACCTTGT CACTCTTTGA TGGTGCTGAC 2520

GTTAGAATGT TCTAAGGTTG CTTATCCTTG CTAGTGTTAT TTATAGTTTG TGTATTTAAA 2580

TTGAATCGGC GATTGATTTT TCTGGTACTA ATAACTGTAG TGGGTTTTGA CCAAAACCGT 2640

TCAAACTTTT TTTTTTTTTT TCTTCCCCCT ACCTTCGTTG CTCGCTCATC AGCACTGTTT 2700

GAAAACGAAA AAAGAAAATT TTTTGTAAAC AACATTGCCC AAACTTACCC AACGTGAACC 2760

ATTATAACCA AATGAGCGGC GCTTTCAACT GGTCACTGGA GGCATTCGGG GATATCTACA 2820

ACACCCTTAA GTTTGAGGAA GACATTGATT TAGACACCAT AGATTTCAGC GGCATCAAGA 2880

ATGACCTTGT CCACATTTTG ACAACCCCAA CACCACTGGA AGAATCGCGC CAGAAACTAG 2940

GCGATGGATC CAAGCCTGTG GCCTTGCCCA ATGGAGACGA AGTGGAGTTG AACCAAGCGT 3000

TCCTAGAAGT TACCACATTA TTGTCGAACG AGTTTGACTT GGACCAATTG AACGCGGCCG 3060

AGTTGTTATA CTACGCCGGC GACATATCCT ACAAGAAGGG CACATCAATT GCCGACAGTG 3120

CCAGATTGTC TTACTATTTG AGAGCAAACT ACATCTTGAA CATACTTGGG TACTTTATTT 3180

FIG. 10B

CGAAGCAGCG ATTGGATGTG ATAGTCACCG ACAACAACGC GTTGTTTGAT AATATTTTGA 3240

AAAGTTTTGA AAAGATCTAC AAGTTGATAA GCGCGTTGAA CGATATGATT GACAAGCAAA 3300

AGGTGACAAG CGACATCAAC AGTCTAGCAT TTATCAACTG CATCAACTAC TCGAGGGGTC 3360

AACTATTCTC CGCACACGAA CTTTTGGGAC TGGTTTTGTT TGGATTGGTT GACAACTATT 3420

TCAACCAGTT TGGCTCATTA GACAACTACA AGAAAGTATT GGCATTGATA CTGAAGAACA 3480

TCAGTGATGA AGATATCTTG ATCGTACGCT TCCTCCCATC GACACTACAA TTGTTTAAGC 3540

TGGTGTTGGA TAAGAAAGAC GACGCCACTG TTGACCAGTT CTACAAGTAC ATCACCTCAA 3600

CAGTGTCGCA AGACTACAAC TCCAACATCG GAGCCACAGC CAAAGATGAT ATCGATTTGT 3660

CCAAAGCC 3668

FIG. 10C

```
GATGTGGTGC TTGATTTCTC GAGACACATC CTTGTGAGGT GCCATGAATC TGTACCTGTC    60
TGTAAGCACA GGGAACTGCT TCAACACCTT ATTGCATATT CTGTCTATTG CAAGCGTGTG   120
CTGCAACGAT ATCTGCCAAG GTATATAGCA GAACGTGCTG ATGGTTCCTC CGGTCATATT   180
CTGTTGGTAG TTCTGCAGGT AAATTTGGAT GTCAGGTAGT GGAGGGAGGT TTGTATCGGT   240
TGTGTTTTCT TCTTCCTCTC TCTCTGATTC AACCTCCACG TCTCCTTCGG GTTCTGTGTC   300
TGTGTCTGAG TCGTACTGTT GGATTAAGTC CATCGCATGT GTGAAAAAAA GTAGCGCTTA   360
TTTAGACAAC CAGTTCGTTG GGCGGGTATC AGAAATAGTC TGTTGTGCAC GACCATGAGT   420
ATGCAACTTG ACGAGACGTC GTTAGGAATC CACAGAATGA TAGCAGGAAG CTTACTACGT   480
GAGAGATTCT GCTTAGAGGA TGTTCTCTTC TTGTTGATTC CATTAGGTGG GTATCATCTC   540
CGGTGGTGAC AACTTGACAC AAGCAGTTCC GAGAACCACC CACAACAATC ACCATTCCAG   600
CTATCACTTC TACATGTCAA CCTACGATGT ATCTCATCAC CATCTAGTTT CTTGGCAATC   660
GTTTATTTGT TATGGGTCAA CATCCAATAC AACTCCACCA ATGAAGAAGA AAAACGGAAA   720
GCAGAATACC AGAATGACAG TGTGAGTTCC TGACCATTGC TAATCTATGG CTATATCTAG   780
TTTGCTATCG TGGGATGTGA TCTGTGTCGT CTTCATTTGC GTTTGTGTTT ATTTCGGGTA   840
TGAATATTGT TATACTAAAT ACTTGATGCA CAAACATGGC GCTCGAGAAA TCGAGAATGT   900
GATCAACGAT GGGTTCTTTG GGTTCCGCTT ACCTTTGCTA CTCATGCGAG CCAGCAATGA   960
GGGCCGACTT ATCGAGTTCA GTGTCAAGAG ATTCGAGTCG GCGCCACATC CACAGAACAA  1020
GACATTGGTC AACCGGGCAT TGAGCGTTCC TGTGATACTC ACCAAGGACC CAGTGAATAT  1080
CAAAGCGATG CTATCGACCC AGTTTGATGA CTTTTCCCTT GGGTTGAGAC TACACCAGTT  1140
TGCGCCGTTG TTGGGGAAAG GCATCTTTAC TTTGGACGGC CCAGAGTGGA AGCAGAGCCG  1200
ATCTATGTTG CGTCCGCAAT TTGCCAAAGA TCGGGTTTCT CATATCCTGG ATCTAGAACC  1260
GCATTTTGTG TTGCTTCGGA AGCACATTGA TGGCCACAAT GGAGACTACT TCGACATCCA  1320
GGAGCTCTAC TTCCGGTTCT CGATGGATGT GGCGACGGGG TTTTTGTTTG GCGAGTCTGT  1380
GGGGTCGTTG AAAGACGAAG ATGCGAGGTT CCTGGAAGCA TTCAATGAGT CGCAGAAGTA  1440
TTTGGCAACT AGGGCAACGT TGCACGAGTT GTACTTTCTT TGTGACGGGT TTAGGTTTCG  1500
CCAGTACAAC AAGGTTGTGC GAAAGTTCTG CAGCCAGTGT GTCCACAAGG CGTTAGATGT  1560
```

FIG. 11A

TGCACCGGAA GACACCAGCG AGTACGTGTT TCTCCGCGAG TTGGTCAAAC ACACTCGAGA 1620
TCCCGTTGTT TTACAAGACC AAGCGTTGAA CGTCTTGCTT GCTGGACGCG ACACCACCGC 1680
GTCGTTATTA TCGTTTGCAA CATTTGAGCT AGCCCGGAAT GACCACATGT GGAGGAAGCT 1740
ACGAGAGGAG GTTATCCTGA CGATGGGACC GTCCAGTGAT GAAATAACCG TGGCCGGGTT 1800
GAAGAGTTGC CGTTACCTCA AAGCAATCCT AAACGAAACT CTTCGACTAT ACCCAAGTGT 1860
GCCTAGGAAC GCGAGATTTG CTACGAGGAA TACGACGCTT CCTCGTGGCG GAGGTCCAGA 1920
TGGATCGTTT CCGATTTTGA TAAGAAAGGG CCAGCCAGTG GGGTATTTCA TTTGTGCTAC 1980
ACACTTGAAT GAGAAGGTAT ATGGGAATGA TAGCCATGTG TTTCGACCGG AGAGATGGGC 2040
TGCGTTAGAG GGCAAGAGTT TGGGCTGGTC GTATCTTCCA TTCAACGGCG GCCCGAGAAG 2100
CTGCCTTGGT CAGCAGTTTG CAATCCTTGA AGCTTCGTAT GTTTTGGCTC GATTGACACA 2160
GTGCTACACG ACGATACAGC TTAGAACTAC CGAGTACCCA CCAAAGAAAC TCGTTCATCT 2220
CACGATGAGT CTTCTCAACG GGGTGTACAT CCGAACTAGA ACTTGATTAT GTGTTTATGG 2280
TTAATCGGGG CAAAGCACTG CAAGTCATTG ATGTTTGTGG AAGCCCAGCA TTGGTGTTCC 2340
GGAGCATCAA TAACCAATGT CTTGAAGGGT TTGATTTTCT TGACCTTCTT CTTCCTGAGC 2400
TTCTTTCCGT CAAACTTGTA CAGAATGGCC ATCATTTCAG GAACAACCAC GTACGACGGC 2460
CGGTACCGCA TCTGGAGTAT CTCGCCGTCG TTCAAGTAGC ACGAAAACAG CAACGACGTC 2520
ACCATCTGCT TCCCAATCTT GACACCCACA GATACCCCTG CGGCTTCATG GATCAAAAAC 2580
GTCGGCAACC CCGCGTATAT GTCCATGTAA TTCTCCATGG CCACCTCCAT CAACACACTG 2640
ATGGAGCGAC TGACGGTGCC ACCACTGCCC TCGGTTGAGT CAAGGCAGTA TGATGCCGGG 2700
ATCCAGTACT CCAATGGGAA CCTCTGCACG GTGTCGCTGC AGTTTTTGAG GCGTATTTCG 2760
ATCCATGATC GTTCTTTGGT GCTGTAGTAT AACGAGCTCT TGGTGTCCTT GAAATGGAAC 2820
AGGTTGGATG TGTTGTTGAG TTTGTCTGCG TGCTTGGTTT GCAAGTCTTC GATCGAGCGT 2880
AGTGAGTAGA CAGTTGGCGG GGGTGGTGGC TCGGGCTTTA TTCTGTGTTT GTGTTTCCTT 2940
CTTAGTCTTG GAATGACGCT GTTATCGACG GTTCGTAGTA TAAGTAGCGC CAATATGAGA 3000
ATGTATATCC GCATCACCCA AGACTCTTCA GCCTGTTACA ACGACTGAGG CTGTTGGCCG 3060
TGTGACCAAT TGGTTTCTTT GGTGACCTAG ATTGGTCCCG CAGGGAAAGC AAGGGCTGCT 3120
AGGGGGGCAT ACCAAACAAG GTCGTGTAAT CAGTATCTAT GGTGCTACCA TGTGTGTGGT 3180

FIG. 11B

TGGGGGGAAA TTCCCGCATT TTTGTGTAAC GAAAGTTCTA GAAAGTTCTC GTGGGTTCTG 3240

AGAATCTGCT GGAACCATCC ACCCGCATTT CCGTTGCCAA AGTGGGAAGA GCAATCAACC 3300

CACCCTGCTT TGCCCAATCA GCCATTCCCC TGGGAATATA AATTCAAC 3348

FIG. 11C

TGGAGTCGCC AGACTTGCTC ACTTTTGACT CCCTTCGAAA CTCAAAGTAC GTTCAGGCGG 60

TGCTCAACGA AACGCTCCGT ATCTACCCGG GGGTACCACG AAACATGAAG ACAGCTACGT 120

GCAACACGAC GTTGCCACGC GGAGGAGGCA AAGACGGCAA GGAACCTATC TTGGTGCAGA 180

AGGGACAGTC CGTTGGGTTG ATTACTATTG CCACGCAGAC GGACCCAGAG TATTTTGGGG 240

CCGACGCTGG TGAGTTTAAG CCGGAGAGAT GGTTTGATTC AAGCATGAAG AACTTGGGGT 300

GTAAATACTT GCCGTTCAAT GCTGGGCCAC GGACTTGCTT GGGGCAGCAG TACACTTTGA 360

TTGAAGCGAG CTACTTGCTA GTCCGGTTGG CCCAGACCTA CCGGGCAATA GATTTGCAGC 420

CAGGATCGGC GTACCCACCA AGAAAGAAGT CGTTGATCAA CATGAGTGCT GCCGACGGGG 480

TGTTTGTAAA GCTTTATAAG GATGTAACGG TAGATGGATA GTTGTGTAGG AGGAGCGGAG 540

ATAAATTAGA TTTGATTTTG TGTAAGGTTT TGGATGTCAA CCTACTCCGC ACTTCATGCA 600

GTGTGTGTGA CACAAGGGTG TACTACGTGT GCGTGTGCGC CAAGAGACAG CCCAAGGGGG 660

TGGTAGTGTG TGTTGGCGGA AGTGCATGTG ACACAACGCG TGGGTTCTGG CCAATGGTGG 720

ACTAAGTGCA GGTAAGCAGC GACCTGAAAC ATTCCTCAAC GCTTAAGACA CTGGTGGTAG 780

AGATGCGGAC CAGGCTATTC TTGTCGTGCT ACCCGGCGCA TGGAAAATCA ACTGCGGGAA 840

GAATAAATTT ATCCGTAGAA TCCACAGAGC GGATAAATTT GCCCACCTCC ATCATCAACC 900

ACGCCGCCAC TAACTACATC ACTCCCCTAT TTTCTCTCTC TCTCTTTGTC TTACTCCGCT 960

CCCGTTTCCT TAGCCACAGA TACACACCCA CTGCAAACAG CAGCAACAAT TATAAAGATA 1020

CGCCAGGCCC ACCTTCTTTC TTTTTCTTCA CTTTTTTGAC TGCAACTTTC TACAATCCAC 1080

CACAGCCACC ACCACAGCCG CTATGATTGA ACAACTCCTA GAATATTGGT ATGTCGTTGT 1140

GCCAGTGTTG TACATCATCA AACAACTCCT TGCATACACA AAGACTCGCG TCTTGATGAA 1200

AAAGTTGGGT GCTGCTCCAG TCACAAACAA GTTGTACGAC AACGCTTTCG GTATCGTCAA 1260

TGGATGGAAG GCTCTCCAGT TCAAGAAAGA GGGCAGGGCT CAAGAGTACA ACGATTACAA 1320

GTTTGACCAC TCCAAGAACC CAAGCGTGGG CACCTACGTC AGTATTCTTT TCGGCACCAG 1380

GATCGTCGTG ACCAAAGATC CAGAGAATAT CAAAGCTATT TTGGCAACCC AGTTTGGTGA 1440

TTTTTCTTTG GGCAAGAGGC ACACTCTTTT TAAGCCTTTG TTAGGTGATG GGATCTTCAC 1500

ATTGGACGGC GAAGGCTGGA AGCACAGCAG AGCCATGTTG AGACCACAGT TTGCCAGAGA 1560

FIG. 12A

ACAAGTTGCT CATGTGACGT CGTTGGAACC ACACTTCCAG TTGTTGAAGA AGCATATTCT 1620
TAAGCACAAG GGTGAATACT TTGATATCCA GGAATTGTTC TTTAGATTTA CCGTTGATTC 1680
GGCCACGGAG TTCTTATTTG GTGAGTCCGT GCACTCCTTA AAGGACGAAT CTATTGGTAT 1740
CAACCAAGAC GATATAGATT TTGCTGGTAG AAAGGACTTT GCTGAGTCGT TCAACAAAGC 1800
CCAGGAATAC TTGGCTATTA GAACCTTGGT GCAGACGTTC TACTGGTTGG TCAACAACAA 1860
GGAGTTTAGA GACTGTACCA AGCTGGTGCA CAAGTTCACC AACTACTATG TTCAGAAAGC 1920
TTTGGATGCT AGCCCAGAAG AGCTTGAAAA GCAAAGTGGG TATGTGTTCT TGTACGAGCT 1980
TGTCAAGCAG ACAAGAGACC CCAATGTGTT GCGTGACCAG TCTTTGAACA TCTTGTTGGC 2040
CGGAAGAGAC ACCACTGCTG GGTTGTTGTC GTTTGCTGTC TTTGAGTTGG CCAGACACCC 2100
AGAGATCTGG GCCAAGTTGA GAGAGGAAAT TGAACAACAG TTTGGTCTTG GAGAAGACTC 2160
TCGTGTTGAA GAGATTACCT TTGAGAGCTT GAAGAGATGT GAGTACTTGA AAGCGTTCCT 2220
TAATGAAACC TTGCGTATTT ACCCAAGTGT CCCAAGAAAC TTCAGAATCG CCACCAAGAA 2280
CACGACATTG CCAAGGGGCG GTGGTTCAGA CGGTACCTCG CCAATCTTGA TCCAAAAGGG 2340
AGAAGCTGTG TCGTATGGTA TCAACTCTAC TCATTTGGAC CCTGTCTATT ACGGCCCTGA 2400
TGCTGCTGAG TTCAGACCAG AGAGATGGTT TGAGCCATCA ACCAAAAAGC TCGGCTGGGC 2460
TTACTTGCCA TTCAACGGTG GTCCAAGAAT CTGTTTGGGT CAGCAGTTTG CCTTGACGGA 2520
AGCTGGCTAT GTGTTGGTTA GATTGGTGCA AGAGTTCTCC CACGTTAGGC TGGACCCAGA 2580
CGAGGTGTAC CCGCCAAAGA GGTTGACCAA CTTGACCATG TGTTTGCAGG ATGGTGCTAT 2640
TGTCAAGTTT GACTAGCGGC GTGGTGAATG CGTTTGATTT TGTAGTTTCT GTTTGCAGTA 2700
ATGAGATAAC TATTCAGATA AGGCGAGTGG ATGTACGTTT TGTAAGAGTT TCCTTACAAC 2760
CTTGGTGGGG TGTGTGAGGT TGAGGTTGCA TCTTGGGGAG ATTACACCTT TTGCAGCTCT 2820
CCGTATACAC TTGTACTCTT TGTAACCTCT ATCAATCATG TGGGGGGGGG GGTTCATTGT 2880
TTGGCCATGG TGGTGCATGT TAAATCCGCC AACTACCCAA TCTCACATGA AACTCAAGCA 2940
CACTAAAAAA AAAAAAGATG TTGGGGGAAA ACTTTGGTTT CCCTTCTTAG TAATTAAACA 3000
CTCTCACTCT CACTCTCACT CTCTCCACTC AGACAAACCA ACCACCTGGG CTGCAGACAA 3060
CCAGAAAAAA AAAGAACAAA ATCCAGATAG AAAAACAAAG GGCTGGACAA CCATAAATAA 3120
ACAATCTAGG GTCTACTCCA TCTTCCACTG TTTCTTCTTC TTCAGACTTA GCTAACAAAC 3180

FIG. 12B

AACTCACTTC ACCATGGATT ACGCAGGCAT CACGCGTGGC TCCATCAGAG GCGAGGCCTT 3240
GAAGAAACTC GCAGAATTGA CCATCCAGAA CCAGCCATCC AGCTTGAAAG AAATCAACAC 3300
CGGCATCCAG AAGGACGACT TTGCCAAGTT GTTGTCTGCC ACCCCGAAAA TCCCCACCAA 3360
GCACAAGTTG AACGGCAACC ACGAATTGTC TGAGGTCGCC ATTGCCAAAA AGGAGTACGA 3420
GGTGTTGATT GCCTTGAGCG ACGCCACAAA AGACCCAATC AAAGTGACCT CCCAGATCAA 3480
GATCTTGATT GACAAGTTCA AGGTGTACTT GTTTGAGTTG CCTGACCAGA AGTTCTCCTA 3540
CTCCATCGTG TCCAACTCCG TCAACATCGC CCCCTGGACC TTGCTCGGGG AGAAGTTGAC 3600
CACGGGCTTG ATCAACTTGG CCTTCCAGAA CAACAAGCAG CACTTGGACG AGGTCATTGA 3660
CATCTTCAAC GAGTTCATCG ACAAGTTCTT TGGCAACACG GAGCCGCAAT TGACCAACTT 3720
CTTGACCTTG TGCGGTGTGT TGGACGGGTT GATTGACCAT GCCAACTTCT TGAGCGTGTC 3780
CTCGCGGACC TTCAAGATCT TCTTGAACTT GGACTCGTAT GTGGAC 3826

FIG. 12C

```
TTACAATCAT GGAGCTCGCT AGGAACCCAG ATGTCTGGGA GAAGCTCCGC GAAGAGGTCA    60
ACACGAACTT TGGCATGGAG TCGCCAGACT TGCTCACTTT TGACTCTCTT AGAAGCTCAA   120
AGTACGTTCA GGCGGTGCTC AACGAAACGC TTCGTATCTA CCCGGGGGTG CCACGAAACA   180
TGAAGACAGC TACGTGCAAC ACGACGTTGC CGCGTGGAGG AGGCAAAGAC GGTAAGGAAC   240
CTATTTTGGT GCAGAAGGGC CAGTCCGTTG GGTTGATTAC TATTGCCACG CAGACGGACC   300
CAGAGTATTT TGGGGCAGAT GCTGGTGAGT TCAAACCGGA GAGATGGTTT GATTCAAGCA   360
TGAAGAACTT GGGGTGTAAG TACTTGCCGT TCAATGCTGG GCCCCGGACT TGTTTGGGGC   420
AGCAGTACAC TTTGATTGAA GCGAGCTATT TGCTAGTCAG GTTGGCGCAG ACCTACCGGG   480
TAATCGATTT GCTGCCAGGG TCGGCGTACC CACCAAGAAA GAAGTCGTTG ATCAATATGA   540
GTGCTGCCGA TGGGGTGGTT GTAAAGTTTC ACAAGGATCT AGATGGATAT GTAAGGTGTG   600
TAGGAGGAGC GGAGATAAAT TAGATTTGAT TTTGTGTAAG GTTTAGCACG TCAAGCTACT   660
CCGCACTTTG TGTGTAGGGA GCACATACTC CGTCTGCGCC TGTGCCAAGA GACGGCCCAG   720
GGGTAGTGTG TGGTGGTGGA AGTGCATGTG ACACAATACC CTGGTTCTGG CCAATTGGGG   780
ATTTAGTGTA GGTAAGCTGC GACCTGAAAC ACTCCTCAAC GCTTGAGACA CTGGTGGGTA   840
GAGATGCGGG CCAGGAGGCT ATTCTTGTCG TGCTACCCGT GCACGGAAAA TCGATTGAGG   900
GAAGAACAAA TTTATCCGTG AAATCCACAG AGCGGATAAA TTTGTCACAT TGCTGCGTTG   960
CCCACCCACA GCATTCTCTT TTCTCTCTCT TTGTCTTACT CCGCTCCTGT TTCCTTATCC  1020
AGAAATACAC ACCAACTCAT ATAAAGATAC GCTAGCCCAG CTGTCTTTCT TTTTCTTCAC  1080
TTTTTTTGGT GTGTTGCTTT TTTGGCTGCT ACTTTCTACA ACCACCACCA CCACCACCAC  1140
CATGATTGAA CAAATCCTAG AATATTGGTA TATTGTTGTG CCTGTGTTGT ACATCATCAA  1200
ACAACTCATT GCCTACAGCA AGACTCGCGT CTTGATGAAA CAGTTGGGTG CTGCTCCAAT  1260
CACAAACCAG TTGTACGACA ACGTTTTCGG TATCGTCAAC GGATGGAAGG CTCTCCAGTT  1320
CAAGAAAGAG GGCAGAGCTC AAGAGTACAA CGATCACAAG TTTGACAGCT CCAAGAACCC  1380
AAGCGTCGGC ACCTATGTCA GTATTCTTTT TGGCACCAAG ATTGTCGTGA CCAAGGATCC  1440
AGAGAATATC AAAGCTATTT TGGCAACCCA GTTTGGCGAT TTTTCTTTGG GCAAGAGACA  1500
CGCTCTTTTT AAACCTTTGT TAGGTGATGG GATCTTCACC TTGGACGGCG AAGGCTGGAA  1560
```

FIG. 13A

GCATAGCAGA TCCATGTTAA GACCACAGTT TGCCAGAGAA CAAGTTGCTC ATGTGACGTC 1620
GTTGGAACCA CACTTCCAGT TGTTGAAGAA GCATATCCTT AAACACAAGG GTGAGTACTT 1680
TGATATCCAG GAATTGTTCT TTAGATTTAC TGTCGACTCG GCCACGGAGT TCTTATTTGG 1740
TGAGTCCGTG CACTCCTTAA AGGACGAAAC TATCGGTATC AACCAAGACG ATATAGATTT 1800
TGCTGGTAGA AAGGACTTTG CTGAGTCGTT CAACAAAGCC CAGGAGTATT TGTCTATTAG 1860
AATTTTGGTG CAGACCTTCT ACTGGTTGAT CAACAACAAG GAGTTTAGAG ACTGTACCAA 1920
GCTGGTGCAC AAGTTTACCA ACTACTATGT TCAGAAAGCT TTGGATGCTA CCCCAGAGGA 1980
ACTTGAAAAG CAAGGCGGGT ATGTGTTCTT GTATGAGCTT GTCAAGCAGA CGAGAGACCC 2040
CAAGGTGTTG CGTGACCAGT CTTTGAACAT CTTGTTGGCA GGAAGAGACA CCACTGCTGG 2100
GTTGTTGTCC TTTGCTGTGT TTGAGTTGGC CAGAAACCCA CACATCTGGG CCAAGTTGAG 2160
AGAGGAAATT GAACAGCAGT TTGGTCTTGG AGAAGACTCT CGTGTTGAAG AGATTACCTT 2220
TGAGAGCTTG AAGAGATGTG AGTACTTGAA AGCGTTCCTT AACGAAACCT TGCGTGTTTA 2280
CCCAAGTGTC CCAAGAAACT TCAGAATCGC CACCAAGAAT ACAACATTGC CAAGGGGTGG 2340
TGGTCCAGAC GGTACCCAGC CAATCTTGAT CCAAAAGGGA GAAGGTGTGT CGTATGGTAT 2400
CAACTCTACC CACTTAGATC CTGTCTATTA TGGCCCTGAT GCTGCTGAGT TCAGACCAGA 2460
GAGATGGTTT GAGCCATCAA CCAGAAAGCT CGGCTGGGCT TACTTGCCAT TCAACGGTGG 2520
GCCACGAATC TGTTTGGGTC AGCAGTTTGC CTTGACCGAA GCTGGTTACG TTTTGGTCAG 2580
ATTGGTGCAA GAGTTCTCCC ACATTAGGCT GGACCCAGAT GAAGTGTATC CACCAAAGAG 2640
GTTGACCAAC TTGACCATGT GTTTGCAGGA TGGTGCTATT GTCAAGTTTG ACTAGTACGT 2700
ATGAGTGCGT TTGATTTTGT AGTTTCTGTT TGCAGTAATG AGATAACTAT TCAGATAAGG 2760
CGGGTGGATG TACGTTTTGT AAGAGTTTCC TTACAACCCT GGTGGGTGTG TGAGGTTGCA 2820
TCTTAGGGAG AGATAGCACC TTTTGCAGCT CTCCGTATAC AGTTTTACTC TTTGTAACCT 2880
ATGCCAATCA TGTGGGGATT CATTGTTTGC CCATGGTGGT GCATGCAAAA TCCCCCCAAC 2940
TACCCAATCT CACATGAAAC TCAAGCACAC TAGAAAAAAA AGATGTTGCG TGGGTTCTTT 3000
TGATGTTGGG GAAAACTTTC GTTTCCTTTC TCAGTAATTA AACGTTCTCA CTCAGACAAA 3060
CCACCTGGGC TGCAGACAAC CAGAAAAAAC AAAATCCAGA TAGAAGAAGA AAGGGCTGGA 3120
CAACCATAAA TAAACAACCT AGGGTCCACT CCATCTTTCA CTTCTTCTTC TTCAGACTTA 3180

FIG. 13B

TCTAACAAAC GACTCACTTC ACCATGGATT ACGCAGGTAT CACGCGTGGG TCCATCAGAG 3240

GCGAAGCCTT GAAGAAACTC GCCGAGTTGA CCATCCAGAA CCAGCCATCC AGCTTGAAAG 3300

AAATCAACAC CGGCATCCAG AAGGACGACT TTGCCAAGTT GTTGTCTTCC ACCCCGAAAA 3360

TCCACACCAA GCACAAGTTG AATGGCAACC ACGAATTGTC CGAAGTCGCC ATTGCCAAAA 3420

AGGAGTACGA GGTGTTGATT GCCTTGAGCG ACGCCACGAA AGAACCAATC AAAGTCACCT 3480

CCCAGATCAA GATCTTGATT GACAAGTTCA AGGTGTACTT GTTTGAGTTG CCCGACCAGA 3540

AGTTCTCCTA CTCCATCGTG TCCAACTCCG TTAACATTGC CCCCTGGACC TTGCTCGGTG 3600

AGAAGTTGAC CACGGGCTTG ATCAACTTGG CGTTCCAGAA CAACAAGCAG CACTTGGACG 3660

AAGTCATCGA CATCTTCAAC GAGTTCATCG ACAAGTTCTT TGGCAACACA GAGCCGCAAT 3720

TGACCAACTT CTTGACCTTG TCCGGTGTGT TGGACGGGTT GATTGACCAT GCCAACTTCT 3780

TGAGCGTGTC CTCCAGGACC TTCAAGATCT TCTTGAACTT GGACTCGTTT GTGGACAACT 3840

CGGACTTCTT GAACGACGTG GAGAACTACT CCGACTTTTT GTACGACGAG CCGAACGAGT 3900

ACCAGAACTT 3910

FIG. 13C

```
GAATTCTTTG GATCTAATTC CAGCTGATCT TGCTAATCCT TATCAACGTA GTTGTGATCA     60
TTGTTTGTCT GAATTATACA CACCAGTGGA AGAATATGGT CTAATTTGCA CGTCCCACTG    120
GCATTGTGTG TTTGTGGGGG GGGGGGGGTG CACACATTTT TAGTGCCATT CTTTGTTGAT    180
TACCCCTCCC CCCTATCATT CATTCCCACA GGATTAGTTT TTTCCTCACT GGAATTCGCT    240
GTCCACCTGT CAACCCCCCC CCCCCCCCCC CCCACTGCCC TACCCTGCCC TGCCCTGCAC    300
GTCCTGTGTT TTGTGCTGTG TCTTTCCCAC GCTATAAAAG CCCTGGCGTC CGGCCAAGGT    360
TTTTCCACCC AGCCAAAAAA ACAGTCTAAA AAATTTGGTT GATCCTTTTT GGTTGCAAGG    420
TTTTCCACCA CCACTTCCAC CACCTCAACT ATTCGAACAA AAGATGCTCG ATCAGATCTT    480
ACATTACTGG TACATTGTCT TGCCATTGTT GGCCATTATC AACCAGATCG TGGCTCATGT    540
CAGGACCAAT TATTTGATGA AGAAATTGGG TGCTAAGCCA TTCACACACG TCCAACGTGA    600
CGGGTGGTTG GGCTTCAAAT TCGGCCGTGA ATTCCTCAAA GCAAAAAGTG CTGGGAGACT    660
GGTTGATTTA ATCATCTCCC GTTTCCACGA TAATGAGGAC ACTTTCTCCA GCTATGCTTT    720
TGGCAACCAT GTGGTGTTCA CCAGGGACCC CGAGAATATC AAGGCGCTTT TGGCAACCCA    780
GTTTGGTGAT TTTTCATTGG GCAGCAGGGT CAAGTTCTTC AAACCATTAT TGGGGTACGG    840
TATCTTCACA TTGGACGCCG AAGGCTGGAA GCACAGCAGA GCCATGTTGA GACCACAGTT    900
TGCCAGAGAA CAAGTTGCTC ATGTGACGTC GTTGGAACCA CACTTCCAGT TGTTGAAGAA    960
GCATATCCTT AAACACAAGG GTGAGTACTT TGATATCCAG GAATTGTTCT TTAGATTTAC   1020
TGTCGACTCG GCCACGGAGT TCTTATTTGG TGAGTCCGTG CACTCCTTAA AGGACGAGGA   1080
AATTGGCTAC GACACGAAAG ACATGTCTGA AGAAAGACGC AGATTTGCCG ACGCGTTCAA   1140
CAAGTCGCAA GTCTACGTGG CCACCAGAGT TGCTTTACAG AACTTGTACT GGTTGGTCAA   1200
CAACAAAGAG TTCAAGGAGT GCAATGACAT TGTCCACAAG TTTACCAACT ACTATGTTCA   1260
GAAAGCCTTG GATGCTACCC CAGAGGAACT TGAAAAGCAA GGCGGGTATG TGTTCTTGTA   1320
TGAGCTTGTC AAGCAGACGA GAGACCCCAA GGTGTTGCGT GACCAGTCTT TGAACATCTT   1380
GTTGGCAGGA AGAGACACCA CTGCTGGGTT GTTGTCCTTT GCTGTGTTTG AGTTGGCCAG   1440
AAACCCACAC ATCTGGGCCA AGTTGAGAGA GGAAATTGAA CAGCAGTTTG GTCTTGGAGA   1500
AGACTCTCGT GTTGAAGAGA TTACCTTTGA GAGCTTGAAG AGATGTGAGT ACTTGAAGGC   1560
```

FIG. 14A

CGTGTTGAAC GAAACTTTGA GATTACACCC AAGTGTCCCA AGAAACGCAA GATTTGCGAT 1620
TAAAGACACG ACTTTACCAA GAGGCGGTGG CCCCAACGGC AAGGATCCTA TCTTGATCAG 1680
GAAGGATGAG GTGGTGCAGT ACTCCATCTC GGCAACTCAG ACAAATCCTG CTTATTATGG 1740
CGCCGATGCT GCTGATTTTA GACCGGAAAG ATGGTTTGAA CCATCAACTA GAAACTTGGG 1800
ATGGGCTTTC TTGCCATTCA ACGGTGGTCC AAGAATCTGT TTGGGACAAC AGTTTGCTTT 1860
GACTGAAGCC GGTTACGTTT TGGTTAGACT TGTTCAGGAG TTTCCAAACT TGTCACAAGA 1920
CCCCGAAACC AAGTACCCAC CACCTAGATT GGCACACTTG ACGATGTGCT TGTTTGACGG 1980
TGCACACGTC AAGATGTCAT AGGTTTCCCC ATACAAGTAG TTCAGTAATT ATACACTGTT 2040
TTTACTTTCT CTTCATACCA AATGGACAAA AGTTTTAAGC ATGCCTAACA ACGTGACCGG 2100
ACAATTGTGT CGCACTAGTA TGTAACAATT GTAAAAATAG TGTACACTAA TTTGTGGTGG 2160
CCGGAGATAA ATTACAGTTT GGTTTTGTGT AAACTCGCGG ATATCTCTGG CAGTTTCTCT 2220
TCTCCGCAGC AGCTTTGCCA CGGGTTTGCT CTGGGGCCAA CAAATTCAAA AGGGGGAGAA 2280
ACTTAACACC CCTTATCTCT CCACTCTAGG TTGTAGCTCT TGTGGGGATG CAATTGTCGT 2340
ACGTTTTTTA TGTTTTGTCT AGACTTTGAT GATTACGTTG GATTTCTTAT GTCTGAGGCG 2400
TGCTTGAAAG AAGTGTCAAA ATGTGACAGG CGACGCTATT CGACATGAAC GCGAAAGGGT 2460
TATTTGCATC AATACGAGGG GCTGACTCTA GTCTAGGATG GCAGTCCTAG GTTGCAAACA 2520
TGTTGCACCA TATCCCTCCT GGAGTTGGTC GACCTCGCCT ACGCCACCCT CAGCGATCGG 2580
CACTTTCCGT TGTTCAATAT TTCTCCTTCC CATTGTTCCA GGGGTTATCA ACAACGTTGC 2640
CGGCCTCCTC CCCAAATTAC AAGAAAAATA AATTGTCGCA CGGCACCGAT CTGTCAAAGA 2700
TACAGATAAA CCTTAAATCT GCAAAAACAA GACCCCTCCC CATAGCCTAG AAGCACCAGC 2760
AAGATGATGG AGCAACTCCT CCAGTACTGG TACATCGCAC TCTCTGTATG GTTCATCCTT 2820
CGCTACTTGG CTTCCCACGC ACGAGCCGTC TACTTGCGCC ACAAGCTCGG CGCGGCGCCA 2880
TTCACGCACA CCCAGTACGA CGGCTGGTAT GGGTTCAAGT TTGGGCGGGA GTTTCTCAAG 2940
GCGAAGAAGA TCGGGCGGCA GACGGACTTG GTGCATGCGC GGTTCCGTGG CGGCATGGAC 3000
ACCTTCTCGA GCTACACTTT CGGCATCCAT ATCATCCTTA CCCGGGACCC GGAGAACATC 3060
AAGGCGGTCT TGGCGACGCA GTTCGATGAC TTCTCGCTCG GTGGCAGGAT CAGGTTCTTG 3120
AAGCCGTTGT TGGGGTATGG GATATTCACG 3150

FIG. 14B

```
AAAACCGATA CAAGAAGAAG ACAGTCAACA AGAACGTTAA TGTCAACCAG GCGCCAAGAA     60
GACGGTTTGG CGGACTTGGA AGAATGTGGC ATTTGCCCAT GATGTTTATG TTCTGGAGAG    120
GTTTTTCAAG GAATCGTCAT CCTCCGCCAC CACAAGAACC ACCAGTTAAC GAGATCCATA    180
TTCACAACCC ACCGCAAGGT GACAATGCTC AACAACAACA GCAACAACAA CAACCCCCAC    240
AAGAACAGTG GAATAATGCC AGTCAACAAA GAGTGGTGAC AGACGAGGGA GAAAACGCAA    300
GCAACAGTGG TTCTGATGCA AGATCAGCTA CACCGCTTCA TCAGGAAAAG CAGGAGCTCC    360
CACCACCATA TGCCCATCAC GAGCAACACC AGCAGGTTAG TGTATAGTAG TCTGTAGTTA    420
AGTCAATGCA ATGTACCAAT AAGACTATCC CTTCTTACAA CCAAGTTTTC TGCCGCGCCT    480
GTCTGGCAAC AGATGCTGGC CGACACACTT TCAACTGAGT TTGGTCTAGA ATTCTTGCAC    540
ATGCACGACA AGGAAACTCT TACAAAGACA ACACTTGTGC TCTGATGCCA CTTGATCTTG    600
CTAAGCCTTA TCAACGTAAT TGAGATCATT GTTTGTCTGA ATTATACACA CCAGTGGAAG    660
AATCTGGTCT AATCTGCACG CCTCATGGGC ATTGTGTGTT TTGGGGGGGG GGGGGGGGGT    720
GCACACATTT TTAGTGCGAA TGTTTGTTTG CTGGTTCCCC CTCCCCCCTC CCCCCTATCA    780
TGCCCACAGG ATTAGTTTTT TCCTCACTGG AATTCGCTGT CCACCTGTCA ACCCCCTCAC    840
TGCCCTGCCC TGCCCTGCAC GCCCTGTGTT TTGTGCTGTG GCACTCCCAC GCTATAAAAG    900
CCCTGGCGTA CGGCCAAGGT TTTTCCTCAC AGCCAAAAAA AAATTTGGCT GATCCTTTTG    960
GGCTGCAAGG TTTTTCACCA CCACCACCAC CACCACCTCA ACTATTCAAA CAAAGGATGC   1020
TCGACCAGAT CTTCCATTAC TGGTACATTG TCTTGCCATT GTTGGTCATT ATCAAGCAGA   1080
TCGTGGCTCA TGCCAGGACC AATTATTTGA TGAAGAAGTT GGGCGCTAAG CCATTCACAC   1140
ATGTCCAACT AGACGGGTGG TTTGGCTTCA AATTTGGCCG TGAATTCCTC AAAGCTAAAA   1200
GTGCTGGGAG GCAGGTTGAT TTAATCATCT CCCGTTTCCA CGATAATGAG GACACTTTCT   1260
CCAGCTATGC TTTTGGCAAC CATGTGGTGT TCACCAGGGA CCCCGAGAAT ATCAAGGCGC   1320
TTTTGGCAAC CCAGTTTGGT GATTTTTCAT TGGGAAGCAG GGTCAAATTC TTCAAACCAT   1380
TGTTGGGGTA CGGTATCTTC ACCTTGGACG GCGAAGGCTG GAAGCACAGC AGAGCCATGT   1440
TGAGACCACA GTTTGCCAGA GAGCAAGTTG CTCATGTGAC GTCGTTGGAA CCACATTTCC   1500
AGTTGTTGAA GAAGCATATT CTTAAGCACA AGGGTGAATA CTTTGATATC CAGGAATTGT   1560
```

FIG. 15A

TCTTTAGATT TACCGTTGAT TCAGCGACGG AGTTCTTATT TGGTGAGTCC GTGCACTCCT 1620
TAAGGGACGA GGAAATTGGC TACGATACGA AGGACATGGC TGAAGAAAGA CGCAAATTTG 1680
CCGACGCGTT CAACAAGTCG CAAGTCTATT TGTCCACCAG AGTTGCTTTA CAGACATTGT 1740
ACTGGTTGGT CAACAACAAA GAGTTCAAGG AGTGCAACGA CATTGTCCAC AAGTTCACCA 1800
ACTACTATGT TCAGAAAGCC TTGGATGCTA CCCCAGAGGA ACTTGAAAAA CAAGGCGGGT 1860
ATGTGTTCTT GTACGAGCTT GCCAAGCAGA CGAAAGACCC CAATGTGTTG CGTGACCAGT 1920
CTTTGAACAT CTTGTTGGCT GGAAGGGACA CCACTGCTGG GTTGTTGTCC TTTGCTGTGT 1980
TTGAGTTGGC CAGGAACCCA CACATCTGGG CCAAGTTGAG AGAGGAAATT GAATCACACT 2040
TTGGGCTGGG TGAGGACTCT CGTGTTGAAG AGATTACCTT TGAGAGCTTG AAGAGATGTG 2100
AGTACTTGAA AGCCGTGTTG AACGAAACGT TGAGATTACA CCCAAGTGTC CCAAGAAACG 2160
CAAGATTTGC GATTAAAGAC ACGACTTTAC CAAGAGGCGG TGGCCCCAAC GGCAAGGATC 2220
CTATCTTGAT CAGAAAGAAT GAGGTGGTGC AATACTCCAT CTCGGCAACT CAGACAAATC 2280
CTGCTTATTA TGGCGCCGAT GCTGCTGATT TTAGACCGGA AAGATGGTTT GAGCCATCAA 2340
CTAGAAACTT GGGATGGGCT TACTTGCCAT TCAACGGTGG TCCAAGAATC TGCTTGGGAC 2400
AACAGTTTGC TTTGACCGAA GCCGGTTACG TTTTGGTTAG ACTTGTTCAG GAATTCCCTA 2460
GCTTGTCACA GGACCCCGAA ACTGAGTACC CACCACCTAG ATTGGCACAC TTGACGATGT 2520
GCTTGTTTGA CGGGGCATAC GTCAAGATGC AATAGGTTTT GGTTTGACTT TGTTTCCATA 2580
TGCAAGTAGT TCAGTAATTA CACACTAATT TGTGGTGGCC GGCGATAAAT TACCGTTTGG 2640
TTTTGTGTAA AAATTCGGAC ATCTCTGGTG GTTTCCCTTC TCCGCAGCAG CTTTGCCACG 2700
GGTTTGCTCT GCGGCCAACA AATTCGAAAG GGGGGGGGGG GGGGGAGAAA GTTAACACCC 2760
CCTGTTCCCA CCGTAGGCTG TAGCTCTTGT GGGGGGATGT AATTGTCGTA CGTTTTCATG 2820
TTTGGCCCAG ACTTTGATGA TTACGTAGGC TTTCTTATGT CTAAGGCGTG CTTGACACAA 2880
GTGTCAAAAG GTGACAGGCG ACGTTATTCG ACATGAACGC AAAAGGGTAA TTTGCATCGA 2940
TACGAGGGGT TGCCTCTGGT CTAAGAAGGA CCCCCCAGGT TGCAAACATG TTGCACTGCA 3000
TCCCACTCAG AGTTGGTCGA CCACGCCTAC GCTTACCCTC AGCGATCGGC ACTTTCCGTT 3060
GCTCAATATT TCTCTCCCCC CTGCTTCCCC CCATTGTTCC AGGGATTATC AACAACGTTG 3120
CCGGTCTCCT CTCCCCCCCC TCCCCCCAGT TATGTACAAG AAAATTAAAT TGTCGCACGG 3180

FIG. 15B

CACCGATACG TCAAAGATAC AGAGAAACCT TAATCCCTCC CATAGCCTAG AAGCATCAAA 3240
AAGATGATTG AGCAACTCCT CCAGTACTGG TACATTGCAC TCCCTGTATG GTTCATTCTC 3300
CGCTACGTGG CTTCCCACGC ACGAACCATC TACTTGCGCC ACAAGCTCGG CGCGGCGCCG 3360
TTCACGCACA CCCAGTACGA CGGATGGTAT GGGTTCAAGT TTGGGCGGGA GTTTCTCAAG 3420
GCGAAGAAGA TTGGAAGGCA GACGGACTTG GTGCATGCGC GGTTCCGTGG AGGGGGCATG 3480
GATACTTTCT CGAGCTATAC TTTCGGCATC CATATCATTC TTACTCGGGA CCCGGAGAAC 3540
ATCAAGGCGG TCTTGGCGAC GCAGTTCGAT GACTTTTCG 3579

FIG. 15C 1 gram (g) Whole fermentation broth (70°C)

+

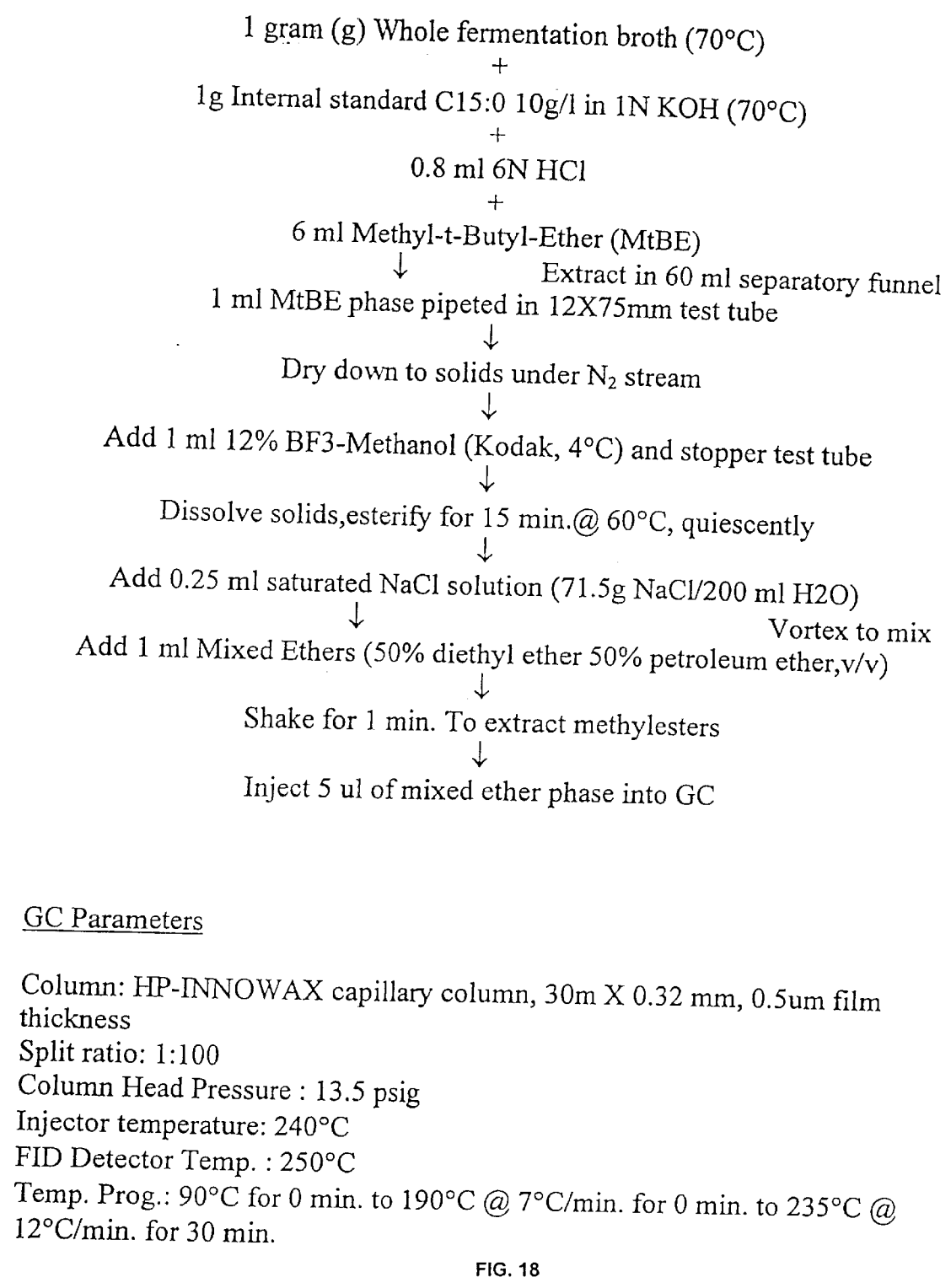

1g Internal standard C15:0 10g/l in 1N KOH (70°C)

+

0.8 ml 6N HCl

+

6 ml Methyl-t-Butyl-Ether (MtBE)

↓ Extract in 60 ml separatory funnel 1 ml MtBE phase pipeted in 12X75mm test tube

↓

Dry down to solids under $N_2$ stream

↓

Add 1 ml 12% BF3-Methanol (Kodak, 4°C) and stopper test tube

↓

Dissolve solids,esterify for 15 min.@ 60°C, quiescently

↓

Add 0.25 ml saturated NaCl solution (71.5g NaCl/200 ml H2O)

↓ Vortex to mix

Add 1 ml Mixed Ethers (50% diethyl ether 50% petroleum ether,v/v)

↓

Shake for 1 min. To extract methylesters

↓

Inject 5 ul of mixed ether phase into GC

GC Parameters

Column: HP-INNOWAX capillary column, 30m X 0.32 mm, 0.5um film thickness
Split ratio: 1:100
Column Head Pressure : 13.5 psig
Injector temperature: 240°C
FID Detector Temp. : 250°C
Temp. Prog.: 90°C for 0 min. to 190°C @ 7°C/min. for 0 min. to 235°C @ 12°C/min. for 30 min.

FIG. 18

3908 nucleotides

LacZα fragment: bases 1-571
M13 reverse priming site: bases 205-221
Multiple cloning site: bases 234-357
T7 promoter/priming site: bases 364-383
M13 Forward (-20) priming site: bases 391-406
M13 Forward (-40) priming site: bases 411-426
f1 origin: bases 548-962
Kanamycin resistance ORF: bases 1296-2090
Ampicillin resistance ORF: bases 2108-2968
ColE1 origin: bases 3113-3786

Sequence Range: 1 to 1712

```
        10         20         30         40         50         60         70         80         90        100
GGTACCGAGC TCACGAGTTT TGGGATTTTC GAGTTTGGAT TGTTTCCTTT GTTGATTGAA TTGACGAAAC CAGAGGTTTT CAAGACAGAT AAGATTGGGT
       110        120        130        140        150        160        170        180        190        200
TTATCAAAAC GCAGTTTGAA ATATTCCAGT TGGTTTCCAA GATATCTTGA AGAAGATTGA CGATTTGAAA TTTGAAGAAG TGGAGAAGAT CTGGTTTGGA
       210        220        230        240        250        260        270        280        290        300
TTGTTGGAGA ATTTCAAGAA TCTCAAGATT TACTCTAACG ACGGGTACAA CGAGAATTGT ATTGAATTGA TCAAGAACAT GATCTTGGTG TTACAGAACA
       310        320        330        340        350        360        370        380        390        400
TCAAGTTCTT GGACCAGACT GAGAATGCCA CAGATATACA AGGCGTCATG TGATAAAATG GATGAGATTT ATCCCACAAT TGAAGAAAGA GTTTATGGAA
       410        420        430        440        450        460        470        480        490        500
AGTGGTCAAC CAGAAGCTAA ACAGGAAGAA GCAAACGAAG AGGTGAAACA AGAAGAAGAA GGTAAATAAG TATTTTGTAT TATATAACAA ACAAAGTAAG
       510        520        530        540        550        560        570        580        590        600
GAATACAGAT TTATACAATA AATTGCCATA CTAGTCACGT GAGATATCTC ATCCATTCCC CAACTCCCAA GAAAAAAAAA AAGTGAAAAA AAAAATCAAA
       610        620        630        640        650        660        670        680        690        700
CCCAAAGATC AACCTCCCCA TCATCATCGT CATCAAACCC CCAGCTCAAT TCGCAATGGT TAGCACAAAA ACATACACAG AAAGGGCATC AGCACACCCC
       710        720        730        740        750        760        770        780        790        800
TCCAAGGTTG CCCAACGTTT ATTCCGCTTA ATGGAGTCCA AAAAGACCAA CCTCTGCGCC TCGATCGACG TGACCACAAC CGCCGAGTTC CTTTCGCTCA
       810        820        830        840        850        860        870        880        890        900
TCGACAAGCT CGGTCCCCAC ATCTGTCTCG TGAAGACGCA CATCGATATC ATCTCAGACT TCAGCTACGA GGGCACGATT GAGCCGTTGC TTGTGCTTGC
       910        920        930        940        950        960        970        980        990       1000
AGAGCGCCAC GGGTTCTTGA TATTCGAGGA CAGGAAGTTT GCTGATATCG GAAACACCGT GATGTTGCAG TACACCTCGG GGGTATACCG GATCGCGGCG
      1010       1020       1030       1040       1050       1060       1070       1080       1090       1100
TGGAGTGACA TCACGAACGC GCACGGAGTG ACTGGGAAGG GCGTCGTTGA AGGGTTGAAA CGCGGTGCGG AGGGGGTAGA AAAGGAAAGG GGCGTGTTGA
      1110       1120       1130       1140       1150       1160       1170       1180       1190       1200
TGTTGGCGGA GTTGTCGAGT AAAGGCTCGT TGGCGCATGG TGAATATACC CGTGAGACGA TCGAGATTGC GAAGAGTGAT CGGGAGTTCG TGATTGGGTT
      1210       1220       1230       1240       1250       1260       1270       1280       1290       1300
CATCGCGCAG CGGGACATGG GGGGTAGAGA AGAAGGGTTT GATTGGATCA TCATGACGCC TGGTGTGGGG TTGGATGATA AAGGCGATGC GTTGGGCCAG
      1310       1320       1330       1340       1350       1360       1370       1380       1390       1400
CAGTATAGGA CTGTTGATGA GGTGGTTCTG ACTGGTACCG ATGTGATTAT TGTCGGGAGA GGGTTGTTTG GAAAAGGAAG AGACCCTGAG GTGGAGGGAA
      1410       1420       1430       1440       1450       1460       1470       1480       1490       1500
AGAGATACAG GGATGCTGGA TGGAAGGCAT ACTTGAAGAG AACTGGTCAG TTAGAATAAA TATTGTAATA AATAGGTCTA TATACATACA CTAAGCTTCT
      1510       1520       1530       1540       1550       1560       1570       1580       1590       1600
AGGACGTCAT TGTAGTCTTC GAAGTTGTCT GCTAGTTTAG TTCTCATGAT TTCGAAAACC AATAACGCAA TGGATGTAGC AGGGATGGTG GTTAGTGCGT
      1610       1620       1630       1640       1650       1660       1670       1680       1690       1700
TCCTGACAAA CCCAGAGTAC GCCGCCTCAA ACCACGTCAC ATTCGCCCTT TGCTTCATCC GCATCACTTG CTTGAAGGTA TCCACGTACG AGTTGTAATA
      1710
CACCTTGAAG AA
```

FIG. 28

CYTOCHROME B5 GENE AND PROTEIN OF *CANDIDA TROPICALIS* AND METHODS RELATING THERETO

CROSS REFERENCE TO RELATED APPLICATIONS

This application claims priority to U.S. Provisional Application Ser. No. 60/220,958 filed Jul. 26, 2000, the contents of which are hereby incorporated by reference.

STATEMENT REGARDING FEDERALLY SPONSORED RESEARCH OR DEVELOPMENT

This invention was funded, at least in part, under grants from the Department of Commerce, NIST-ATP Cooperative Agreement Number 70NANB8H4033 and the Department of Energy No. DE-FC36-95GO10099. The Government may therefore have certain rights in the invention.

BACKGROUND

1. Field of the Invention

This invention relates to processes and compositions involved in dicarboxylic acid production in yeast. More particularly, the invention relates to a novel gene which encodes a cytochrome b5 protein in *Candida tropicalis.*

2. Description of Related Art

Aliphatic dioic acids are versatile chemical intermediates useful as raw materials for the preparation of perfumes, polymers, adhesives and macrolid antibiotics. While several chemical routes to the synthesis of long-chain α, ω-dicarboxylic acids are available, the synthesis is not easy and most methods result in mixtures containing shorter chain lengths. As a result, extensive purification steps are necessary. While it is known that long-chain dioic acids can also be produced by microbial transformation of alkanes, fatty acids or esters thereof, chemical synthesis has remained the most commercially viable route, due to limitations with the current biological approaches.

Several strains of yeast are known to excrete α, ω-dicarboxylic acids as a byproduct when cultured on alkanes or fatty acids as the carbon source. In particular, yeast belonging to the Genus Candida, such as *C. albicans, C. cloacae, C. guillermondii, C. intermedia, C. lipolytica, C. maltosa, C. parapsilosis* and *C. zeylenoides* are known to produce such dicarboxylic acids (*Agr. Biol. Chem.* 35: 2033–2042 (1971)). Also, various strains of *C. tropicalis* are known to produce dicarboxylic acids ranging in chain lengths from $C_{11}$ through $C_{18}$ (Okino et al., B M Lawrence, B D Mookherjee and B J Willis (eds), in *Flavors and Fragrances: A World Perspective.* Proceedings of the $10^{th}$ International Conference of Essential Oils, Flavors and Fragrances, Elsevier Science Publishers BV Amsterdam (1988)), and are the basis of several patents as reviewed by Bühler and Schindler, in *Aliphatic Hydrocarbons in Biotechnology,* H. J. Rehm and G. Reed (eds), Vol. 169, Verlag Chemie, Weinheim (1984).

Studies of the biochemical processes by which yeasts metabolize alkanes and fatty acids have revealed three types of oxidation reactions: α-oxidation of alkanes to alcohols, (ω-oxidation of fatty acids to α, ω-dicarboxylic acids and the degradative β-oxidation of fatty acids to $CO_2$ and water. The first two types of oxidations are catalyzed by microsomal enzymes while the last type takes place in the peroxisomes. In *C. tropicalis,* the first step in the ω-oxidation pathway is catalyzed by a membrane-bound enzyme complex (ω-hydroxylase complex) including a cytochrome P450 monooxygenase and a NADPH cytochrome reductase. This hydroxylase complex is responsible for the primary oxidation of the terminal methyl group in alkanes and fatty acids as described, e.g., in Gilewicz et al., *Can. J. Microbiol.* 25:201 (1979), incorporated herein by reference. The genes which encode the cytochrome P450 and NADPH reductase components of the complex have previously been identified as P450ALK and P450RED respectively, and have also been cloned and sequenced as described, e.g., in Sanglard et al., *Gene* 76:121–136 (1989), incorporated herein by reference. P450ALK has also been designated P450ALK1. More recently, ALK genes have been designated by the symbol CYP and RED genes have been designated by the symbol CPR. See, e.g., Nelson, *Pharmacogenetics* 6(1):1–42 (1996), which is incorporated herein by reference. See also Ohkuma et al., *DNA and Cell Biology* 14:163–173 (1995), Seghezzi et al., *DNA and Cell Biology,* 11:767–780 (1992) and Kargel et al., *Yeast* 12:333–348 (1996), each incorporated herein by reference. For example, P450ALK is also designated CYP52 according to the nomenclature of Nelson, supra. Fatty acids are ultimately formed from alkanes after two additional oxidation steps, catalyzed by alcohol oxidase as described, e.g., in Kemp et al., *Appl. Microbiol. and Biotechnol.* 28: 370–374 (1988), incorporated herein by reference, and aldehyde dehydrogenase. The fatty acids can be further oxidized through the same or similar pathway to the corresponding dicarboxylic acid. The ω-oxidation of fatty acids proceeds via the ω-hydroxy fatty acid and its aldehyde derivative, to the corresponding dicarboxylic acid without the requirement for CoA activation. However, both fatty acids and dicarboxylic acids can be degraded, after activation to the corresponding acyl-CoA ester through the β-oxidation pathway in the peroxisomes, leading to chain shortening. In mammalian systems, both fatty acid and dicarboxylic acid products of ω-oxidation are activated to their CoA-esters at equal rates and are substrates for both mitochondrial and peroxisomal β-oxidation (*J. Biochem.,* 102:225–234 (1987)). In yeast, β-oxidation takes place solely in the peroxisomes (*Agr. Biol. Chem.* 49:1821–1828 (1985)).

The production of dicarboxylic acids by fermentation of unsaturated $C_{14}$–$C_{16}$ monocarboxylic acids using a strain of the species *C. tropicalis* is disclosed in U.S. Pat. No. 4,474,882. The unsaturated dicarboxylic acids correspond to the starting materials in the number and position of the double bonds. Similar processes in which other special microorganisms are used are described in U.S. Pat. Nos. 3,975,234 and 4,339,536, in British Patent Specification 1,405,026 and in German Patent Publications 21 64 626, 28 53 847, 29 37 292, 29 51 177, and 21 40 133.

Cytochrome P450 monooxygenases (P450s) are terminal monooxidases of a multicomponent enzyme system including P450 and CPR. In some instances, a second electron carrier, cytochrome b5(CYTb5) and its associated reductase are involved as described below and in Morgan, et al., *Drug Metab. Disp.* 12:358–364, 1984. The P450s comprise a superfamily of proteins which exist widely in nature having been isolated from a variety of organisms as described e.g., in Nelson, supra. These organisms include various mammals, fish, invertebrates, plants, mollusk, crustaceans, lower eukaryotes and bacteria (Nelson, supra). First discovered in rodent liver microsomes as a carbon-monoxide binding pigment as described, e.g., in Garfinkel, *Arch. Biochem. Biophys.* 77:493–509 (1958), which is incorporated herein by reference, P450s were later named based on their absorption at 450 nm in a reduced-CO coupled difference spectrum as described, e.g., in Omura et al., *J. Biol. Chem.* 239:2370–2378 (1964), which is incorporated herein by reference.

P450s catalyze the metabolism of a variety of endogenous and exogenous compounds as described, e.g., in Nelson, supra, and Nebert et al., *DNA Cell. Biol.* 10:1–14 (1991), which is incorporated herein by reference. Endogenous compounds include steroids, prostanoids, eicosanoids, fat-soluble vitamins, fatty acids, mammalian alkaloids, leukotrines, biogenic amines and phytolexins (Nelson, supra, and Nebert et al., supra). P450 metabolism involves such reactions as epoxidation, hydroxylation, dealkylation, hydroxylation, sulfoxidation, desulfuration and reductive dehalogenation. These reactions generally make the compound more water soluble, which is conducive for excretion, and more electrophilic. These electrophilic products can have detrimental effects if they react with DNA or other cellular constituents. However, they can react through conjugation with low molecular weight hydrophilic substances resulting in glucoronidation, sulfation, acetylation, amino acid conjugation or glutathione conjugation typically leading to inactivation and elimination as described, e.g., in Klaassen et al., *Toxicology,* $3^{rd}$ ed, Macmillan, New York, 1986, incorporated herein by reference.

P450s are heme thiolate proteins consisting of a heme moiety bound to a single polypeptide chain of 45,000 to 55,000 Da. The iron of the heme prosthetic group is located at the center of a protoporphyrin ring. Four ligands of the heme iron can be attributed to the porphyrin ring. The fifth ligand is a thiolate anion from a cysteinyl residue of the polypeptide. The sixth ligand is probably a hydroxyl group from an amino acid residue, or a moiety with a similar field strength such as a water molecule as described, e.g., in Goeptar et al., *Critical Reviews in Toxicology* 25(1):25–65 (1995), incorporated herein by reference.

Monooxygenation reactions catalyzed by cytochromes P450 in a eukaryotic membrane-bound system require the transfer of electrons from NADPH to P450 via NADPH-cytochrome P450 reductase (CPR) as described, e.g., in Taniguchi et al., *Arch. Biochem. Biophys.* 232:585 (1984), incorporated herein by reference. CPR genes are now also referred to as NCP genes. See, e.g., Debacker et al., *Antimicrobial Agents and Chemotherapy,* 45:1660 (2001). CPR is a flavoprotein of approximately 78,000 Da containing 1 mol of flavin adenine dinucleotide (FAD) and 1 mol of flavin mononucleotide (FMN) per mole of enzyme as described, e.g., in Potter et al., *J. Biol. Chem.* 258:6906 (1983), incorporated herein by reference. The FAD moiety of CPR is the site of electron entry into the enzyme, whereas FMN is the electron-donating site to P450 as described, e.g., in Vermilion et al., *J. Biol. Chem.* 253:8812 (1978), incorporated herein by reference. The overall reaction is as follows:

$$H^{+}+RH+NADPH+O_{2}\rightarrow ROH+NADP^{+}+H_{2}O$$

Binding of a substrate to the catalytic site of P450 apparently results in a conformational change initiating electron transfer from CPR to P450. Subsequent to the transfer of the first electron, $O_2$ binds to the $Fe_2^{+}$-P450 substrate complex to form $Fe_3^{+}$-P450-substrate complex. This complex is then reduced by a second electron from CPR, or, in some cases, NADH via a second electron carrier, cytochrome b5 (CYTb5) and its associated NADH-cytochrome b5 reductase as described, e.g., in Guengerich et al., *Arch. Biochem. Biophys.* 205:365 (1980), incorporated herein by reference, and Morgan, supra. Most of the aforementioned studies implicate CYTb5 as being involved in the pathway only for the transfer of the second electron. One atom of this reactive oxygen is introduced into the substrate, while the other is reduced to water. The oxygenated substrate then dissociates, regenerating the oxidized form of the cytochrome P450 as described, e.g., in Klassen, Amdur and Doull, *Casarett and Doull's Toxicology,* Macmillan, New York (1986), incorporated herein by reference.

With respect to the CYTb5, several other models of the role of this protein in P450 expression have been proposed besides its role as an electron carrier. Another model of the role of CYTb5 in P450 expression is based upon effects of protein-protein interactions as described, e.g., in Tamburini et al., *Proc. Natl. Acad Sci.,* 84:11–15 (1986), incorporated herein by reference. By this model, CYTb5 binding with P450 results in a complex with increased high spin content. This complex then has a higher affinity for CPR. Through this interaction, CYTb5 does not actually provide the second electron, but decreases the time between first and second electron transfer. These conclusions were made based on work with rabbit CYP2B4. In addition, CYTb5 did not prevent interaction of rabbit CYP2B4 with CPR; therefore, it was proposed that the P450 binding domains for CYTb5 and CPR were different. This could possibly explain why only certain P450 interact with CYTb5. It is known that CYTb5 can be reduced by cytochrome b5 reductase or CPR as described, e.g., in Enoch et al., *J. Bio. Chem,* 254:8976–8981, (1979), incorporated herein by reference. However, in at least one interesting case, cytochrome b5 reductase addition to a reconstituted system containing CYTb5 did not result in increased substrate oxidation as described, e.g., in Sugiyama et al., *J. Biochem.,* 87:1457–1467, (1979), incorporated herein by reference.

Various other studies have also indicated that CYTb5 may regulate phosphorylation of cytochrome P450's by inhibiting cytochrome P450 phosphorylation by various protein kinases, e.g., cAMP dependent protein kinase and protein kinase C as described, e.g., in Jansson et al., *Arch. Biochem. Biophys.* 259:441–448 (1987), Epstein et al., *Arch. Biochem. Biophys.* 271(2):424–432(1989) and Lobanov et al., *Biokhimiia* 58(10):1529–1537 (1993).

Regardless of the mechanism, numerous studies indicate that CYTb5's involvement is advantageous in some P450 mediated reactions. An obligatory role of CYTb5 has been shown in several reconstituted P450 systems as described, e.g., in Sugiyama et al., supra, Sugiyama et al. *Biochem. and Biophys. Res. Comm.,* 90:715–720 (1979), Canova-Davis et al., *J. Bio. Chem.* 259:2541–2546, 1983, Kuwahara et al., *Biochem. and Biophys. Res. Comm.,* 96:1562–1568 (1980), and Sasame et al., *Life Sciences* 14:35–46 (1974), each incorporated herein by reference. In all these cases, activity was abolished either upon omission of the exogenously added CYTb5 or its inactivation by the addition of CYTb5 antibody. As noted above, CYTb5 is also involved in the pathway for the second electron in certain P450 mediated reactions as described, e.g., in Hrycay et al., *Archv. Bioch.* 165:331–339 (1974), Imai et al., *Biochem. and Biophys. Res. Comm.* 75:420–426 (1977), and Imai, *J. Biochem.* 89:351–362 (1980), each incorporated herein by reference, as well as the reduction of oxy-cytochrome P450 to the active oxygen complex as described, e.g., in Noshiro et al., *J. Biochem.* 116:521–526 (1981), incorporated herein by reference.

In other studies using reconstituted systems, exogenously added CYTb5 increased the activities of rabbit CYP2B4 as described, e.g., in Sugiyama et al., *J. Biochem.,* 92:1793–1803 (1982), and Chiang, *Archv. Bioch. Biophy.,* 211:662–673 (1981), rabbit CYP1A2 as described, e.g., in Vatsis et al., *J. Biol. Chem.* 257:11221–11229 (1982), dog CYP2B11 and rat CYP2B1 as described, e.g., in Duignan et al., *Arch. Bioch. Biophy.* 267:294–304 (1988), and a rat P450 chlorobenzene hydroxylation reaction as described, e.g., in Lu et al., *Biochem. and Biophys. Res. Comm.* 61:1348:1355 (1974), each incorporated herein by reference.

CYP51, lanosterol 14α demethylase, performs an essential reaction in the biosynthesis of ergosterol, the major membrane sterol of *Saccharomyces cerevisiae (Sc) as described, e.g., in Parks, CRC Crit. Rev. Microbiol.,* 6:301–341 (1978), incorporated herein by reference. Sc strains that synthesize ergosterol do not utilize exogenous ergosterol, but those that are blocked in pre-sterol steps or in heme biosynthesis can take up and use exogenous ergosterol as described, e.g., in Parks, supra. Anaerobically grown Sc cannot synthesize sterols but do utilize exogenous ergosterol. Disruption of CYP51 produces Sc strains which continue to produce 14α-methyl sterols, produce no detectable ergosterol and are incapable of aerobic growth as described, e.g., in Kalb et al., *DNA,* 6:529–537 (1987), incorporated herein by reference. Rather they are obligate anaerobes, a condition where they do accumulate exogenous ergosterol.

CPR functions as the electron donor for this demethylase reaction as described, e.g., in Aoyama et al., *J. Biol. Chem.* 259:1661–1666 (1984), incorporated herein by reference. If CPR is the sole donor of electrons to CYP51 in Sc, CPR null mutants (cpr1) should phenotypically resemble the disrupted CYP51 strains (cyp51). However, a Sc cpr1 null mutant was not obligately anaerobic, and produced ergosterol as described, e.g., in Sutter and Loper, *Biochem. and Biophys. Res. Comm.,* 160:1257–1266 (1989), incorporated herein by reference. The production of ergosterol shows that some CYP51 is still functional. The gene responsible for this recovery of a cpr1 null mutant was shown to be that encoding CYTb5, showing that in this system, CYTb5 is able to functionally mimic CPR when present in high copy number as described, e.g., in Truan et al., *Gene,* 142(1):123–7 (1994), incorporated herein by reference.

The expression of mammalian P450s in Sc has been accomplished with varied results as described, e.g., in Renaud et al., *J. Biochem.* 194:889–896 (1990), Urban et al., *Biochimie* 72:463–472 (1990), and Pompon et al., *Molecular Endocrinology* 3:1477–1487 (1989), each incorporated herein by reference. Studies have shown that activity by various mammalian P450s expressed in Sc has been enhanced upon addition of rabbit CYTb5 to isolated microsomes from these strains. Specifically, Sc microsomal human CYP3A4 and mouse Cyp1a-1 activity increased upon rabbit CYTb5 addition as described, e.g., in Renaud et al., supra, and Urban et al., supra.

In addition to its positive effects, one study involving Sc suggests CYTb5 may act negatively as described, e.g., in Pompon et al., supra. Addition of rabbit CYTb5 to isolated microsomes from a Sc expressing human CYP19 resulted in a decrease in aromatase activity.

Short chain (≦C12) aliphatic dicarboxylic acids (diacids) are important industrial intermediates in the manufacture of diesters and polymers, and find application as thermoplastics, plasticizing agents, lubricants, hydraulic fluids, agricultural chemicals, pharmaceuticals, dyes, surfactants, and adhesives. The high price and limited availability of short chain diacids are due to constraints imposed by the existing chemical synthesis.

Long-chain-diacids (aliphatic α, ω-dicarboxylic acids with carbon numbers of 12 or greater, hereafter also referred to as diacids) ($HOOC—(CH_2)_n—COOH$) are a versatile family of chemicals with demonstrated and potential utility in a variety of chemical products including plastics, adhesives, and fragrances. Unfortunately, the full market potential of diacids has not been realized because chemical processes produce only a limited range of these materials at a relatively high price. In addition, chemical processes for the production of diacids have a number of limitations and disadvantages. All the chemical processes are restricted to the production of diacids of specific carbon chain lengths. For example, the dodecanedioic acid process starts with butadiene. The resulting product diacids are limited to multiples of four-carbon lengths and, in practice, only dodecanedioic acid is made. The dodecanedioic process is based on nonrenewable petrochemical feedstocks. The multireaction conversion process produces unwanted byproducts, which result in yield losses, $NO_x$ pollution and heavy metal wastes.

Long-chain diacids offer potential advantages over shorter chain diacids, but their high selling price and limited commercial availability prevent widespread growth in many of these applications. Biocatalysis offers an innovative way to overcome these limitations with a process that produces a wide range of diacid products from renewable feedstocks. However, there is no commercially viable bioprocess to produce long chain diacids from renewable resources.

SUMMARY OF THE INVENTION

In accordance with the present invention, isolated nucleic acid encoding the CYTb5 protein (SEQ. ID. NO. 2) is provided. Also provided is an isolated CYTb5 protein including the amino acid sequence shown in SEQ. ID. NO. 2. Further provided is an expression vector including nucleic acid encoding the CYTb5 protein (SEQ. ID. NO. 2). Also provided is a host cell transformed with an expression vector comprising nucleic acid encoding the CYTb5 protein (SEQ. ID. NO. 2).

A method is provided of producing a CYTb5 protein including the amino acid sequence set forth in SEQ. ID. NO. 2 which includes transforming a host cell with a nucleic acid sequence that encodes the CYTb5 protein and culturing the cell in an appropriate medium.

A method of increasing the production of dicarboxylic acid is provided which includes providing a host cell having a naturally occurring number of CYTb5 genes; increasing, in the host cell, the number CYTb5 genes which encode a CYTb5 protein having the amino acid sequence set forth in SEQ. ID. NO. 2; and culturing the host cell in media containing an organic substrate which upregulates the CYTb5 gene, to effect increased production of dicarboxylic acid.

BRIEF DESCRIPTION OF THE DRAWINGS

FIGS. 1A–1C depict the nucleotide sequence of the CYTb5 gene (SEQ. ID. NO. 1) and the amino acid sequence of the CYTb5 protein (SEQ. ID. NO. 2).

FIGS. 2A–2B depict the nucleotide sequence of the CPRA gene (SEQ. ID. NO. 3).

FIGS. 3A–3C depict the amino acid sequence of the CPRA protein (SEQ. ID. NO. 4).

FIGS. 4A–4B depict the nucleotide sequence of the CPRB gene (SEQ. ID. NO. 5).

FIGS. 5A–5C depict the amino acid sequence of the CPRB protein (SEQ. ID. NO. 6).

FIGS. 6A–6C depict the nucleotide sequence of the CYP52A1A gene (SEQ. ID. NO. 7).

FIGS. 7A–7B depict the nucleotide sequence of the CYP52A2A gene (SEQ. ID. NO. 8).

FIGS. 8A–8C depict the nucleotide sequence of the CYP52A2B gene (SEQ. ID. NO. 9).

FIGS. 9A–9C depict the nucleotide sequence of the CYP52A3A gene (SEQ. ID. NO. 10).

FIGS. 10A–10C depict the nucleotide sequence of the CYP52A3B gene (SEQ. ID. NO. 11).

FIGS. 11A–11C depict the nucleotide sequence of the CYP52D4A gene (SEQ. ID. NO. 12).

FIGS. 12A–12C depict the nucleotide sequence of the CYP52A5A gene (SEQ. ID. NO. 13).

FIGS. 13A–13C depict the nucleotide sequence of the CYP52A5B gene (SEQ. ID. NO. 14).

FIGS. 14A–14B depict the nucleotide sequence of the CYP52A8A gene (SEQ. ID. NO. 15).

FIGS. 15A–15C depict the nucleotide sequence of the CYP52A8B gene (SEQ. ID. NO. 16).

FIG. 18 is a schematic depiction of a procedure for extracting and analyzing diacids and monoacids from fermentation broths.

FIG. 28 depicts the nucleotide sequence of the URA3A gene. (SEQ. ID. NO. 45).

DESCRIPTION OF THE PREFERRED EMBODIMENTS

Figure 16:
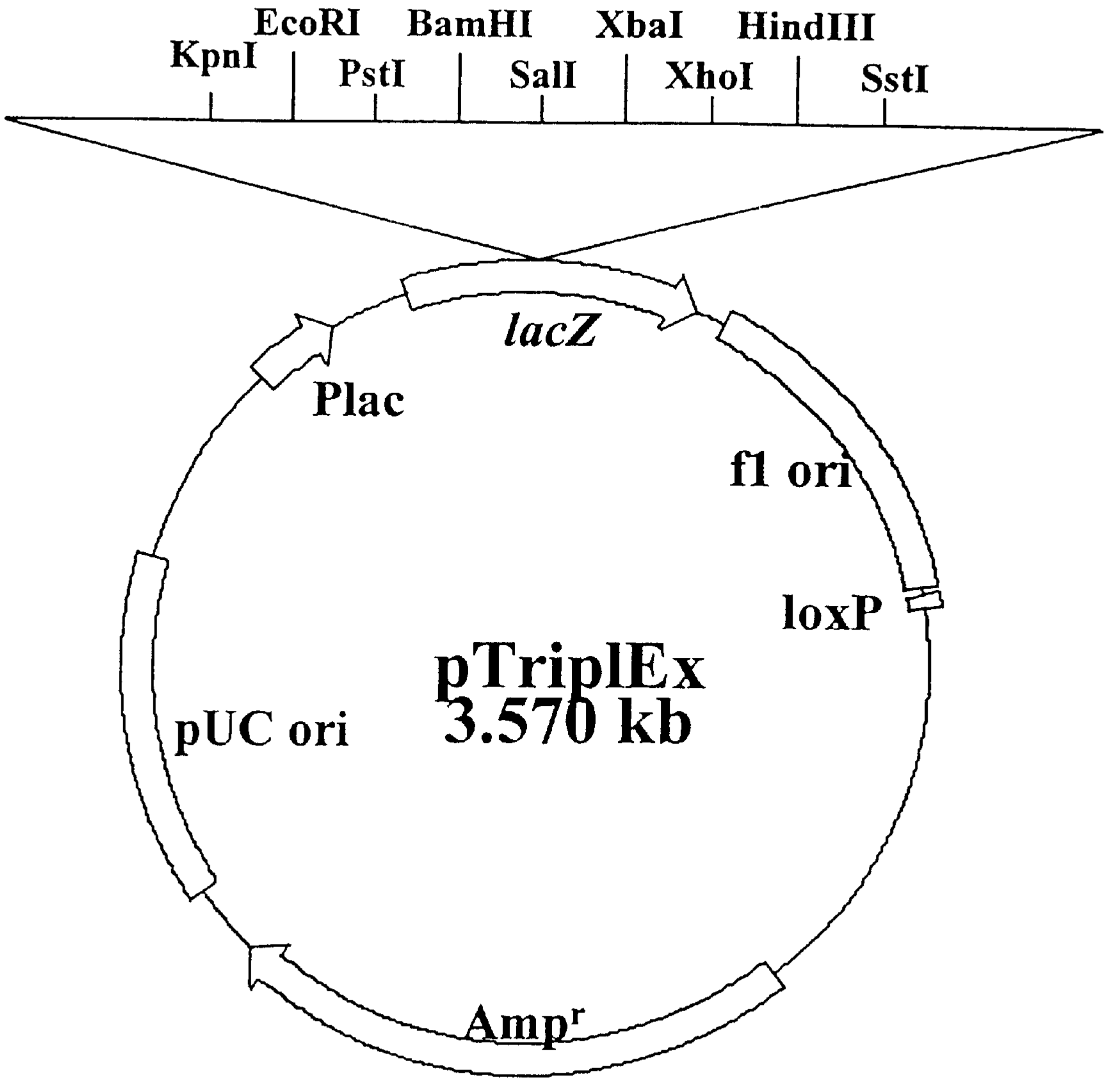
FIG. 16 is a schematic representation of cloning vector pTriplEx available from Clontech™ Laboratories, Inc. Selected restriction sites within the multiple cloning site are shown.

Diacid productivity is improved according to the present invention by selectively increasing a protein which is important to the oxidation of organic substrates such as fatty acids composing the desired feed. According to the present invention, a unique CYTb5 gene of C. tropicalis 20336 has been identified and characterized that is involved in P450 reactions.

The nucleotide sequence (2710 bp) of the full length CYTb5 gene includes a regulatory region and a protein coding region defined by nucleotides 1109–1495 as shown in FIGS. 1A–1C. The amino acid sequence (129 amino acids) of the CYTb5 protein is also shown in FIGS. 1A–1C.

Amplification of the CYTb5 gene in host cells, e.g., yeast, which excrete dicarboxylic acids, particularly α, ω-dicarboxylic acids, as a by-product when cultured on alkane or fatty acid substrates, produces a greater yield of dicarboxylic acids. Expression of the CYTb5 gene of C. tropicalis and its induction by alkanes or fatty acids can be measured in cells isolated during the course of fermentation bioconversions using the quantitative competitive reverse transcription polymerase chain reaction (QC-RT-PCR) assay as described below (see Examples 11 and 14).

In addition, modification of existing promoters and/or the isolation of alternative promoters provides increased expression of the CYTb5 gene. Strong promoters are obtained from at least four sources: random or specific modifications of the CYTb5 promoter, the selection of a strong promoter from available Candida β-oxidation genes such as POX4 and POX5, or screening to select another suitable Candida promoter.

Promoter strength is measured using QT-RT-PCR to measure CYTb5 gene expression in yeast, e.g., Candida cells, isolated from fermentors. Enzymatic assays and antibodies specific for CYTb5 protein are used to verify that increased promoter strength is reflected by increased synthesis of the corresponding protein. Once a suitable promoter is identified, it is fused to the selected CYTb5 gene and introduced into Candida for construction of a new improved production strain. It is contemplated that the coding region of the CYTb5 gene can be fused to suitable promoters or other regulatory sequences which are known to those skilled in the art.

Diacid productivity is thus improved by selective integration, amplification, and over expression of the CYTb5 gene in the C. tropicalis production host.

It should be understood that host cells into which one or more copies of the desired CYTb5 gene have been introduced can be made to include such a gene by any technique known to those skilled in the art. For example, suitable host cells include procaryotes such as Bacillus sp., Pseudomous sp., Actinomycetes sp., Eschericia sp., Mycobacterium sp., and eukaryotes such as yeast, algae, insect cells, plant cells and filamentous fungi. Suitable host cells are preferably yeast cells such as Yarrowia, Bebaromyces, Saccharomyces, Schizosaccharomyces, Pichia, Lipomyces, Rhodosporidium, Rhodotorula, Trichosporan, Cryptococcus, Endomyces, Galactomyces, Williopsis, Waltomyces, and most preferably those of the Candida genus. Preferred species of Candida are tropicalis, maltosa, apicola, paratropicalis, albicans, cloacae, guillermondii, intermedia, lipolytica, parapsilosis and zeylenoides. Particularly preferred hosts include C. tropicalis strains that have been genetically modified so that one or more of the chromosomal POX4A, POX4B and both POX5 genes have been disrupted as described e.g., in U.S. Pat. Nos. 5,254,466 and 5,620,878, each incorporated herein by reference. The POX4 and POX5 gene disruptions effectively block the β-oxidation pathway at its first reaction (which is catalyzed by acyl-CoA oxidase) in a *C. tropicalis* host strain. The POX4A and POX5 genes encode distinct subunits of long chain acyl-CoA oxidase, which are the peroxisomal polypeptides (PXPs) designated PXP-4 and PXP-5, respectively. The disruption of one or more of these genes results in a partial or complete inactivation of the β-oxidation pathway thus allowing enhanced yields of dicarboxylic acid by redirecting the substrate toward the co-oxidation pathway and also prevents reutilization of the dicarboxylic acid products through the β-oxidation pathway.

Examples of strains of *C. tropicalis* which are partially beta-oxidation blocked include, H41, H41B, H51, H45, H43, H53, H534, H534B and H435 as described in aforementioned U.S. Pat. No. 5,254,466. An example of a completely beta-oxidation blocked strain of *C. tropicalis* wherein all four POX4 and POX5 genes are disrupted by a URA3 selectable marker, is H5343 (ATCC 20962) as described in U.S. Pat. No. 5,254,466.

Vectors such as plasmids, phagemids, phages, cosmids, yeast artificial chromosomes, yeast episomal plasmids, yeast replicative plasmids, and the like can be used to transform or transfect suitable host cells. Host cells may also be transformed by introducing into a cell a linear DNA vector (s) containing the desired gene sequence, i.e., CYTb5. Such linear DNA may be advantageous when it is desirable to avoid introduction of non-native (foreign) DNA into the cell. For example, DNA consisting of CYTb5 flanked by DNA sequences which are native to the originating cell can be introduced into the host cell by electroporation, lithium acetate transformation, spheroplasting and the like. Flanking DNA sequences can include selectable markers and/or other tools for genetic engineering. Yeast cells may be transformed with any of the expression vectors described herein. The term "expression vector" is used broadly herein and is intended to encompass any medium which can be used to transform a target cell. Expression vector encompasses all the examples of vectors listed herein, including, for example, integration vectors.

In one particularly useful embodiment a vector including the CYTb5 gene may also include one or more copies of a CPR (NADPH-cytochrome P450 reductase) gene. The CPR gene from yeast strain, e.g., *C. tropicalis*, which encodes the NADPH-cytochrome P450 reductase component of the ω-hydroxylase complex has been cloned and sequenced as described, e.g., in Sanglard et al., supra. *C. tropicalis* strains which have a greater number of CPR genes than the wild type strain have shown increased productivity of dicarboxylic acids as described, e.g., in aforementioned U.S. Pat. No. 5,620,878.

Specific examples of CPR genes include the CPRA and CPRB genes of *C. tropicalis* 20336 as described, e.g., in U.S. application Ser. No. 09/302,620 and International Application No. PCT/US99/2097, each incorporated herein by reference. The complete regulatory and coding regions for the CPRA gene of *C. tropicalis* 20336 and its amino acid sequence are shown in FIGS. 2A–2B and 3A–3C, respectively. The complete regulatory and coding regions for the CPRB gene of *C. tropicalis* 20336 and its amino acid sequence are shown in FIGS. 4A–4B and 5A–5C, respectively. It should be noted that there is some evidence that, in *C. tropicalis*, codon CTG is not translated as leucine in accordance with the "universal genetic code", but as serine. See, e.g., Ueda et al., Biochemie (1994) 76, 1217–1222. However, this proposition has not been conclusively proven. Accordingly, since the CTG codon at position 1180–1182 of FIG. 4A may be translated as either a leucine or a serine, the fiftieth amino acid shown in FIG. 5A is designated "X" where "X" may be leucine or serine. Likewise, since the CTG codon at position 1153–1156 of FIG. 2A may be translated as a leucine or serine, the fiftieth amino acid shown in FIG. 3A is designated "X", where "X" may be leucine or serine. It should be kept in mind that the other DNA sequences incorporating the CTG codon which encode a protein as described herein may behave similarly even if not so designated with an "X".

An example of a *C. tropicalis* strain which contains additional copies of the CYTb5 and CPR genes of *C. tropicalis* 20336 is strain HDC11 (see Table 2, Examples 12 and 15).

The aforementioned vector including the CYTb5 gene may also include one or more copies of a CYP (cytochrome P450 monooxygenase) gene. Suitable CYP genes from yeast, e.g., the strain *C. tropicalis* 20336, include but are not limited to, CYP52A1A (FIGS. 6A–6C), CYP52A2A (FIGS. 7A–7B), CYP52A2B (FIGS. 8A–8C), CYP52A3A (FIGS. 9A–9C), CYP52A3B (FIGS. 10A–10C), CYP52D4A (FIGS. 11A–11C), CYP52A5A (FIGS. 12A–12C), CYP52A5B (FIGS. 13A–13C), CYP52A8A (FIGS. 14A–14B) and CYP52A8B (FIGS. 15A–15C), as described in U.S. application Ser. No. 09/302,620 and International Application No. PCT/US99/20797.

In another aspect of the present invention, a method for increasing the production of a CYTb5 protein in a host cell is provided. The method includes (a) transforming the host cell having a naturally occurring number of CYTb5 genes with at least one CYTb5 gene encoding a CYTb5 protein having the amino acid sequence as set forth in FIGS. 1A–1C, and (b) culturing the transformed host cell and thereby increasing expression of the CYTb5 protein compared with that of the host cell containing the naturally occurring copy number of CYTb5 genes. Suitable host cells include those as described above. Preferably, the host cell is a Candida cell, and more preferably the strain of Candida is a *C. tropicalis* strain as described above. It should be understood that a host cell having a naturally occurring number of CYTb5 genes is meant to encompass cells where that number is zero (0).

In another aspect of the invention, a method for increasing production of a dicarboxylic acid in a host cell is provided. The method comprises (a) providing the host cell having a naturally occurring number of CYTb5 genes; (b) increasing, in the host cell, the number of CYTb5 genes which encode a CYTb5 protein having an amino acid sequence as shown in FIGS. 1A–1C; and (c) culturing the host cell in media containing an organic substrate which upregulates the CYTb5 gene to effect increased production of dicarboxylic acid. Suitable host cells include those as described above.

The aforementioned host cell utilized to increase production of a dicarboxylic acid may also include an increased number of CPR or CYP genes compared with the wild type host cell. Such genes have been cloned and characterized as described in U.S. application Ser. No. 09/302,620 and International Application No. PCT/US99/20797 as described above. Culturing the host cell in media containing an organic substrate upregulates the CPR gene, which results in increased production of dicarboxylic acid.

Accordingly, the productivity (grams of dicarboxylic acid/liter/hr) of substantially pure α, ω-dicarboxylic acids is significantly increased by culturing a host cell, e.g., a *C. tropicalis* strain, which has a greater number of CPR and/or CYTb5 genes than the wild type, and in which the chromosomal POX4A, POX4B and both POX5 genes may also be disrupted.

A suitable organic substrate herein can be any organic compound that is biooxidizable to a mono- or polycarboxylic acid. Such a compound can be any saturated or unsaturated aliphatic compound or any carbocyclic or heterocyclic aromatic compound having at least one terminal methyl group, a terminal carboxyl group and/or a terminal functional group which is oxidizable to a carboxyl group by biooxidation. A terminal functional group which is a derivative of a carboxyl group may be present in the substrate molecule and may be converted to a carboxyl group by a reaction other than biooxidation. For example, if the terminal group is an ester that neither the wild-type *C. tropicalis* nor the genetic modifications described herein will allow hydrolysis of the ester functionality to a carboxyl group, then a lipase can be added during the fermentation step to liberate free fatty acids. Suitable organic substrates include, but are not limited to, saturated fatty acids, unsaturated fatty acids, alkanes, alkenes, alkynes and combinations thereof.

Alkanes are a type of saturated organic substrate which are particularly useful herein. The alkanes can be linear or cyclic, branched or straight chain, substituted or unsubstituted. Particularly preferred alkanes are those having from about 4 to about 25 carbon atoms, examples of which include, but are not limited to, butane, hexane, octane, nonane, dodecane, tridecane, tetradecane, hexadecane, octadecane and the like.

Examples of unsaturated organic substrates which can be used herein include, but are not limited to, internal olefins such as 2-pentene, 2-hexene, 3-hexene, 9-octadecene and the like; unsaturated carboxylic acids such as 2-hexenoic acid and esters thereof, oleic acid and esters thereof including triglyceryl esters having a relatively high oleic acid content, erucic acid and esters thereof including triglyceryl esters having a relatively high erucic acid content, ricinoleic acid and esters thereof including triglyceryl esters having a relatively high ricinoleic acid content, linoleic acid and esters thereof including triglyceryl esters having a relatively high linoleic acid content; unsaturated alcohols such as 3-hexen-1-ol, 9-octadecen-1-ol and the like; unsaturated aldehydes such as 3-hexen-1-al, 9-octadecen-1-al and the like. In addition to the above, an organic substrate which can be used herein include alicyclic compounds having at least one internal carbon-carbon double bond and at least one terminal methyl group, a terminal carboxyl group and/or a terminal functional group which is oxidizable to a carboxyl group by biooxidation. Examples of such compounds include, but are not limited to, 3,6-dimethyl, 1,4-cyclohexadiene, 3-methylcyclohexene, 3-methyl-1,4-cyclohexadiene and the like.

Examples of the aromatic compounds that can be used herein include but are not limited to, arenes such as o-, m-, p-xylene; o-, m-, p-methyl benzoic acid; dimethyl pyridine; sterols and the like. The organic substrate can also contain other functional groups that are biooxidizable to carboxyl groups such as an aldehyde or alcohol group. The organic substrate can also contain other functional groups that are not biooxidizable to carboxyl groups and do not interfere with the biooxidation such as halogens, ethers, and the like.

Examples of saturated fatty acids which may be applied to cells incorporating CPR, CYP and/or CYTb5 genes according to the present invention include caproic, enanthic, caprylic, pelargonic, capric, undecylic, lauric, myristic, pentadecanoic, palmitic, margaric, stearic, arachidic, behenic acids and combinations thereof. Examples of unsaturated fatty acids which may be applied to cells incorporating the present CPR and/or CYTb5 genes include palmitoleic, oleic, erucic, linoleic, linolenic acids and combinations thereof. Alkanes and fractions of alkanes may be applied which include chain links from C12 to C24 in any combination. An example of preferred fatty acid mixtures are Emersol®, Tallow and HOSFFA (high oleic sunflower oil, i.e., fatty acid mixture containing approximately 80% oleic acid commercially available as Edenor®) each commercially available from Cognis Corp., Cincinnati, Ohio. The typical fatty acid composition of Emersol® and Tallow is as follows:

| | TALLOW | EMERSOL |
|---|---|---|
| C14:0 | 3.5% | 2.4% |
| C14:1 | 1.0% | 0.7% |
| C15:0 | 0.5% | — |
| C16:0 | 25.5% | 4.6% |
| C16:1 | 4.0% | 5.7% |
| C17:0 | 2.5% | — |
| C17:1 | — | 5.7% |
| C18:0 | 19.5% | 1.0% |
| C18:1 | 41.0% | 69.9% |
| C18:2 | 2.5% | 8.8% |
| C18:3 | — | 0.3% |
| C20:0 | 0.5% | — |
| C20:1 | — | 0.9% |

The following examples are meant to illustrate but not to limit the invention. All relevant microbial strains and plasmids are described in Table 1 and Table 2, respectively.

TABLE 1

List of *Escherichia coli* and *Candida tropicalis* strains

| STRAIN | GENOTYPE | SOURCE |
|---|---|---|
| *E. Coli* | | |
| XL1Blue-MRF' | endA1, gyrA96, hsdR17, $lac^-$, recA1, relA1, supE44, thi-1, [F' $lacl^qZ$ M15, proAB, Tn10] | Stratagene, La Jolla, CA |
| BM25.8 | SupE44, thi (lac-proAB) [F' traD36, $proAB^+$, $lacI^qZ$ M15] limm434 $(kan^R)$P1 $(cam^R)$ hsdR $(r_{k12}\text{-}m_{klr})$ | Clontech, Palo Alto, CA |
| XLOLR | (mcrA)183 (mcrCB-hsdSMR-mrr)173 endA1 thi-1 recA1 gyrA96 relA1 lac [F'proAB $lacI^qZ$ M15 Tn10 $(Tet^l)$ $Su^-$(nonsuppressing $l^r$(lambda resistant) | Stratagene, La Jolla, CA |

TABLE 1-continued

| List of *Escherichia coli* and *Candida tropicalis* strains | | |
|---|---|---|
| STRAIN | GENOTYPE | SOURCE |
| *C. tropicalis* | | |
| ATCC20336 | Wild-type | American Type Culture Collection, Rockville, MD |
| ATCC750 | Wild-type | American Type Culture Collection, Rockville, MD |
| ATCC 20962 | ura3A/ura3B, pox4A::ura3A/pox4B::ura3A, pox5::ura3A/pox5::URA3A | Cognis |
| H5343 ura- | ura3A/ura3B, pox4A::ura3A/pox4B::ura3A, pox5::ura3A/pox5::URA3A, ura3- | Cognis |
| HDC11 | ura3A/ura3B, pox4A::ura3A/pox4B::ura3A, pox5::ura3A/pox5::URA3A, ura3::URA3A-CYTb5 + CPR B (CYTb5 and CPR have opposite 5' to 3' orientation with respect to each other) | Cognis Note-HDC11-1 contains less integrated copies of the CYTb5/CPR insert than does HDC11-2 |

TABLE 2

List of plasmids isolated from genomic libraries and constructed for use in gene integrations.

| Plasmid | Base vector | Insert | Insert Size | Plasmid size | Description |
|---|---|---|---|---|---|
| pURAin | pNEB193 | URA3A | 1706 bp | 4399 bp | pNEB193 with the URA3A gene inserted in the AscI-PmeI site, generating a PacI site |
| pURA REDB in | pURAin | CPRB | 3266 bp | 7665 bp | pURAin containing a PCR CPRB allele containing PacI restriction sites |
| pHKM1 | pTriplEx | Truncated CPRA gene | Approx. 3.8 kb | Approx. 7.4 kb | A truncated CPRA gene obtained by first screening library containing the 5' untranslated region and 1.2 kb open reading frame |
| pHKM4 | pTriplEx | Truncated CPRA gene | Approx. 5 kb | Approx. 8.6 kb | A truncated CPRA gene obtained by screening second library containing the 3' untranslated region end sequence |
| pHKM9 | pBC-CMV | CPRB gene | Approx. 5.3 kb | Approx. 9.8 kb | CPRB allele isolated from the third library |

EXAMPLE 1

Purification of Genomic DNA from *Candida tropicalis* ATCC 20336

A. Construction of Genomic Libraries 50 ml of YEPD broth (see Appendix) was inoculated with a single colony of *C. tropicalis* 20336 from YEPD agar plate and grown overnight at 30° C. 5 ml of the overnight culture was inoculated into 100 ml of fresh YEPD broth and incubated at 30° C. for 4 to 5 hr with shaking. Cells were harvested by centrifugation, washed twice with sterile distilled water and resuspended in 4 ml of spheroplasting buffer (1 M Sorbitol, 50 mM EDTA, 14 mM mercaptoethanol) and incubated for 30 min at 37° C. with gentle shaking. 0.5 ml of 2 mg/ml zymolyase (ICN Pharmaceuticals, Inc., Irvine, Calif.) was added and incubated at 37° C. with gentle shaking for 30 to 60 min. Spheroplast formation was monitored by SDS lysis. Spheroplasts were harvested by brief centrifugation (4,000 rpm, 3 min) and were washed once with the spheroplast buffer without mercaptoethanol. Harvested spheroplasts were then suspended in 4 ml of lysis buffer (0.2 M Tris/pH 8.0, 50 mM EDTA, 1% SDS) containing 100 mg/ml RNase (Qiagen Inc., Chatsworth, Calif.) and incubated at 37° C. for 30 to 60 min.

Proteins were denatured and extracted twice with an equal volume of chloroform/isoamyl alcohol (24:1) by gently mixing the two phases by hand inversions. The two phases were separated by centrifugation at 10,000 rpm for 10 min and the aqueous phase containing the high-molecular weight DNA was recovered. To the aqueous layer NaCl was added to a final concentration of 0.2 M and the DNA was precipitated by adding 2 vol of ethanol. Precipitated DNA was spooled with a clean glass rod and resuspended in TE buffer (10 mM Tris/pH 8.0, 1 mM EDTA) and allowed to dissolve overnight at 4° C. To the dissolved DNA, RNase free of any DNase activity (Qiagen Inc., Chatsworth, Calif.) was added to a final concentration of 50 mg/ml and incubated at 37° C. for 30 min. Then protease (Qiagen Inc., Chatsworth, Calif.)

was added to a final concentration of 100 mg/ml and incubated at 55 to 60° C. for 30 min. The solution was extracted once with an equal volume of phenol/chloroform/isoamyl alcohol (25:24:1) and once with equal volume of chloroform/isoamyl alcohol (24:1). To the aqueous phase 0.1 vol of 3 M sodium acetate and 2 volumes of ice cold ethanol (200 proof) were added and the high molecular weight DNA was spooled with a glass rod and dissolved in 1 to 2 ml of TE buffer.

B. Genomic DNA Preparation for PCR Amplification of CYTb5 and CPR Genes

Five 5 ml of YPD medium was inoculated with a single colony and grown at 30° C. overnight. The culture was centrifuged for 5 min at 1200×g. The supernatant was removed by aspiration and 0.5 ml of a sorbitol solution (0.9 M sorbitol, 0.1 M Tris-Cl pH 8.0, 0.1 M EDTA) was added to the pellet. The pellet was resuspended by vortexing and 1 ml of 2-mercaptoethanol and 50 ml of a 10 mg/ml zymolyase solution were added to the mixture. The tube was incubated at 37° C. for 1 hr on a rotary shaker (200 rpm). The tube was then centrifuged for 5 min at 1200×g and the supernatant was removed by aspiration. The protoplast pellet was resuspended in 0.5 ml 1×TE (10 mM Tris-Cl pH 8.0, 1 mM EDTA) and transferred to a 1.5 ml microcentrifuge tube. The protoplasts were lysed by the addition of 50 ml 10% SDS followed by incubation at 65° C. for 20 min. Next, 200 ml of 5M potassium acetate was added and after mixing, the tube was incubated on ice for at least 30 min. Cellular debris was removed by centrifugation at 13,000×g for 5 min. The supernatant was carefully removed and transferred to a new microfuge tube. The DNA was precipitated by the addition of 1 ml 100% (200 proof) ethanol followed by centrifugation for 5 min at 13,000×g. The DNA pellet was washed with 1 ml 70% ethanol followed by centrifugation for 5 min at 13,000×g. After partially drying the DNA under a vacuum, it was resuspended in 200 ml of 1×TE. The DNA concentration was determined by ratio of the absorbance at 260 nm/280 nm ($A_{260/280}$).

EXAMPLE 2

Construction of *Candida tropicalis* 20336 Genomic Libraries

Three genomic libraries of *C. tropicalis* were constructed, two at Clontech Laboratories, Inc., (Palo Alto, Calif.) and one at Henkel Corporation (Cincinnati, Ohio).

A. Clontech Libraries

The first Clontech library was made as follows: Genomic DNA was prepared from *C. tropicalis* 20336 as described above, partially digested with EcoRI and size fractionated by gel electrophoresis to eliminate fragments smaller than 0.6 kb. Following size fractionation, several ligations of the EcoRI genomic DNA fragments and lambda (λ) TriplEx® vector (FIG. 16) arms with EcoRI sticky ends were packaged into λ phage heads under conditions designed to obtain one million independent clones. The second genomic library was constructed as follows: Genomic DNA was digested partially with Sau3A1 and size fractionated by gel electrophoresis. The DNA fragments were blunt ended using standard protocols as described, e.g., in Sambrook et al, *Molecular Cloning: A Laboratory Manual,* 2ed. Cold Spring Harbor Press, USA (1989), incorporated herein by reference. The strategy was to fill in the Sau3A1 overhangs with Klenow polymerase (Life Technologies, Grand Island, N.Y.) followed by digestion with S1 nuclease (Life Technologies, Grand Island, N.Y.). After S1 nuclease digestion the fragments were end filled one more time with Klenow polymerase to obtain the final blunt-ended DNA fragments. EcoRI linkers were ligated to these blunt-ended DNA fragments followed by ligation into the λ TriplEx vector. The resultant library contained approximately $2\times10^6$ independent clones with an average insert size of 4.5 kb.

B. Cognis Library

Figure 17A:
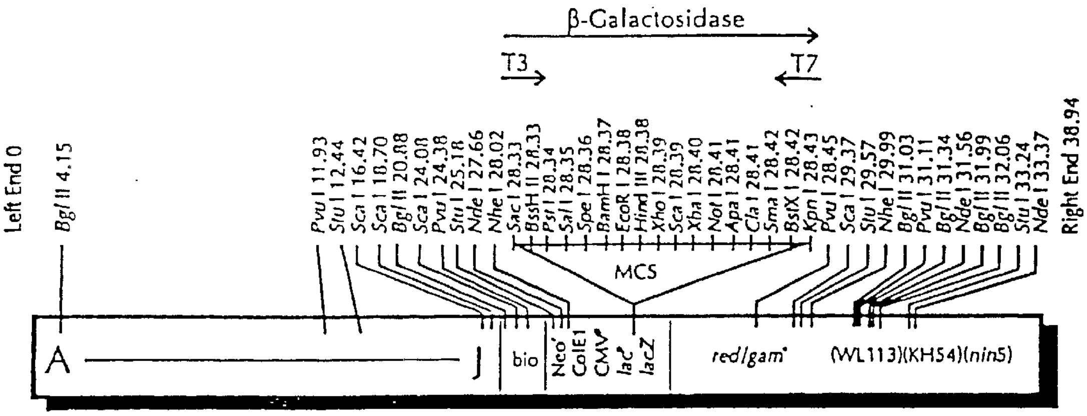
FIG. 17A is a map of the ZAP Express™ vector.

A genomic library was constructed using λ ZAP Express™ vector (Stratagene, La Jolla, Calif.) (FIG. 17A). Genomic DNA was partially digested with Sau3A1 and fragments in the range of 6 to 12 kb were purified from an agarose gel after electrophoresis of the digested DNA. These DNA fragments were then ligated to BamHI digested λ ZAP Express™ vector arms according to manufacturers protocols. Three ligations were set up to obtain approximately $9.8\times10^5$ independent clones. All three libraries were pooled and amplified according to manufacturer instructions to obtain high-titre (>$10^9$ plaque forming units/ml) stock for long-term storage. The titre of packaged phage library was ascertained after infection of *E. coli* XL1Blue-MRF' cells. *E. coli* XL1Blue-MRF' were grown overnight in either in LB medium or NZCYM (Appendix) containing 10 mM $MgSO_4$ and 0.2% maltose at 37° C. or 30° C., respectively with shaking. Cells were then centrifuged and resuspended in 0.5 to 1 volume of 10 mM $MgSO_4$. 200 ml of this *E. coli* culture was mixed with several dilutions of packaged phage library and incubated at 37° C. for 15 min. To this mixture 2.5 ml of LB top agarose or NZCYM top agarose (maintained at 60° C. ) (see Appendix) was added and plated on LB agar or NCZYM agar (see Appendix) present in 82 mm petri dishes. Phage were allowed to propagate overnight at 37° C. to obtain discrete plaques and the phage titre was determined.

EXAMPLE 3

Screening of Genomic Libraries

Figure 17B:
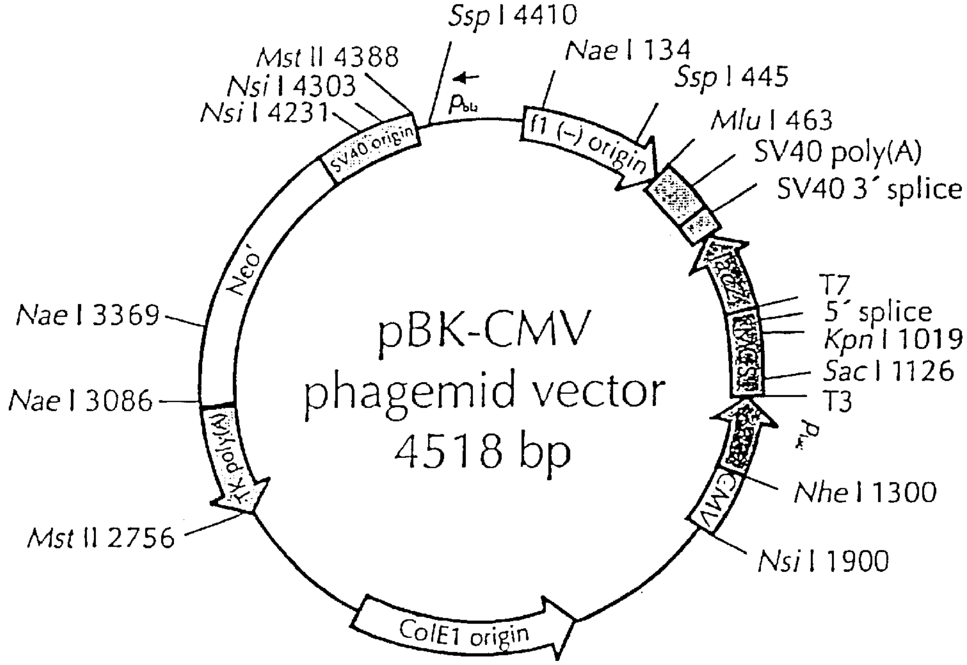
FIG. 17B is a schematic representation of cloning phagemid vector pBK-CMV.

Both λ TriplEx™ and λ ZAP Express™ vectors are phagemid vectors that can be propagated either as phage or plasmid DNA (after conversion of phage to plasmid). Therefore, the genomic libraries constructed in these vectors can be screened either by plaque hybridization (screening of lambda form of library) or by colony hybridization (screening plasmid form of library after phage to plasmid conversion). Both vectors are capable of expressing the cloned genes and the main difference is the mechanism of excision of plasmid from the phage DNA. The cloning site in λTriplEx™ is located within a plasmid which is present in the phage and is flanked by loxP site (FIG. 16). When λTriplEx™ is introduced into *E. coli* strain BM25.8 (supplied by Clontech), the Cre recombinase present in BM25.8 promotes the excision and circularization of plasmid pTriplEx from the phage λTriplEx™ at the loxP sites. The mechanism of excision of plasmid pBK-CMV (FIG. 17B) from phage λ ZAP Express™ is different. It requires the assistance of a helper phage such as ExAssist™ (Stratagene) and an *E. coli* strain such as XLOR (Stratagene). Both pTriplEx and pBK-CMV can replicate autonomously in *E. coli.*

A. Screening Genomic Libraries (Plasmid Form)

1) Colony Lifts

A single colony of *E. coli* BM25.8 was inoculated into 5 ml of LB containing 50 mg/ml kanamycin, 10 mM $MgSO_4$ and 0.1% maltose and grown overnight at 31° C., 250 rpm. To 200 ml of this overnight culture (~$4\times10^8$ cells) 1 ml of phage library ($2–5\times10^6$ plaque forming units) and 150 ml LB broth were added and incubated at 31° C. for 30 min after which 400 ml of LB broth was added and incubated at 31° C. , 225 rpm for 1 h. This bacterial culture was diluted and plated on LB agar containing 50 mg/ml ampicillin (Sigma Chemical Company, St. Louis, Mo.) and kanamycin (Sigma Chemical Company) to obtain 500 to 600 colonies/plate. The plates were incubated at 37° C. for 6 to 7 hrs until the colonies became visible. The plates were then stored at 4° C. for 1.5 hrs before placing a Colony/Plaque Screen™ Hybridization Transfer Membrane disc (DuPont NEN Research Products, Boston, Mass.) on the plate in contact with bacterial colonies. The transfer of colonies to the membrane was allowed to proceed for 3 to 5 min. The membrane was then lifted and placed on a fresh LB agar (see Appendix) plate containing 200 mg/ml of chloramphenicol with the side exposed to the bacterial colonies facing up. The plates containing the membranes were then incubated at 37° C. overnight in order to allow full development of the bacterial colonies. The LB agar plates from which colonies were initially lifted were incubated at 37° C. overnight and stored at 4° C. for future use. The following morning the membranes containing bacterial colonies were lifted and placed on two sheets of Whatman 3M (Whatman, Hillsboro, Oreg.) paper saturated with 0.5 N NaOH and left at room temperature (RT) for 3 to 6 min to lyse the cells. Additional treatment of membranes was as described in the protocol provided by NEN Research Products.

2) DNA Hybridizations

Membranes were dried overnight before hybridizing to oligonucleotide probes prepared using a non-radioactive ECL™ 3'-oligolabelling and detection system from Amersham Life Sciences (Arlington Heights, Ill.). DNA labeling, prehybridization and hybridizations were performed according to manufacturer's protocols. After hybridization, membranes were washed twice at room temperature in 5×SSC, 0.1% SDS (in a volume equivalent to 2 $ml/cm^2$ of membrane) for 5 min each followed by two washes at 50° C. in 1×SSC, 0.1% SDS (in a volume equivalent to 2 $ml/cm^2$ of membrane) for 15 min each. The hybridization signal was then generated and detected with Hyperfilm ECL™ (Amersham) according to manufacturer's protocols. Membranes were aligned to plates containing bacterial colonies from which colony lifts were performed and colonies corresponding to positive signals on X-ray were then isolated and propagated in LB broth. Plasmid DNA's were isolated from these cultures and analyzed by restriction enzyme digestions and by DNA sequencing.

B. Screening Genomic Libraries (Plaque Form)

1) λ Library Plating

*E. coli* XL1Blue-MRF' cells were grown overnight in LB medium (25 ml) containing 10 MM $MgSO_4$ and 0.2% maltose at 37° C., 250 rpm. Cells were then centrifuged (2,200×g for 10 min) and resuspended in 0.5 volumes of 10 mM $MgSO_4$. 500 ml of this *E. coli* culture was mixed with a phage suspension containing 25,000 amplified lambda phage particles and incubated at 37° C. for 15 min. To this mixture 6.5 ml of NZCYM top agarose (maintained at 60° C.) (see Appendix) was added and plated on 80–100 ml NCZYM agar (see Appendix) present in a 150 mm petridish. Phage were allowed to propagate overnight at 37° C. to obtain discrete plaques. After overnight growth plates were stored in a refrigerator for 1–2 hrs before plaque lifts were performed.

2) Plaque Lift and DNA Hybridizations

Magna Lift™ nylon membranes (Micron Separations, Inc., Westborough, Mass.) were placed on the agar surface in complete contact with 1 plaques and transfer of plaques to nylon membranes was allowed to proceed for 5 min at RT. After plaque transfer the membrane was placed on 2 sheets of Whatman 3M™ (Whatman, Hillsboro, Oreg.) filter paper saturated with a 0.5 N NaOH, 1.0 M NaCl solution and left for 10 min at RT to denature DNA. Excess denaturing solution was removed by blotting briefly on dry Whatman 3M paper. Membranes were then transferred to 2 sheets of Whatman 3M™ paper saturated with 0.5 M Tris-HCl (pH 8.0), 1.5 M NaCl and left for 5 min to neutralize. Membranes were then briefly washed in 200–500 ml of 2×SSC, dried by air and baked for 30–40 min at 80° C. The membranes were then probed with labeled DNA.

Membranes were prewashed with a 200–500 ml solution of 5×SSC, 0.5% SDS, 1 mM EDTA (pH 8.0) for 1–2 hr at 42° C. with shaking (60 rpm) to get rid of bacterial debris from the membranes. The membranes were prehybridized for 1–2 hrs at 42° C. with (in a volume equivalent to 0.125–0.25 $ml/cm^2$ of membrane) ECL Gold™ buffer (Amersham) containing 0.5 M NaCl and 5% blocking reagent. DNA fragments that were used as probes were purified from agarose gel using a QIAEX II™ gel extraction kit (Qiagen Inc., Chatsworth, Calif.) according to manufacturers protocol and labeled using an Amersham ECL™ direct nucleic acid labeling kit (Amersham). Labeled DNA (5–10 ng/ml hybridization solution) was added to the prehybridized membranes and the hybridization was allowed to proceed overnight. The following day membranes were washed with shaking (60 rpm) twice at 42° C. for 20 min each time in (in a volume equivalent to 2 $ml/cm^2$ of membrane) a buffer containing either 0.1 (high stringency) or 0.5 (low stringency)×SSC, 0.4% SDS and 360 g/l urea. This was followed by two 5 min washes at room temperature in (in a volume equivalent to 2 $ml/cm^2$ of membrane) 2×SSC. Hybridization signals were generated using the ECL™ nucleic acid detection reagent and detected using Hyperfilm ECL™ (Amersham).

Agar plugs which contained plaques corresponding to positive signals on the X-ray film were taken from the master plates using the broad-end of Pasteur pipet. Plaques were selected by aligning the plates with the x-ray film. At this stage, multiple plaques were generally taken. Phage particles were eluted from the agar plugs by soaking in 1 ml SM buffer (Sambrook et al., supra) overnight. The phage eluate was then diluted and plated with freshly grown *E. coli* XL1Blue-MRF' cells to obtain 100–500 plaques per 85 mm NCZYM agar plate. Plaques were transferred to Magna Lift nylon membranes as before and probed again using the same probe. Single well-isolated plaques corresponding to signals on X-ray film were picked by removing agar plugs and eluting the phage by soaking overnight in 0.5 ml SM buffer.

C. Conversion of λ Clones to Plasmid Form

The lambda clones isolated were converted to plasmid form for further analysis. Conversion from the plaque to the plasmid form was accomplished by infecting the plaques into *E. coli* strain BM25.8. The *E. coli* strain was grown overnight at 31° C., 250 rpm in LB broth containing 10 mM $MgSO_4$ and 0.2% maltose until the $OD_{600}$ reached 1.1–1.4. Ten milliliters of the overnight culture was removed and mixed with 100 ml of 1 M $MgCl_2$. A 200 ml volume of cells was removed, mixed with 150 ml of eluted phage suspension and incubated at 31° C. for 30 min. LB broth (400 ml) was added to the tube and incubation was continued at 31° C. for 1 hr with shaking, 250 rpm. 1–10 ml of the infected cell suspension was plated on LB agar containing 100 mg/ml ampicillin (Sigma Chemical Company, St. Louis, Mo.). Well-isolated colonies were picked and grown overnight in 5 ml LB broth containing 100 mg/ml ampicillin at 37° C., 250 rpm. Plasmid DNA was isolated from these cultures and analyzed. To convert the λ ZAP Express™ vector to plasmid form *E. coli* strains XL1Blue-MRF' and XLOR were used. The conversion was performed according to the manufacturer's (Stratagene) protocols for single-plaque excision.

EXAMPLE 4

Transformation of *C. tropicalis* Using Lithium Acetate

The following protocol was used to transform *C. tropicalis* in accordance with the procedures described in *Current Protocols in Molecular Biology,* Supplement 5, 13.7.1 (1989), incorporated herein by reference.

5 ml of YEPD was inoculated with *C. tropicalis* H5343 ura- from a frozen stock and incubated overnight on a New Brunswick shaker at 30° C. and 170 rpm. The next day, 10 μl of the overnight culture was inoculated into 50 ml YEPD and growth was continued at 30° C., 170 rpm. The following day the cells were harvested at an $OD_{600}$ of 1.0. The culture was transferred to a 50 ml polypropylene tube and centrifuged at 1000×g for 10 min. The cell pellet was resuspended in 10 ml sterile TE (10 mM Tris-Cl and 1 mM EDTA, pH 8.0). The cells were again centrifuged at 1000×g for 10 min and the cell pellet was resuspended in 10 ml of a sterile lithium acetate solution [LiAc (0.1 M lithium acetate, 10 mM Tris-Cl, pH 8.0, 1 mM EDTA)]. Following centrifugation at 1000×g for 10 min., the pellet was resuspended in 0.5 ml LiAc. This solution was incubated for 1 hr at 3° C. while shaking gently at 50 rpm. A 0.1 ml aliquot of this suspension was incubated with 5 μg of transforming DNA at 30° C. with no shaking for 30 min. A 0.7 ml PEG solution (40% wt/vol polyethylene glycol 3340, 0.1 M lithium acetate, 10 mM Tris-Cl, pH 8.0, 1 mM EDTA) was added and incubated at 30° C. for 45 min. The tubes were then placed at 42° C. for 5 min. A 0.2 ml aliquot was plated on synthetic complete media minus uracil (SC-uracil) (Kaiser et al. *Methods in Yeast Genetics,* Cold Spring Harbor Laboratory Press, USA, 1994, incorporated herein by reference). Growth of transformants was monitored for 5 days. After three days, several transformants were picked and transferred to SC-uracil plates for genomic DNA preparation and screening.

EXAMPLE 5

Plasmid DNA Isolation

Plasmid DNA were isolated from *E. coli* cultures using Qiagen plasmid isolation kit (Qiagen Inc., Chatsworth, Calif.) according to manufacturer's instructions.

EXAMPLE 6

DNA Sequencing and Analysis

DNA sequencing was performed at Sequetech Corporation (Mountain View, Calif.) using Applied Biosystems automated sequencer (Perkin Elmer, Foster City, Calif.). DNA sequences were analyzed with MacVector and GeneWorks software packages (Oxford Molecular Group, Campbell, Calif.).

EXAMPLE 7

PCR Protocols

PCR amplification was carried out in a Perkin Elmer Thermocycler using the AmpliTaqGold enzyme (Perkin Elmer Cetus, Foster City, Calif.) kit according to manufacturer's specifications. Following successful amplification, in some cases, the products were digested with the appropriate enzymes and gel purified using QiaexII (Qiagen, Chatsworth, Calif.) as per manufacturer instructions. In specific cases the Ultma Taq polymerase (Perkin Elmer Cetus, Foster City, Calif.) or the Expand Hi-Fi Taq polymerase (Boehringer Mannheim, Indianapolis, Ind.) were used per manufacturer's recommendations or as defined in Table 3.

TABLE 3

PCR amplification conditions used with different primer combinations.

| PRIMER COMBINATION | Taq | TEMPLATE DENATURING CONDITION | ANNEALING TEMP/TIME | EXTENSION TEMP/TIME | CYCLE Number |
|---|---|---|---|---|---|
| 3674-41-1/41-2/41-4 + 3674-41-4 | Ampli-Taq Gold | 94 C/30 sec | 55 C/30 sec | 72 C/1 min | 30 |
| URA Primer 1a<br>URA Primer 1b | Ampli-Taq Gold | 95 C/1 min | 70 C/1 min | 72 C/2 min | 35 |
| URA Primer 2a<br>URA Primer 2b | Ampli-Taq Gold | 95 C/1 min | 70 C/1 min | 72 C/2 min | 35 |
| CPR B#1 | Expand | 94 C/15 sec | 50 C/30 sec | 68 C/3 min | 10 |
| CPR B#2 | Hi-Fi Taq | 94 C/15 sec | 50 C/30 sec | 68 C/3 min + 20 sec/cycle | 15 |
| CYTb5 #1<br>CYTb5 #2 | Ultma Taq | 95° C./15 sec | 45° C./30 sec | 72° C./2 min | 25 |

Table 4 below contains a list of primers used for PCR amplification to construct gene integration vectors or to generate probes for gene detection and isolation.

TABLE 4

Primer table for PCR amplification to construct gene integration vectors, to generate probes for gene isolation and detection and to obtain DNA sequence of constructs. (A-deoxyadenosine triphosphate [dATP], G-deoxyguanosine triphosphate [dGTP], C-deoxycytosine triphosphate [dCTP], T-deoxythymidine triphosphate [dTTP], Y-dCTP or dTTP, R-dATP or dGTP, W-dATP or dTTP, M-dATP or dCTP).

| Target gene(s) | Patent Primer Name | Lab Primer Name | Sequence (5' to 3') | PCR Product Size |
|---|---|---|---|---|
| CPRB | CPRB#1 | 3698-20A | CCTTAATTAAGAGGTCGTTGGTTGAGTTTTC (SEQ. ID NO. 17) | 3266 bp |
| | CPRB#2 | 3698-20B | CCTTAATTAATTGATAATGACGTTGCGGG (SEQ. ID NO. 18) | |
| URA3A | URA Primer 1a | 3698-7C | AGGCGCGCCGGAGTCCAAAAAGACCAACCTCTG (SEQ. ID NO. 19) | 956 bp |
| | URA Primer 1b | 3698-7D | CCTTAATTAATACGTGGATACCTTCAAGCAAGTG (SEQ. ID NO. 20) | |
| URA3A | URA Primer 2a | 3698-7A | CCTTAATTAAGCTCACGAGTTTTGGGATTTTCGAG (SEQ. ID NO. 21) | 750 bp |
| | URA Primer 2b | 3698-7B | GGGTTTAAACCGCAGAGGTTGGTCTTTTTGGACTC (SEQ. ID NO. 22) | |
| | | | GGGTTTAAAC - Pme I restriction site (SEQ. ID NO. 23) | |
| | | | AGGCGCGCC - AscI restriction site (SEQ. ID NO. 24) | |
| | | | CCTTAATTAA - PacI restriction site (SEQ. ID NO. 25) | |
| CPR | FMN1 | 3674-41-1 | TCYCAAACWGGTACWGCWGAA (SEQ. ID NO. 26) | |
| CPR | FMN2 | 3674-41-2 | GGTTTGGGTAAYTCWACTTAT (SEQ. ID NO. 27) | |
| CPR | FAD | 3674-41-3 | CGTTATTAYTCYATTTCTTC (SEQ. ID NO. 28) | |
| CPR | NADPH | 3674-41-4 | GCMACACCRGTACCTGGACC (SEQ. ID NO. 29) | |
| CPR | PRK1.F3 | PRK1.F3 | ATCCCAATCGTAATCAGC (SEQ. ID NO. 30) | |
| CPR | PRK1.F5 | PRK1.F5 | ACTTGTCTTCGTTTAGCA (SEQ. ID NO. 31) | |
| CPR | PRK4.R20 | PRK4.R20 | CTACGTCTGTGGTGATGC (SEQ. ID NO. 32) | |
| pTriplEx vector | Triplex5' | Triplex5' | CTCGGGAAGCGCGCCATTGTGTTGG (SEQ. ID. NO. 33) | |
| pTriplEx vector | Triplex3' | Triplex3' | TAATACGACTCACTATAGGGCGAATTGGC (SEQ. ID NO. 34) | |
| CYTb5 | CYTb5 #1 | | GGGTTAATTAACATACTTCAAGCAGTTTGG (SEQ. ID NO. 35) | |
| | CYTb5 #2 | | CCCTTAATTAAGGGGGGATGGAAGTGGCCG (SEQ. ID NO. 36) | |
| | 3698-66A | | ATAAGAATGCGGCCGCTGAACGAGAACCACATCC AGGAG (SEQ. ID NO. 37) | |
| | 3698-66B | | CCTTAATTAAGGATAACCACATCCATACGTCGC (SEQ. ID NO. 38) | |

EXAMPLE 8

Yeast Colony PCR Procedure for Confirmation of Gene Integration into the Genome of *C. tropicalis*

Single yeast colonies were removed from the surface of transformation plates, suspended in 50 $\mu$l of spheroplasting buffer (50 mM KCl, 10 mM Tris-HCl, pH 8.3, 1.0 mg/ml Zymolyase, 5% glycerol) and incubated at 37° C. for 30 min. Following incubation, the solution was heated for 10 min at 95° C. to lyse the cells. Five $\mu$l of this solution was used as a template in PCR. Expand Hi-Fi Taq polymerase (Boehringer Mannheim, Indianapolis, Ind.) was used in PCR coupled with a gene-specific primer (gene to be integrated) and a URA3 primer. If integration did occur, amplification would yield a PCR product of predicted size confirming the presence of an integrated gene.

EXAMPLE 9

Fermentation Method for Gene Induction Studies

A fermentor was charged with a semi-synthetic growth medium having the composition 75 g/l glucose (anhydrous), 6.7 g/l Yeast Nitrogen Base (Difco Laboratories), 3 g/l yeast extract, 3 g/l ammonium sulfate, 2 g/l monopotassium phosphate, 0.5 g/l sodium chloride. Components were made as concentrated solutions for autoclaving then added to the fermentor upon cooling: final pH approximately 5.2. This charge was inoculated with 5–10% of an overnight culture of *C. tropicalis* ATCC 20962 prepared in YM medium (Difco Laboratories) as described in the methods of Examples 17 and 20 of U.S. Pat. No. 5,254,466, which is incorporated herein by reference. *C. tropicalis* ATCC 20962 is a POX 4 and POX 5 disrupted *C. tropicalis* ATCC 20336. Air and agitation were supplied to maintain the dissolved oxygen at greater than about 40% of saturation versus air. The pH was maintained at about 5.0 to 8.5 by the addition of 5N caustic soda on pH control. Both a fatty acid feedstream (commercial oleic acid in this example) having a typical composition: 2.4% $C_{14}$; 0.7% $C_{14:1}$; 4.6% $C_{16}$; 5.7% $C_{16:1}$; 5.7% $C_{17:1}$; 1.0% $C_{18}$; 69.9% $C_{18:1}$; 8.8% $C_{18:2}$; 0.30% $C_{18:3}$; 0.90% $C_{20:1}$ and a glucose co-substrate feed were added in a feedbatch mode beginning near the end of exponential growth. Caustic was added on pH control during the bioconversion of fatty acids to diacids to maintain the pH in the desired range. Typically, samples for gene induction studies were collected just prior to starting the fatty acid feed and over the first 10 hours of bioconversion. Determination of fatty acid and diacid content was determined by a standard methyl ester protocol using gas liquid chromatography (GLC) (see Example 12). Gene induction was measured using the QC-RT-PCR protocol described in this application.

EXAMPLE 10

RNA Preparation

The first step of this protocol involves the isolation of total cellular RNA from cultures of *C. tropicalis*. The cellular RNA was isolated using the Qiagen RNeasy Mini Kit (Qiagen Inc., Chatsworth, Calif.) as follows: 2 ml samples of C tropicalis cultures were collected from the fermentor in a standard 2 ml screw capped Eppendorf style tubes at various times before and after the addition of the fatty acid or alkane substrate. Cell samples were immediately frozen in liquid nitrogen or a dry-ice/alcohol bath after their harvesting from the fermentor. To isolate total RNA from the samples, the tubes were allowed to thaw on ice and the cells pelleted by centrifugation in a microfuge for 5 min at 4° C. and the supernatant was discarded while keeping the pellet ice-cold. The microfuge tubes were filled ⅔ full with ice-cold Zirconia/Silica beads (0.5 mm diameter, Biospec Products, Bartlesville, Okla.) and the tube filled to the top with ice-cold RLT* lysis buffer (* buffer included with the Qiagen RNeasy Mini Kit). Cell rupture was achieved by placing the samples in a mini bead beater (Biospec Products, Bartlesville, Okla.) and immediately homogenized at full speed for 2.5 min. The samples were allowed to cool in an ice water bath for 1 min and the homogenization/cool process repeated two more times for a total of 7.5 min homogenization time in the beadbeater. The homogenized cells samples were microfuged at full speed for 10 min and 700 ml of the RNA containing supernatant removed and transferred to a new eppendorf tube. 700 ml of 70% ethanol was added to each sample followed by mixing by inversion. This and all subsequent steps were performed at room temperature. Seven hundred microliters of each ethanol treated sample were transferred to a Qiagen RNeasy spin column, followed by centrifugation at 8,000×g for 15 sec. The flow through was discarded and the column reloaded with the remaining sample (700 ml) and re-centrifuged at 8,000×g for 15 sec. The column was washed once with 700 ml of buffer RW1*, and centrifuged at 8,000×g for 15 sec and the flow through discarded. The column was placed in a new 2 ml collection tube and washed with 500 ml of RPE* buffer and the flow through discarded. The RPE* wash was repeated with centrifugation at 8,000×g for 2 min and the flow through discarded. The spin column was transferred to a new 1.5 ml collection tube and 100 ml of RNase free water added to the column followed by centrifugation at 8,000×g for 15 seconds. An additional 75 ml of RNase free water was added to the column followed by centrifugation at 8,000×g for 2 min. RNA eluted in the water flow through was collected for further purification.

The RNA eluate was then treated to remove contaminating DNA. Twenty microliters of 10×DNase I buffer (0.5 M tris (pH 7.5), 50 mM $CaCl_2$, 100 mM $MgCl_2$), 10 ml of RNase-free DNase I (2 Units/ml, Ambion Inc., Austin, Tex.) and 40 units Rnasin (Promega Corporation, Madison, Wis.) were added to the RNA sample. The mixture was then incubated at 37° C. for 15 to 30 min. Samples were placed on ice and 250 ml Lysis buffer RLT* and 250 ml ethanol (200 proof) added. The samples were then mixed by inversion. The samples were transferred to Qiagen RNeasy spin columns and centrifuged at 8,000×g for 15 sec and the flow through discarded. Columns were placed in new 2 ml collection tubes and washed twice with 500 ml of RPE* wash buffer and the flow through discarded. Columns were transferred to new 1.5 ml eppendorf tubes and RNA was eluated by the addition of 100 ml of DEPC treated water followed by centrifugation at 8,000×g for 15 sec. Residual RNA was collected by adding an additional 50 ml of RNase free water to the spin column followed by centrifugation at full speed for 2 min. 10 ml of the RNA preparation was removed and quantified by the ($A_{260/280}$) method. RNA was stored at −70° C. Yields were found to be 30–100 mg total RNA per 2.0 ml of fermentation broth.

EXAMPLE 11

Quantitative Competitive Reverse Transcription Polymerase Chain Reaction (QC-RT-PCR) Protocol QC-RT-PCR is a technique used to quantitate the amount of a specific RNA in a RNA sample. This technique employs the synthesis of a specific DNA molecule that is complementary to an RNA molecule in the original sample by reverse transcription and its subsequent amplification by polymerase chain reaction. By the addition of various amounts of a competitor RNA molecule to the sample one can determine the concentration of the RNA molecule of interest (e.g., the mRNA transcripts of the CYTb5 gene). The levels of specific mRNA transcripts were assayed over time in response to the addition of fatty acid or alkane substrates to the growth medium of fermentation grown *C. tropicalis* cultures for the identification and characterization of the genes involved in the oxidation of these substrates. This approach is used to identify the CYTb5 gene involved in the oxidation of any given substrate based upon its transcriptional regulation.

A. Primer Design

The first requirement for QC-RT-PCR is the design of the primer pairs to be used in the reverse transcription and subsequent PCR reactions. These primers need to be unique and specific to the gene of interest. Primers used to measure the expression of the CYTb5 gene of *C. tropicalis* 20336 using the QC-RT-PCR protocol are listed in Table 5.

TABLE 5

Primers used to measure *C. tropicalis* GYTB5 gene expression in the QC-RT-PCR reactions.

| Primer Name | Direction | Target | Sequence |
|---|---|---|---|
| 3740-179A | F | CYTb5 | CACACCACCCACGACGACTTGTG (SEQ. ID NO. 39) |
| 3740-179C | B | CYTb5 | CTTCCGTGCTGAACGACTGCG (SEQ. ID NO. 40) |

F = Forward
B = Backward

B. Design and Synthesis of the Competitor DNA Template

The competitor RNA is synthesized in vitro from a competitor DNA template that has the T7 polymerase promoter and preferably carries a small deletion of e.g., about 10 to 25 nucleotides relative to the native target RNA sequence. The DNA template for the in-vitro synthesis of the competitor RNA is synthesized using PCR primers that are between 42 and 46 nucleotides in length. In this example, the primer pairs for the synthesis of the CYTb5 competitor DNA are shown in Table 6.

TABLE 6

Forward and Reverse primers used to synthesize the competitor RNA template for the QC-RT-PCR measurement of CYTb5 gene expression.

| | | |
|---|---|---|
| Forward Primer | Forward Competitor primer - 3740-179B | TAATACGACTCACTATAGGGAGGCACACCA CCCACGACGACTTGTG (SEQ. ID NO. 41) |
| Reverse Primer | Reverse Competitor primer - 3740-179D | CTTCCGTGCTGAACGACTGCGAATCTTAGC GCCCTTCAAGTT (SEQ. ID NO. 42) |

The forward primer was used with the corresponding reverse primer to synthesize the competitor DNA template. The primer pairs were combined in a standard Taq Gold polymerase PCR reaction according to the manufacturer's recommended conditions (Perkin-Elmer/Applied Biosystems, Foster City, Calif.). The PCR reaction mix contained a final concentration of 250 nM each primer and 10 ng *C. tropicalis* chromosomal DNA for template. The reaction mixture was placed in a thermocycler for 25 to 35 cycles using the highest annealing temperature possible during the PCR reactions to assure a homogeneous PCR product (in this case 62° C.). The PCR products were either gel purified or filtered purified to remove un-incorporated nucleotides and primers. The competitor template DNA was then quantified using the ($A_{260/280}$) method.

C. Synthesis of the Competitor RNA

Competitor template DNA was transcribed In-Vitro to make the competitor RNA using the Megascript T7 kit from Ambion Biosciences (Ambion Inc., Austin, Tex.). 250 nanograms (ng) of competitor DNA template and the in-vitro transcription reagents are mixed according to the directions provided by the manufacturer. The reaction mixture was incubated for 4 hrs at 37° C. The resulting RNA preparations were then checked by gel electrophoresis for the conditions giving the highest yields and quality of competitor RNA. This often required optimization according to the manufacturer's specifications. The DNA template was then removed using DNase I as described in the Ambion kit. The RNA competitor was then quantified by the ($A_{260/280}$) method. Serial dilution's of the RNA (1 ng/ml to 1 femtogram (fg)/ml) were made for use in the QC-RT-PCR reactions and the original stocks stored at −70° C.

D. QC-RT-PCR Reactions

QC-RT-PCR reactions were performed using rTth polymerase from Perkin-Elmer(Perkin-Elmer/Applied Biosystems, Foster City, Calif.) according to the manufacturer's recommended conditions. The reverse transcription reaction was performed in a 10 ml volume with a final concentrations of 200 mM for each dNTP, 1.25 units rTth polymerase, 1.0 mM MnCl2, 1× of the 10×buffer supplied with the Enzyme from the manufacturer, 100 ng of total RNA isolated from a fermentor grown culture of *C. tropicalis* and 1.25 mM of the appropriate reverse primer. To quantitate CYTb5 expression in *C. tropicalis* an appropriate reverse primer was 5' CTTCCGTGCTGAACGACTGCG 3' (3740–179C). Several reaction mixes were prepared for each RNA sample characterized. To quantitate CYTb5 expression a series of 8 to 12 of the previously described QC-RT-PCR reaction mixes were aliquoted to different reaction tubes. To each tube 1 ml of a serial dilution containing from 100 pg to 100 fg CYTb5 competitor RNA per ml was added bringing the final reaction mixtures up to the final volume of 10 µl. The QC-RT-PCR reaction mixtures were mixed and incubated at 70° C. for 15 min according to the manufacturer's recommended times for reverse transcription to occur. At the completion of the 15 minute incubation, the sample temperature was reduced to 4° C. to stop the reaction and 40 µl of the PCR reaction mix added to the reaction to bring the total volume up to 50 µl. The PCR reaction mix consists of an aqueous solution containing 0.3125 mM of the forward primer 5' CACACCACCCAC-GACGACTTGTG 3' (3740–179A), 3.125 mM $MgCl_2$ and 1×chelating buffer supplied with the enzyme from Perkin-Elmer. The reaction mixtures were placed in a thermocycler (Perkin-Elmer GeneAmp PCR System 2400, Perkin-Elmer/Applied Biosystems, Foster City, Calif.) and the following PCR cycle performed: 94° C. for 1 min. followed by 94° C. for 10 seconds followed by 58° C. for 40 seconds for 17 to 22 cycles. The PCR reaction was completed with a final incubation at 58° C. for 2 min followed by 4° C. In some reactions where no detectable PCR products were produced the samples were returned the thermocycler for additional cycles, this process was repeated until enough PCR products were produced to quantify using HPLC. The number of cycles necessary to produce enough PCR product is a function of the amount of the target mRNA in the 100 ng of total cellular RNA. In cultures where the CYTb5 gene is highly expressed there is sufficient CYTb5 mRNA message present and less PCR cycles ($\leq 17$) are required to produce quantifiable amount of PCR product. The lower the concentrations of the target mRNA present the more PCR cycles are required to produce a detectable amount of product.

E. HPLC Quantification

Upon completion of the QC-RT-PCR reactions the samples were analyzed and quantitated by HPLC. Five to fifteen microliters of the QC-RT-PCR reaction mix was injected into a Waters Bio-Compatible 625 HPLC with an attached Waters 484 tunable detector. The detector was set to measure a wave length of 254 nm. The HPLC contained a Sarasep brand DNASep™ column (Sarasep, Inc., San Jose, Calif.) which was placed within the oven and the temperature set for 52° C. The column was installed according to the manufacturer's recommendation of having 30 cm. of heated PEEK tubing installed between the injector and the column. The system was configured with a Sarasep brand Guard column positioned before the injector. In addition, there was a 0.22 mm filter disk just before the column, within the oven. Two buffers were used to create an elution gradient to resolve and quantitate the PCR products from the QC-RT-PCR reactions. Buffer-A consists of 0.1 M tri-ethyl ammonium acetate (TEAA) and 5% acetonitrile (volume to volume). Buffer-B consists of 0.1 M TEAA and 25% acetonitrile (volume to volume). The QC-RT-PCR samples were injected into the HPLC and the linear gradient of 75% buffer-A/25% buffer-B to 45% buffer-A/ 55% B was run over 6 min at a flow rate of 0.85 ml per minute. The QC-RT-PCR product of the competitor RNA being smaller is eluted from the HPLC column before the QC-RT-PCR product from the CYTb5 mRNA(U). The amount of the QC-RT-PCR products are plotted and quantitated with an attached Waters Corporation 745 data module. The log ratios of the amount of CYTb5 mRNA QC-RT-PCR product (U) to competitor QC-RT-PCR product (C), as measured by peak areas, was plotted and the amount of competitor RNA required to equal the amount of CYTb5 mRNA product determined.

EXAMPLE 12

Evaluation of New Strains in Shake Flasks

The CYTb5 and CPR amplified strains such as strains HDC11-1 and HDC11-2 and H5343 were evaluated for diacid production in shake flasks. The diacid production of the CYTb5 and CPR amplified strains was also compared with the diacid production of various genetically modified strains of *C. tropicalis* 20336 [(HDC1-contains additional copies of CYP52A2A gene (FIGS. 7A–7B); HDC 10-2-contains additional copies of the CPRB gene (FIGS. 4A–4B); HDC-15-contains additional copies of the CYP52A5A gene (FIGS. 12A–12C); HDC16-2-contains additional copies of the CPRB gene and the CYP52A5A gene (FIGS. 4A–4B and 12A–12C, respectively); and HDC23-3-contains additional copies of the CPRB and CYP52A2A gene (FIGS. 4A–4B and 7A–7B, respectively) which were constructed according to the procedures described in U.S. application Ser. No. 09/302,620 and International Application No. PCT/US99/20797.

A. Standard Protocol for Shake Flask 100 ml of YEPD (Appendix) was inoculated with 1 ml of a pre-prepared glycerol stock of *C. tropicalis* followed by the addition of 1 drop of SAG471 antifoam (dimethylpolysiloxane, commercially available from Osi Specialties, Sistersville, W. Va.). The culture was allowed to grow for 20 hrs in a 30° C. shaker at 300 rpm. The 100 ml culture was then transferred to the DCA2 medium (Appendix) by combining:

| | |
|---|---|
| 100 ml | YEPD-culture |
| 100 ml | Glycerol [500 g/L] |

-continued

| | |
|---|---|
| 20 ml | YNB (Appendix) [334 g/L] |
| 780 ml | DCA2 |

The cell suspension was divided into five 2000 ml baffled shake flasks followed by the addition of one drop of SAG471 antifoam. The culture was allowed to grow for 30 hrs in a 30° C. shaker at 300 rpm. The media was transferred to autoclaved plastic bottles and the cells were centrifuged at 4068 g for 5 min. The supernatant was discarded and the cells were resuspended in DCA3 (Appendix):

| | | |
|---|---|---|
| 100 ml | Glycerol | [500 g/L] |
| 20 ml | YNB | [334 g/L] |
| 880 ml | 0.3M | potassium-phosphate buffer pH = 7.5 |

The cell suspension was assigned to 500 ml baffled shake flasks in 50 ml quantities and 10% w/v octadecane (Sigma Chemical Company, St. Louis, Mo.) or 3% w/v oleic acid (Fisher Scientific Co.) was added. The bioconversion was allowed to take place in a shaking incubator at 30° C. and 300 rpm for 48 hrs. Subsequently, the cultures were stored frozen at −20° C. in the shake flask. Before the analysis the cultures were thawed and heated to 70° C., mixed and transferred to 50 ml Falcon tubes. Samples were harvested and the diacid concentrations were analyzed by the procedure described below. FIG. 18 depicts the scheme used for the extraction and analysis of diacids and monoacids from fermentations broths.

B. Biomass Determination Protocol

1. Oleic Acid Samples

The samples were heated to 70° C. and vortexed to mix. An aliquot from each sample (10 ml) was then transferred to a 50 ml Falcon tube, followed by the addition of 2.5 ml KOH (7%). Each Falcon tube was centrifuged for 10 min at 3000 rpm and the supernatant was discarded. Water (15 ml) was then added to each Falcon tube containing centrifuged cells. If the supernatant was clear following addition of the water to the centrifuged cells, the cells were then dried in an 80° C. oven until two dry weights taken hours apart remained the same. If the supernatant was turbid following addition of water to the centrifuged cells, 2.5 ml KOH (7%) was added. Following addition of KOH, the centrifuged cells from each tube were resuspended by vortexing, and recentrifuged for 10 min at 3000 rpm followed by removal of the supernatent. The cells were then washed with 15 ml water and then resuspended by vortexing. The cells were resuspended in water, recentrifuged for 10 min at 3000 rpm and the supernatant was discarded. The cells were resuspended in a small volume of water, vortexed and poured into dry, pre-weighed aluminum boats. Each Falcon tube was then rinsed 1–2 times with water into the drying-boats. The drying-boats were dried in an 80° C. oven until two dry weights taken hours apart remained the same.

2. Octadecane Samples

The samples were heated to 70° C. and vortexed to mix. A 10 ml aliquot of each sample was then transferred to a 50 ml Falcon tube, followed by the addition of 2.5 ml KOH (7%). Hexane (5 ml) was then added to each Falcon tube and mixed by vortexing. Each Falcon tube containing sample was then centrifuged for 10 min at 3000 rpm and the supernatant was discarded. Water (15 ml) was then added to the centrifuged cells which were resuspended by vortexing. The resuspended cells in each tube were then centrifuged for 10 min at 3000 rpm and the supernatant was discarded. The centrifuged cells were then washed with 15 ml water, resuspended in the water by vortexing and centrifuged for 10 min at 3000 rpm. The supernatant was discarded and the cells were resuspended in a small volume of water, vortexed and poured into dry, pre-weighed aluminum boats. Each falcon tube was rinsed 1–2 times with water into drying-boats, and then dried in a 80° C. oven.

C. Extraction Protocol—Extraction of Broth Using Methyl-t-butylether

The samples were heated to 70° C. An EPA vial with the cap off was tared on a two-place balance. One gram of sample broth was then weighed into each vial and the weight was recorded. The balance was tared and one gram of internal standard (C15 Monoacid in KOH [10g/kg]) was then weighed. The vial was capped and swirled to mix. The aforementioned steps were repeated for all samples, usually run in groups of 6 at a time. Subsequently the vials were removed to the hood. HCl (6N, 6.8 ml) was pipetted into each vial which was capped and swirled to mix. Methyl-t-butylether (20 ml) was then added to each vial, which was capped and vortexed for 1 min. Anhydrous magnesium sulfate ($MgSO_4$, 5 g) was weighed into a weighing dish. Each vial was shaken and $MgSO_4$ was immediately added to each shaken vial. Each vial was capped tightly and given a quick shake. Subsequently, the cap on each vial was carefully loosened to relieve pressure. The cap on each vial was then tightened and the vial was vortexed for 1 min. The steps from the addition of $MgSO_4$ to each vial to vortexing the capped vial were repeated for each vial. The vials were then cooled for about 5 min and vortexed for 1 min. The contents of the vials were then allowed to settle. A 4 ml vial was labeled for each sample and 1 ml of solution from each EPA vial was pipetted into each labeled 4 ml vial.

D. Methylation of Extracted Material

Boron trifluoride (1 ml) in methanol reagent ($BF_3$-MeOH) was added to each 4 ml vial. The vials were then capped and swirled to mix. Subsequently, the vials were placed in a 50° C. dry block and left in the dry block for a total of 20 min. The vials were then removed from the block and cooled for 5 min, followed by the addition of 0.5 ml hexane to each vial. Following addition of a saturated NaCl solution (1.5 ml) to each vial (71.5 g NaCl in 200 ml distilled water), the vials were then capped and shaken for 1 min. Each vial was allowed to set until layers separated. Subsequently, a gas chromatography (GC) vial was labeled for each sample. Most of the top layer from the 4 ml vial was then transferred into the GC vial. The bottom layer in the 4 ml vial was not transferred into the GC vial. Each GC vial was then capped carefully and placed into the GC autosampler tray. Once all of the day's samples were loaded, GC was initiated. During run one, usually two methanol blanks were employed using the method stored as TEMP.MET on the integrator at the start of day to prepare GC. One methanol blank was run after each 10 samples and as the last sample to keep the GC column clean. The GC conditions were as follows:

HP-Innowax 30 m by 0.32 mm ID column with 0.5 m film thickness

Split ratio 1:100

Column head pressure 13.5 psig

Injector temperature 240° C.

FID Detector temperature 250° C.

Oven temperature program:

90° C. ramp to 190° C. at 7° C./min then ramp to 250° C. at 12° C./min and hold for 30 min.

This is saved in integrators as DCAME2.MET

The Flask results are shown below in Tables 7–10.

TABLE 7

Bioconversion of 3% w/v oleic acid by different recombinant strains of *Candida tropicalis*
Experiment 1

| | Genes Amplified | Average C18:1 Diacid (g/kg) | No. of Expts. | Standard Deviation (%) | % Improvement |
|---|---|---|---|---|---|
| H5343 | — | 17.5 | 3 | 7.4 | 0.0 |
| HDC1 | CYP52A2A | 16.5 | 3 | 17.5 | −5.4 |
| HDC10-2 | CPR B | 17.5 | 3 | 17.2 | 0.3 |
| HDC15 | CYP52A5A | 21.5 | 3 | 16 | 23.3 |
| HDC23-3 | CPR B + CYP52A2A | 23.3 | 3 | 8.7 | 33.5 |

TABLE 8

Bioconversion of 3% w/v oleic acid by different recombinant strains of *Candida tropicalis*
Experiment 2

| Strain | Genes Amplified | Average C18:1 Diacid (g/kg) | No. of Expts. | Standard Deviation (%) | % Improvement |
|---|---|---|---|---|---|
| H5343 | — | 13.7 | 2 | 7.7 | 0.0 |
| HDC11-1 | CPR B + Cyt B5 | 17.3 | 2 | 5.7 | 25.7 |
| HDC11-2 | CPR B + Cyt B5 | 21.0 | 2 | 2.4 | 53.2 |
| HDC16-2 | CPR B + CYP52A5A | 16.0 | 2 | 8.4 | 16.3 |
| HDC23-3 | CPR B + CYP52A2A | 23.3 | 2 | 3.9 | 70.1 |

TABLE 9

Bioconversion of octadecane by different recombinant strains of *Candida tropicalis*
Experiments 1 and 2

| Strain | Genes Amplified | Total Product Mono and diacids (g/kg) | Total Product % Improvement | Total Product (Normalized) % Improvement | Total Product % Ave. Improvement |
|---|---|---|---|---|---|
| H5343 | — | 6.6/5.2 | 0.0/0.0 | 0/0 | 0 |
| HDC11-1 | CPR B + CYTb5 | 15.2/10.1 | 130.6/93.5 | 74.3/39.1 | 56.7 ± 17.6 |
| HDC11-2 | CPR B + CYTb5 | 18.2/17 | 175.8/225.7 | 100/94.4 | 97.2 ± 2.8 |
| HDC16-2 | CPR B + CYP52A5A | 17.1/15.2 | 160.1/191.2 | 91.1/79.9 | 85.5 ± 5.6 |
| HDC23-3 | CPR B + CYP52A2A | 8.5/17.7 | 29.8/239.1 | 16.9/100 | 58.5 ± 41.5 |

TABLE 10

Bioconversion of octadecane by different recombinant strains of *Candida tropicalis*
Experiment 3

| Strain | Genes Amplified | Total Product Mono and diacids (g/kg) | Total Product % Improvement |
|---|---|---|---|
| H5343 | — | 11.2 | 0.0 |
| HDC10-2 | CPR B | 22.1 | 98.0 |
| HDC11-2 | CPR B + CYTb5 | 16.1 | 44.3 |
| HDC15 | CYP52A5A | 13.0 | 16.5 |
| HDC16-2 | CPR B + CYP52A5A | 19.4 | 73.8 |

This data demonstrates that diacid production is increased in genetically modified *C. tropicalis* strains HDC11- and HDC11-2 containing an increased copy number of CYTb5/CPRB genes compared with the wild type strain H5343. Diacid production was also increased in genetically modified *C. tropicalis* strains HDC10-2, HDC15, HDC16-2, and HDC23-3.

EXAMPLE 13

Cloning and Characterization of *C. tropicalis* 20336 Cytochrome b5 (CYTb5) and CPR Genes A. Cloning of CYTb5 Gene from *C. tropicalis* 20336

Figure 19:
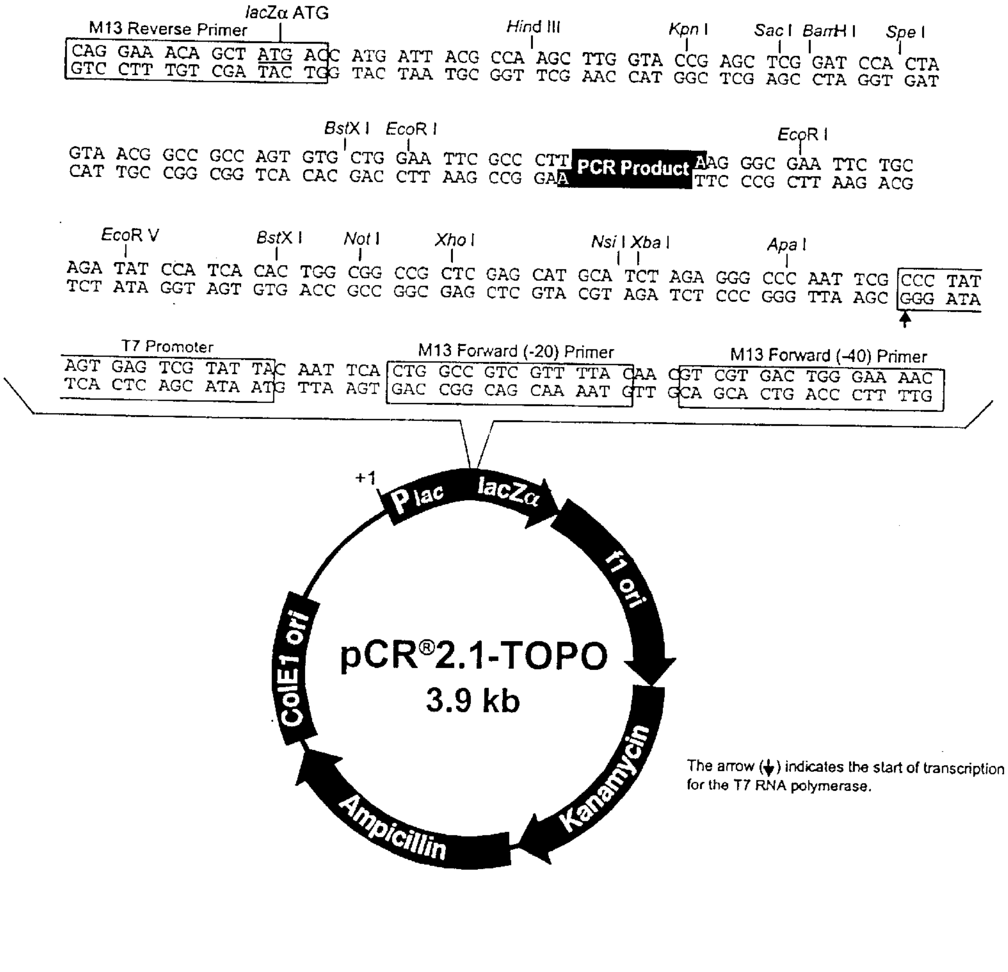
FIG. 19 is schematic representation plasmid pCR2.™ available from Invitrogen. Nucleic acid sequences for selected restriction sites and other features are depicted (SEQ. ID. NO. 43 and complementary strand SEQ. ID. NO. 44).

The CYTb5 gene was isolated from the third genomic library using a PCR fragment as a probe. The PCR fragment probe for CYTb5 was generated after PCR amplification of *Saccharomyces cerevisiae* genomic DNA with oligonucleotide primers that were designed to amplify a region using the available CYTb5 gene of *S. cerevisiae* from the National Center for Biotechnology Information. A forward primer 3698-66A 5' ATAAGAATGCGGCCGCTGAACGAGAACCACATCCAGGAG 3' and a reverse primer 3698-66B 5' CCTTAATTAAGGATAACCACATCCATACGTCGC 3' were made based on the *S. cerevisiae* CYTb5 sequence. These primers were used in pairwise combinations in a PCR reaction with Taq DNA polymerase (Perkin-Elmer Cetus, Foster City, Calif.) according to the manufacturer's recommended procedure. A PCR product of approximately 1036 bp was obtained. This product was purified from agarose gel using Qiaquick (Qiagene, Chatsworth, Calif.) and ligated to the pCR2.1™ vector (FIG. 19, Invitrogen, LaJolla, Calif.) according to the recommendations of the manufacturer. This PCR fragment was used as a probe in isolating the *C. tropicalis* 20336 CYTb5 homolog. The third genomic library was screened using this CYTb5 probe and a clone that contained a full-length CYTb5 gene was obtained. The clone contained a gene having regulatory and protein coding regions (FIGS. 1A–1C). An open reading frame of 387 nucleotides encoded a CYTb5 protein of 129 amino acids (FIGS. 1A–1C).

B. Confirmation of Function of Cloned CYTb5 Gene

CYP51, lanosterol 14α-demethylase, is the site of action for major categories of antifungal agents termed DMI for demethylase inhibitors. Therapeutic agents such as ketoconazole (Kc), an N-substituted imidazole antifungal agent provides a convenient assay for CYP51 activity based on minimum inhibitory concentrations (MIC) as described in Vanden Bossche et al., *Antimicrobial Agents Chemother.* 17:922–928, 1980, which is incorporated herein by reference. *S. cerevisiae* cpr strains deficient in cytochrome P450 reductase (cpr) have been shown to be hypersensitive to Kc, because of a reduction in electron flow to CYP51, the target of Kc as described in Sutter and Loper, supra. Recovery from this hypersensitivity was accomplished by gene cloning based upon transformation of a wild type genomic library on a multicopy vector into a cpr1 strain as described in Truan et al., supra. The gene responsible for this recovery of sensitivity to Kc was shown to be that encoding cytochrome CYTb5, showing that in this system, CYTb5 is able to functionally mimic CPR when present in high copy number.

The inhibition of lanosterol demethylase by a certain concentration of Kc results in the retardation of growth of *S. cerevisiae*. In the absence of CPR, growth inhibition is more pronounced and occurs at a lower concentration of Kc. In the absence of CPR gene, the CYTb5 can suppress the phenotype by serving as the electron donor to CYP51, albeit inefficiently, and partially relieves the growth suppressive effect of Kc. Therefore, the recombinant *S. cerevisiae* containing a *C. tropicalis* CYTb5 will be able to grow on a medium containing intermediate levels of Kc. This test was used to confirm that the cloned *C. tropicalis* gene codes for CYTb5.

Figure 20:
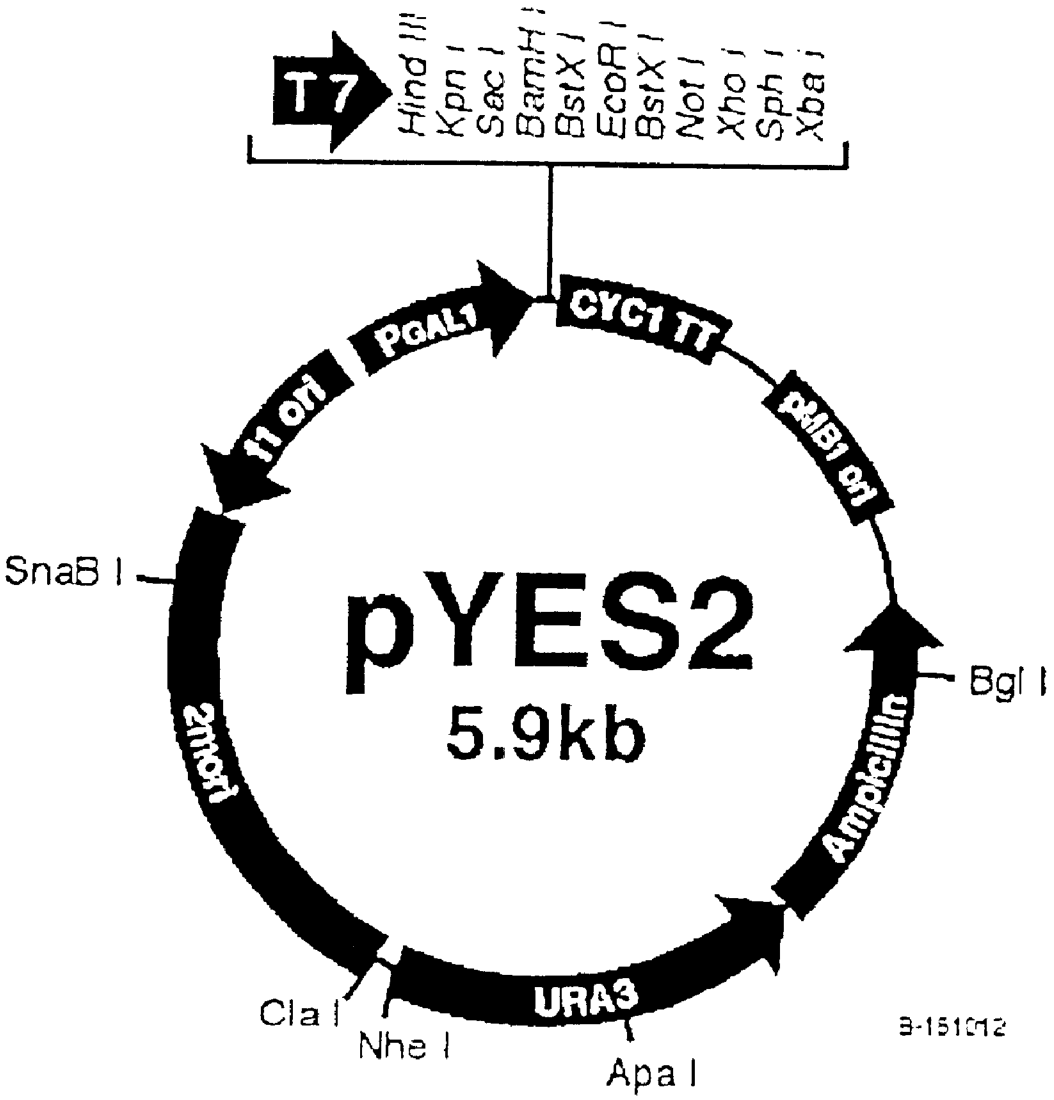
FIG. 20 is a schematic representation of S. cerevisiae expression vector pYES 2.0 available from Invitrogen. Selected restriction sites are indicated.

The putative CYTb5 gene was cloned under the control of a GAL promoter present in the *S. cerevisiae* expression vector pYES 2.0 (FIG. 20, Invitrogen, Carlsbad, Calif.) after PCR amplification of the open reading frame. The expression vector containing CYTb5 was introduced into a *S. cerevisiae* mutant DC10 containing a disrupted CPR gene and the recombinant strain was plated on minimal medium containing different concentrations of Kc. The DC10 strain containing the wild-type *S. cerevisiae* CPR gene (on plasmid pTS20) and of *C. tropicalis* CYTb5 gene (on plasmid pYES2b5) was able to grow on minimal medium containing 0.078 mg/ml of Kc. On the other hand, DC10 carrying pYES2.0 without any insert was unable to grow at concentrations of 0.039 mg/ml of Kc. The recombinant strains were tested in liquid cultures to confirm the results from plates. While the DC10 containing pYES2.0 without any insert was able to grow at 0.0024 mg/ml of Kc, the DC10 expressing b5 from GAL promoter was resistant to 0.0098 mg/ml of Kc. This confirmed that the cloned gene coded for CYTb5 enzyme.

C. Cloning and Characterization of the CPR Genes from *C. tropicalis* 20336

To clone CPR a heterologous probe based upon the known DNA sequence for the CPR gene from *C. tropicalis* 750 was used to isolate the *C. tropicalis* 20336 CPR gene.

1) Cloning of the CPRA Allele

Approximately 25,000 phage particles from the first genomic library of *C. tropicalis* 20336 were screened with a 1.9 kb BamHI-NdeI fragment from plasmid pCU3RED (See Picattagio et al., Bio/Technology 10:894–898 (1992), incorporated herein by reference, containing most of the *C. tropicalis* 750 CPR gene. Five clones that hybridized to the probe were isolated and the plasmid DNA from these lambda clones was rescued and characterized by restriction enzyme analysis. The restriction enzyme analysis suggested that all five clones were identical but it was not clear that a complete CPR gene was present.

Figure 21:
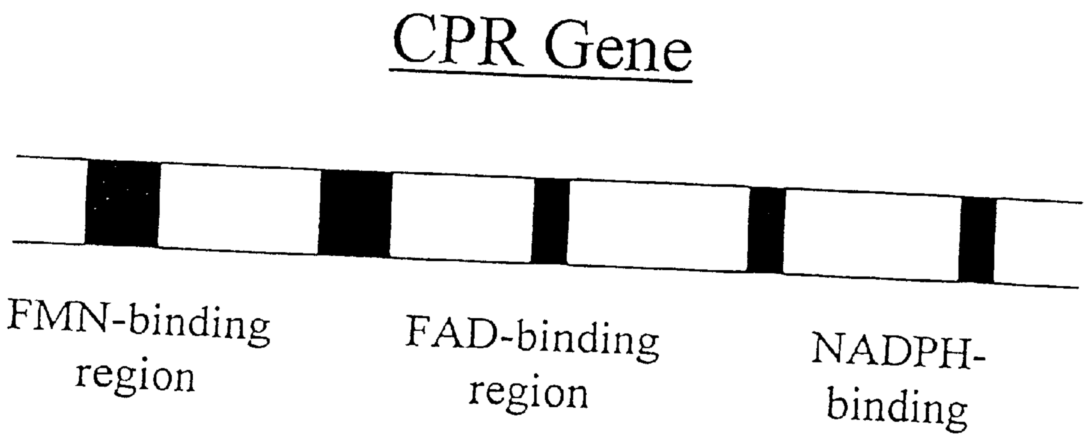
FIG. 21 is a schematic representation of certain conserved portions of certain CPR genes.
Figure 22:
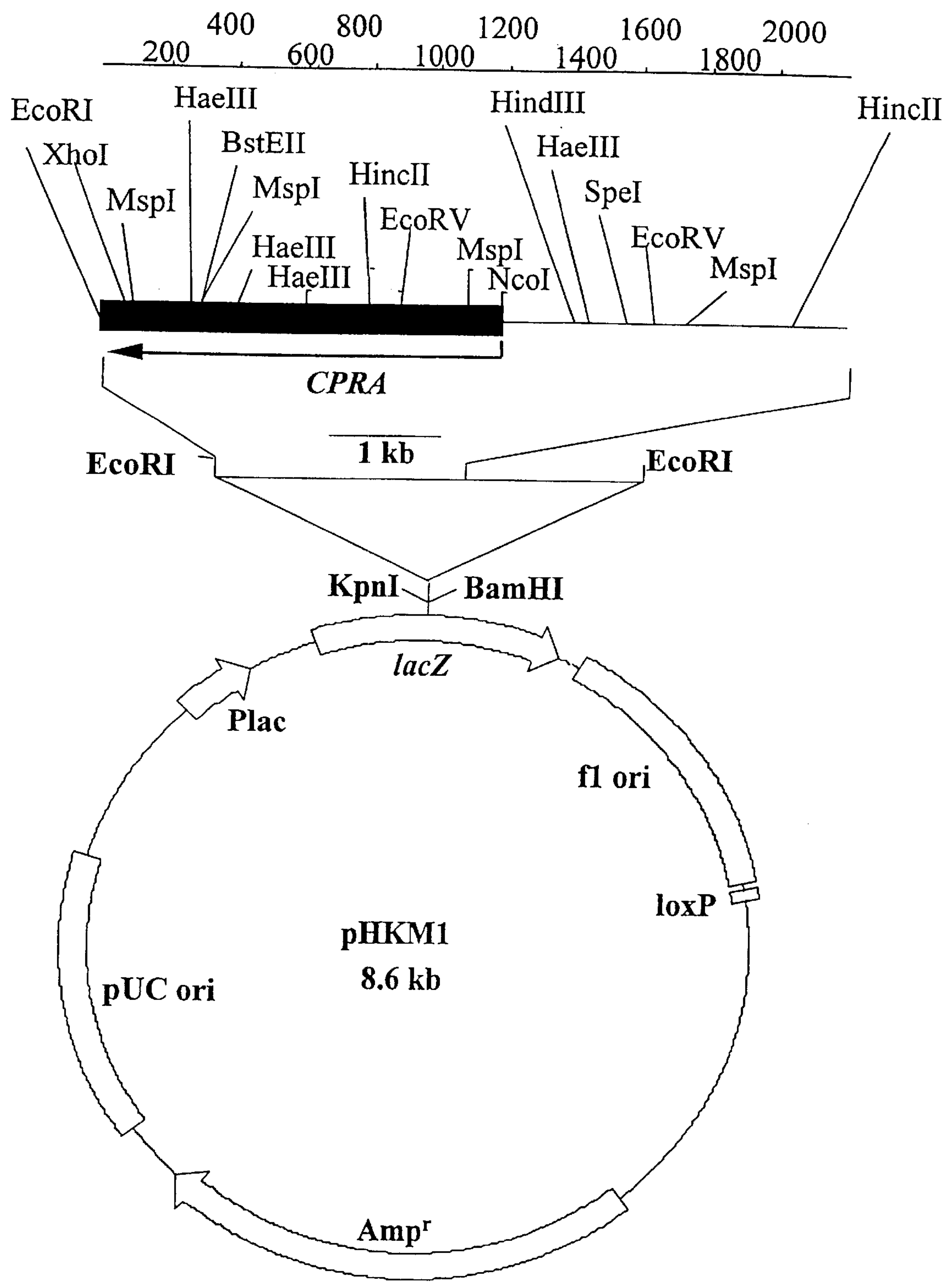
FIG. 22 is a schematic representation of plasmid pHKM1. Selected restriction sites are indicated as well as the position of the CPRA gene.

PCR analysis was used to determine if a complete CPR gene was present in any of the five clones. Degenerate primers were prepared for highly conserved regions of known CPR genes (See Sutter et al., *J. Biol. Chem.* 265:16428–16436, 1990, incorporated herein by reference) (FIG. 21). Two Primers were synthesized for the FMN binding region (FMN1 and FMN2). One primer was synthesized for the FAD binding region (FAD), and one primer for the NADPH binding region (NADPH) (Table 4). These four primers were used in PCR amplification experiments using as a template plasmid DNA isolated from four of the five clones described above. The FMN and FAD primers served as forward primers and the NADPH primer as the reverse primer in the PCR reactions. When different combinations of forward and reverse primers were used, no PCR products were obtained from any of the plasmids. However, all primer combinations amplified expected size products with a plasmid containing the *C. tropicalis* 750 CPR gene (positive control). The most likely reason for the failure of the primer pairs to amplify a product, was that all four of clones contained a truncated CPR gene. One of the four clones (pHKM1) was sequenced using the Triplex 5' and the Triplex 3' primers (Table 4) which flank the insert and the multiple cloning site on the cloning vector, and with the degenerate primer based upon the NADPH binding site described above. The NADPH primer failed to yield any sequence data and this is consistent with the PCR analysis. Sequences obtained with Triplex primers were compared with *C. tropicalis* 750 CPR sequence using the MacVector™ program (Oxford Molecular Group, Campbell, Calif.). Sequence obtained with the Triplex 3' primer showed similarity to an internal sequence of the *C. tropicalis* 750 CPR gene confirming that pHKM1 contained a truncated version of a 20336 CPR gene. pHKM1 had a 3.8 kb insert which included a 1.2 kb coding region of the CPR gene accompanied by 2.5 kb of upstream DNA (FIG. 22). Approximately 0.85 kb of the 20336 CPR gene encoding the C-terminal portion of the CPR protein is missing from this clone.

Figure 23:
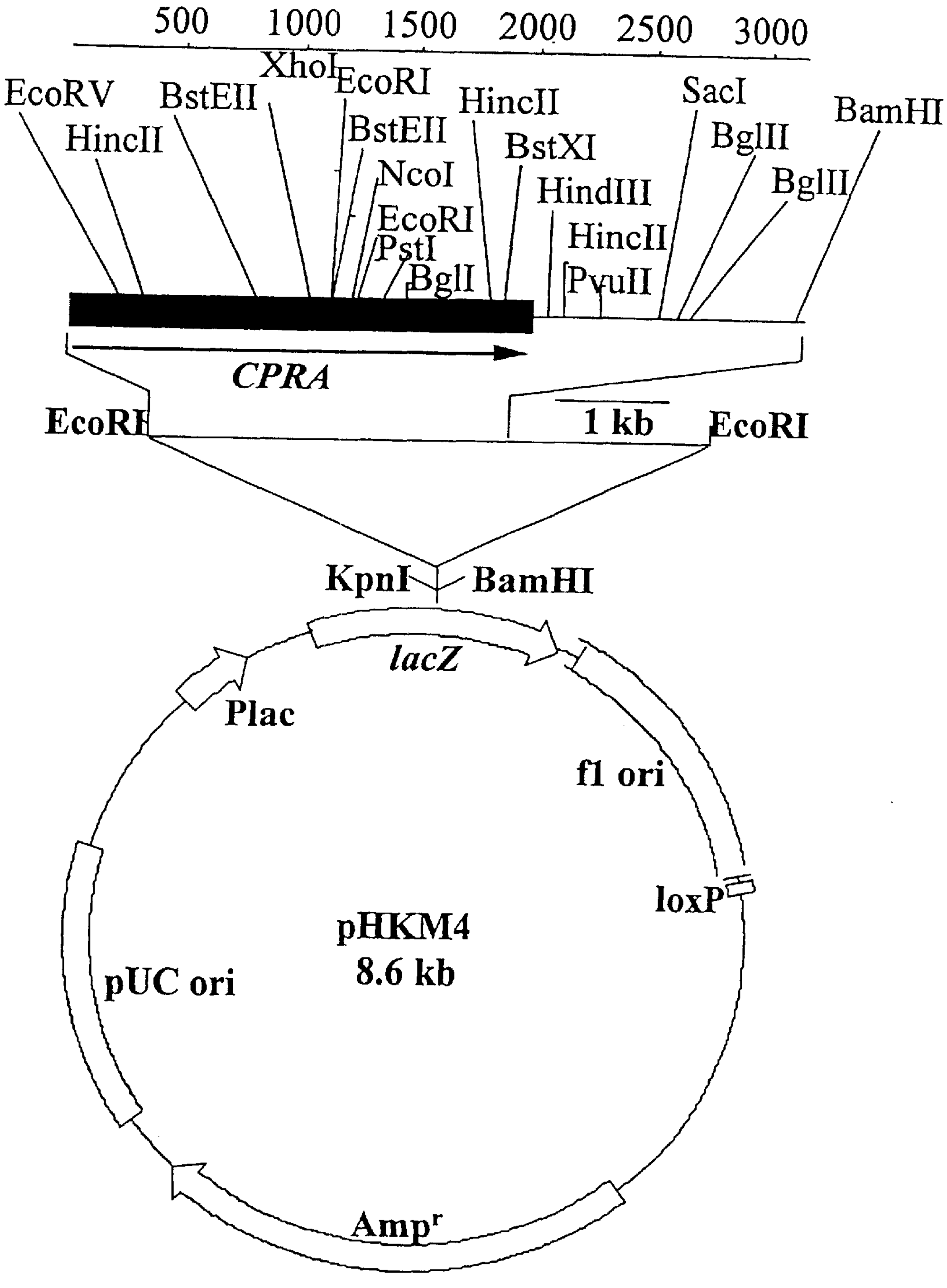
FIG. 23 is a schematic representation of plasmid pHKM4. Selected restriction sites are indicated as well as the position of the CPRA gene.

Since the first Clontech library yielded only a truncated CPR gene, the second library prepared by Clontech was screened to isolate a full-length CPR gene. Three putative CPR clones were obtained. The three clones, having inserts in the range of 5–7 kb, were designated pHKM2, pHKM3 and pHKM4. All three were characterized by PCR using the degenerate primers described above. Both pHKM2 and pHKM4 gave PCR products with two sets of internal primers. pHKM3 gave a PCR product only with the FAD and NADPH primers suggesting that this clone likely contained a truncated CPR gene. All three plasmids were partially sequenced using the two Triplex primers and a third primer whose sequence was selected from the DNA sequence near the truncated end of the CPR gene present in pHKM1. This analysis confirmed that both pHKM2 and 4 have sequences that overlap pHKM1 and that both contained the 3' region of CPR gene that is missing from pHKM1. Portions of inserts from pHKM1 and pHKM4 were sequenced and a full-length CPR gene was identified. Based on the DNA sequence and PCR analysis, it was concluded that pHKM1 contained the putative promoter region and 1.2 kb of sequence encoding a portion (5' end) of a CPR gene. pHKM4 had 1.1 kb of DNA that overlapped pHKM1 and contained the remainder (3' end) of a CPR gene along with a downstream untranslated region (FIG. 23). Together these two plasmids contained a complete CPRA gene with an upstream promoter region. CPRA is 4206 nucleotides in length and includes a regulatory region and a protein coding region (defined by nucleotides 1006–3042) which is 2037 base pairs in length and codes for a putative protein of 679 amino acids (FIGS. 2A–2B and 3A–3C, respectively). The CPRA protein, when analyzed by the protein alignment program of the GeneWorks™ software package (Oxford Molecular Group, Campbell, Calif.), showed extensive homology to CPR proteins from *C. tropicalis* 750 and *C. maltosa.*

2) Cloning of the CPRB Allele

Figure 24:
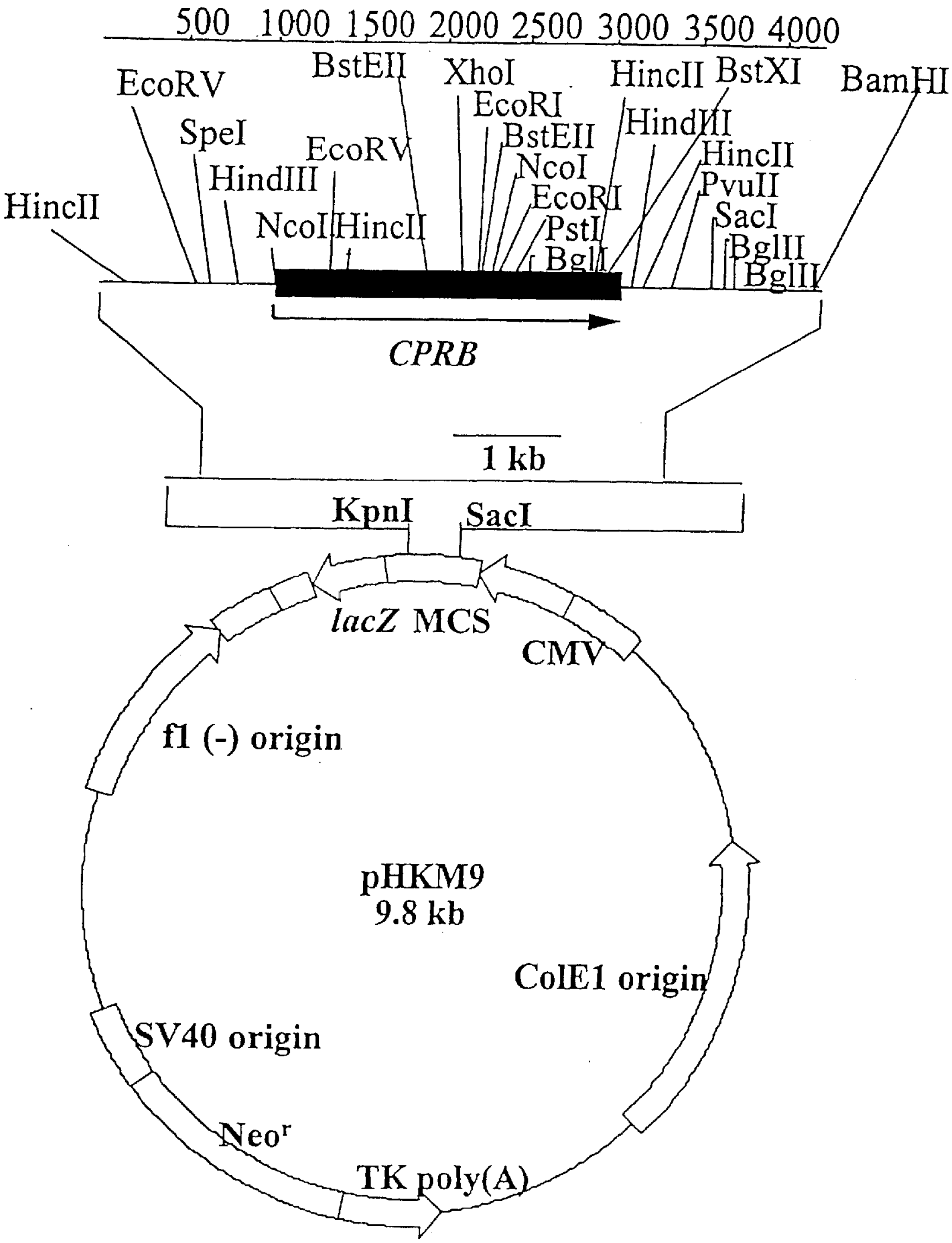
FIG. 24 is a schematic representation of plasmid pHKM9. Selected restriction sites are indicated as well as the position of the CPRB gene.

To clone the second CPR allele, the third genomic library, prepared by Henkel, was screened using DNA fragments from pHKM1 and pHKM4 as probes. Five clones were obtained and these were sequenced with the three internal primers used to sequence CPRA. These primers were designated PRK1.F3, PRK1.F5 and PRK4.R20 (Table 4) and the two outside primers (M13–20 and T3 [Stratagene]) for the polylinker region present in the pBK-CMV cloning vector. Sequence analysis suggested that four of these clones, designated pHKM5 to 8, contained inserts which were identical to the CPRA allele isolated earlier. All four seemed to contain a full length CPR gene. The fifth clone was very similar to the CPRA allele, especially in the open reading frame region where the identity was very high. However, there were significant differences in the 5' and 3' untranslated regions. This suggested that the fifth clone was the allele to CPRA. The plasmid was designated pHKM9 (FIG. 24) and a 4.14 kb region of this plasmid was sequenced and the analysis of this sequence confirmed the presence of the CPRB allele, which includes a regulatory region and a protein coding region (defined by nucleotides 1033–3069) as shown in FIGS. 4A–4B. The amino acid sequence of the CPRB protein is shown in FIGS. 5A–5C.

EXAMPLE 14

Figure 25:
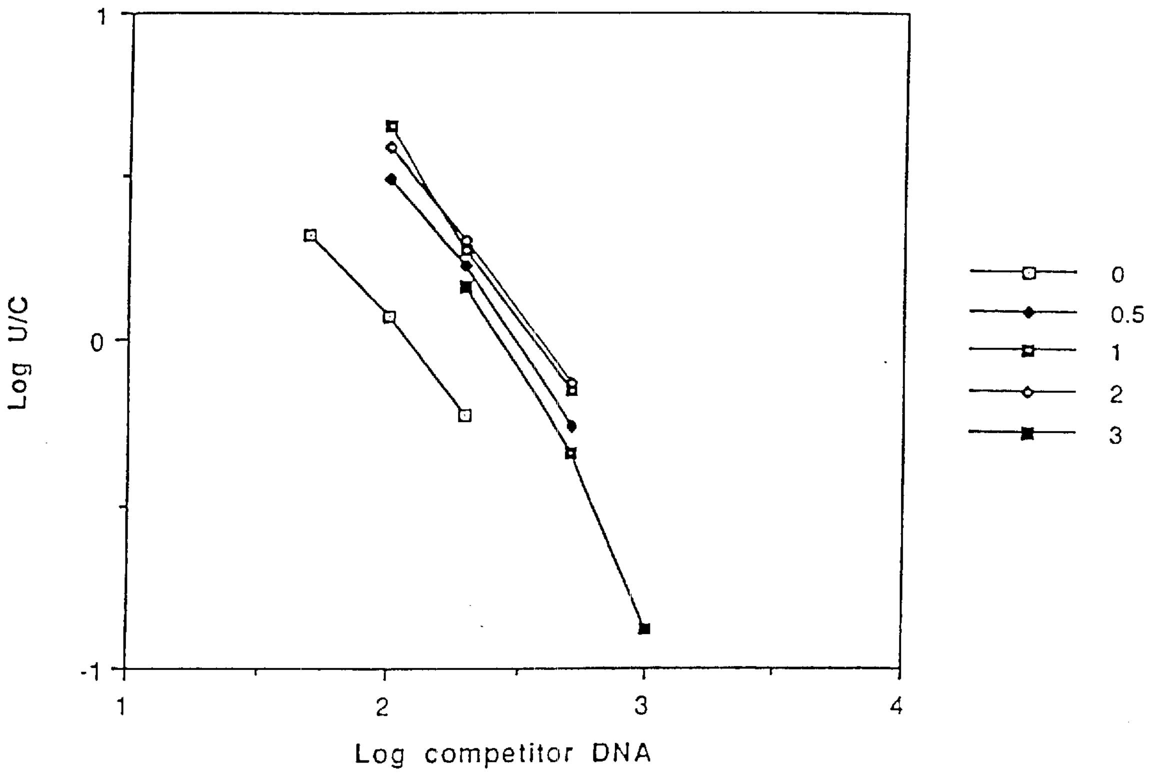
FIG. 25 is a graphic depiction of the log ratio of unknown (u) to competitor (c) product versus the concentration of competitor RNA in QC-RT-PCR reactions relating to CYTb5.

Identification of CYTb5 Gene Induced by Selected Fatty Acid and Alkane Substrates Genes whose transcription is turned on by the presence of selected fatty acid or alkane substrates have been identified using the QC-RT-PCR assay. This assay was used to measure CYTb5 gene expression in fermentor grown cultures *C. tropicalis* ATCC 20962. This method involves the isolation of total cellular RNA from cultures of *C. tropicalis* and the quantification of a specific mRNA within that sample through the design and use of sequence specific QC-RT-PCR primers and an RNA competitor. Quantification is achieved through the use of known concentrations of highly homologous competitor RNA in the QC-RT-PCR reactions. The resulting QC-RT-PCR amplified cDNA's are separated and quantitated through the use of ion pairing reverse phase HPLC. This assay was used to characterize the expression of the CYTb5 gene of *C. tropicalis* ATCC 20962 in response to fatty acid and alkane substrates. Genes which were induced were identified by the calculation of their mRNA concentration at various times before and after induction. FIG. 25 provides an example of how the concentration of mRNA for CYTb5 can be calculated using the QC-RT-PCR assay. The log ratio of unknown (U) to competitor product (C) is plotted versus the concentration of competitor RNA present in the QC-RT-PCR reactions. The concentration of competitor which results in a log ratio of U/C of zero, represents the point where the unknown messenger RNA concentration is equal to the concentration of the competitor. FIG. 25 allows for the calculation of the amount of CYTb5 message present in 100 ng of total RNA isolated from cell samples taken at 0, 0.5, 1, 2, and 3 hours after the addition of Emersol® in a fermentor run. From this analysis, it is possible to determine the concentration of the CYTb5 mRNA present in 100 ng of total cellular RNA. In the plot contained in FIG. 25 it takes 113.75 pg of competitor to equal the number of mRNA's of CYTb5 in 100 ng of RNA isolated from cells just prior (time 0) to the addition of the substrate, Emersol®. In cell samples taken at 0.5, 1, 2, and 3 hours after the addition of Emersol® it takes 293.69, 356.01, 372.24, and 264.61 pg of competitor RNA, respectively. The results obtained during this fermentation run as measured by QC-RT-PCR are also expressed as relative induction of CYTb5 gene as shown in Table 11 below.

TABLE 11

Relative Induction of CYTb5 Gene by Emersol ®

| Time (hr.) | Relative induction of Cytb5 Gene |
|---|---|
| 0 | 1 |
| 0.5 | 2.5 |
| 1 | 3.1 |
| 2 | 3.3 |
| 3 | 2.3 |

These data demonstrate that CYTb5 is induced more than 3.0 fold within one hour after the addition of Emersol®. This analysis clearly demonstrates that expression of CYTb5 in *C. tropicalis* 20962 is inducible by the addition of Emersol® to the growth medium.

EXAMPLE 15

Integration of Selected CYTb5 and CPRB Genes into the Genome of *Candida tropicalis*

Figure 26:
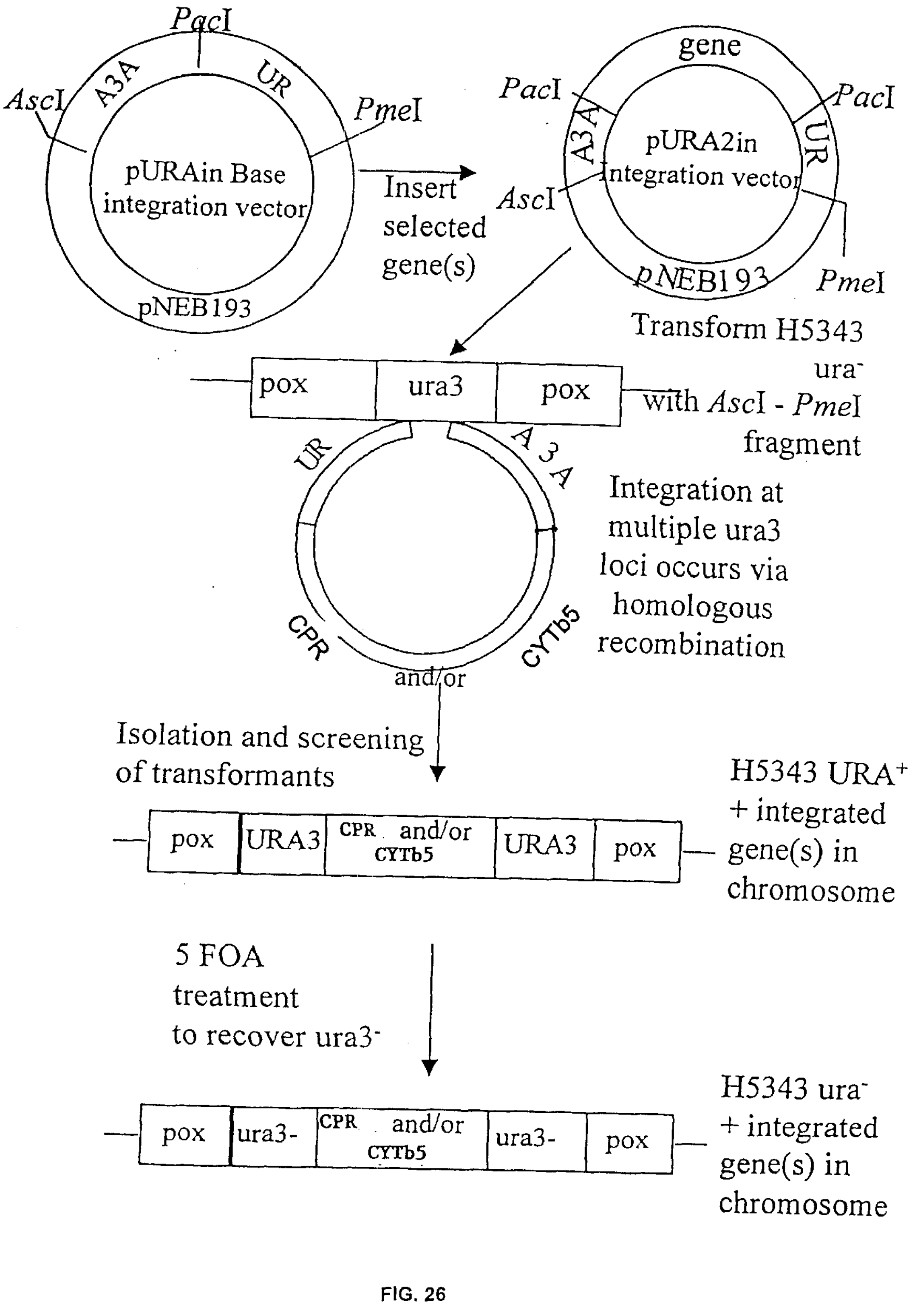
FIG. 26 is a schematic depiction of a procedure for regenerating a URA3A genotype via homologous recombination involving CYTb5 and/or CPR genes.
Figure 27:
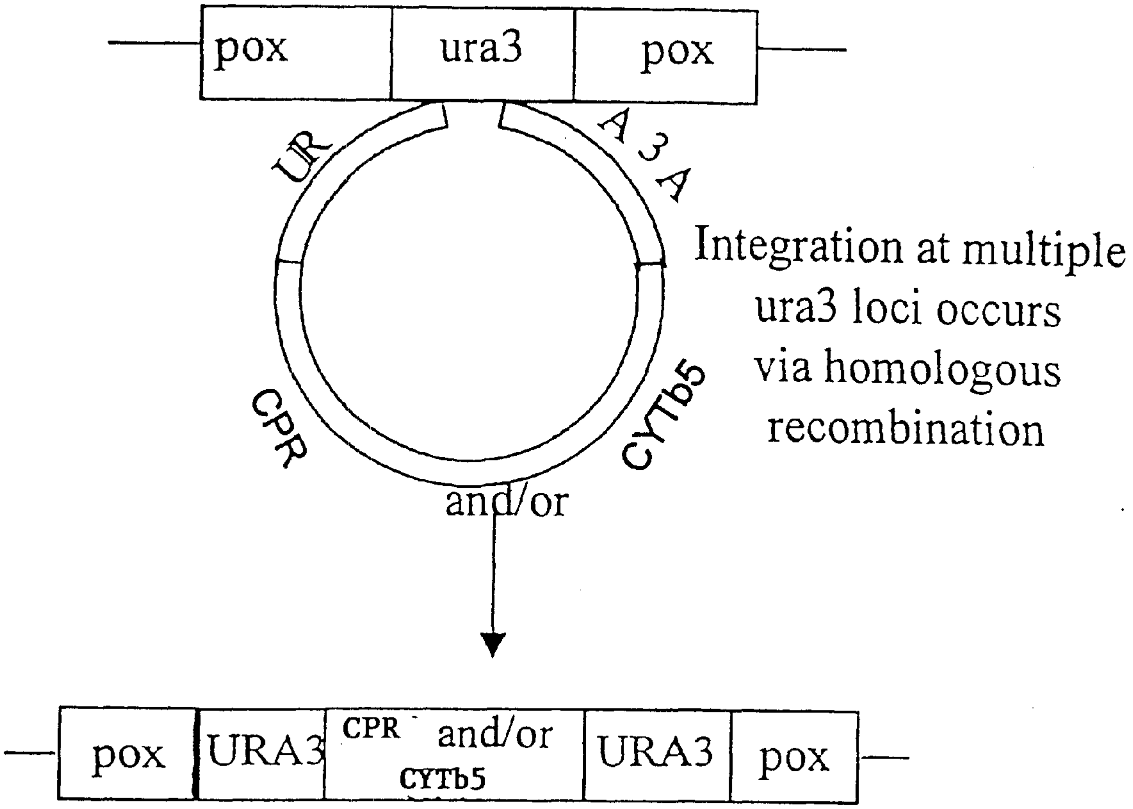
FIG. 27 is a schematic depiction of homologous recombination involving a split URA3A gene and incorporation of CPR and/or CYTb5 genes.

In order to integrate selected genes into the chromosome of *C. tropicalis* 20336 or its descendants, there has to be a target DNA sequence, which may or may not be an intact gene, into which the genes can be inserted. There must also be a method to select for the integration event. In some cases the target DNA sequence and the selectable marker are the same and, if so, then there must also be a method to regain use of the target gene as a selectable marker following the integration event. In *C. tropicalis* and its descendants, one gene which fits these criteria is URA3A, encoding orotidine-5'-phosphate decarboxylase. Using it as a target for integration, ura$^-$ variants of *C. tropicalis* can be transformed in such a way as to regenerate a URA$^+$ genotype via homologous recombination (FIG. 26). Depending upon the design of the integration vector, one or more genes can be integrated into the genome at the same time. Using a split URA3A gene oriented as shown in FIG. 27, homologous integration would yield at least one copy of the gene(s) of interest which are inserted between the split portions of the URA3A gene. Moreover, because of the high sequence similarity between URA3A and URA3B genes, integration of the construct can occur at both the URA3A and URA3B loci. Subsequently, an oligonucleotide designed with a deletion in a portion of the URA gene based on the identical sequence across both the URA3A and URA3B genes, can be utilized to yield *C. tropicalis* transformants which are once again ura$^-$ but which still carry one or more newly integrated genes of choice (FIG. 26). Ura$^-$ variants of *C. tropicalis* can also be isolated via other methods such as classical mutagenesis or by spontaneous mutation. Using well established protocols, selection of ura$^-$ strains can be facilitated by the use of 5-fluoroorotic acid (5-FOA) as described, e.g., in Boeke et al., *Mol. Gen. Genet.* 197:345–346 (1984), incorporated herein by reference. The utility of this approach for the manipulation of *C. tropicalis* has been well documented as described, e.g., in Picataggio et al., *Mol. and Cell. Biol.* 11:4333–4339 (1991); Rohrer et al., *Appl. Microbiol. Biotechnol.* 36:650–654 (1992); Picataggio et al., *Bio/Technology* 10:894–898 (1992); U.S. Pat. Nos. 5,648,247; 5,620,878; 5,204,252; 5,254,466, all of which are incorporated herein by reference.

A. Construction of a URA Integration Vector, pURAin

Figure 29:
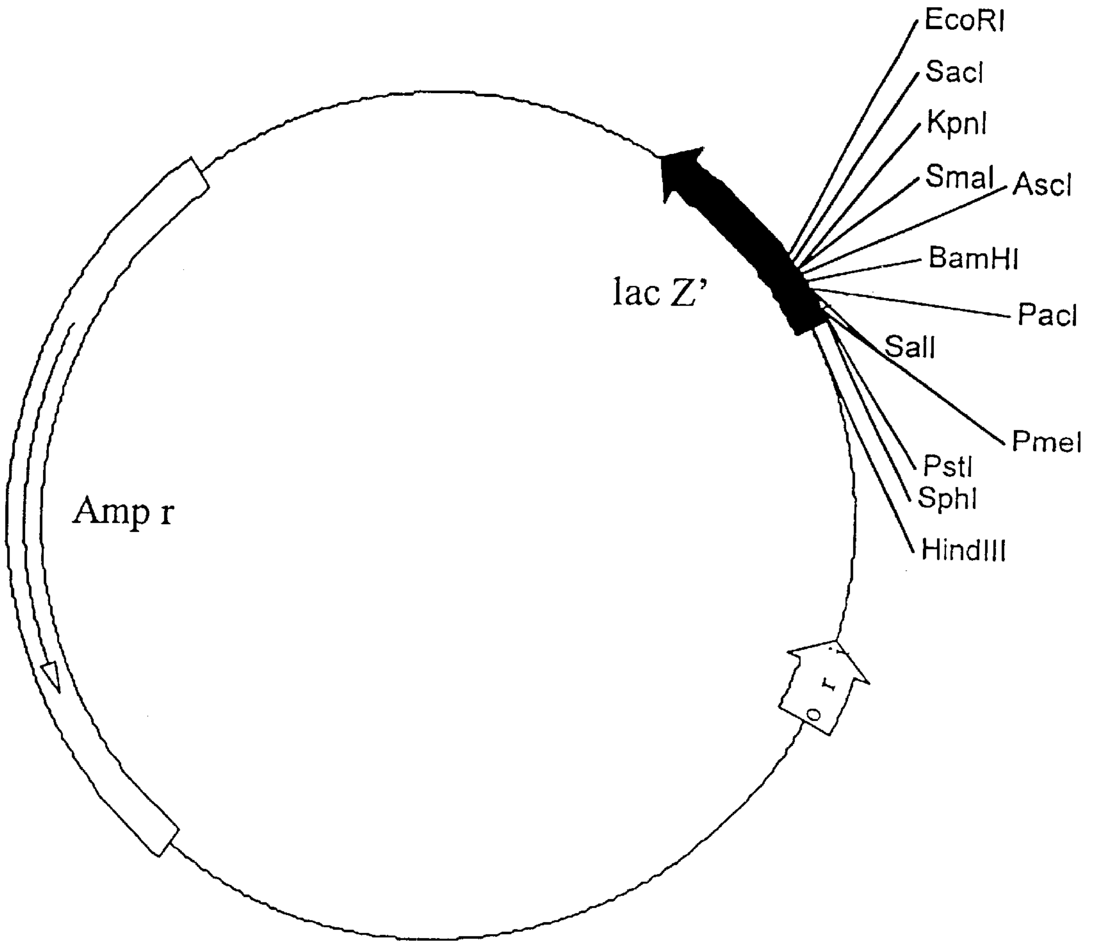
FIG. 29 is a schematic depiction of plasmid pNEB193 available from New England Biolabs. Selected restriction sites are indicated.
Figure 30:
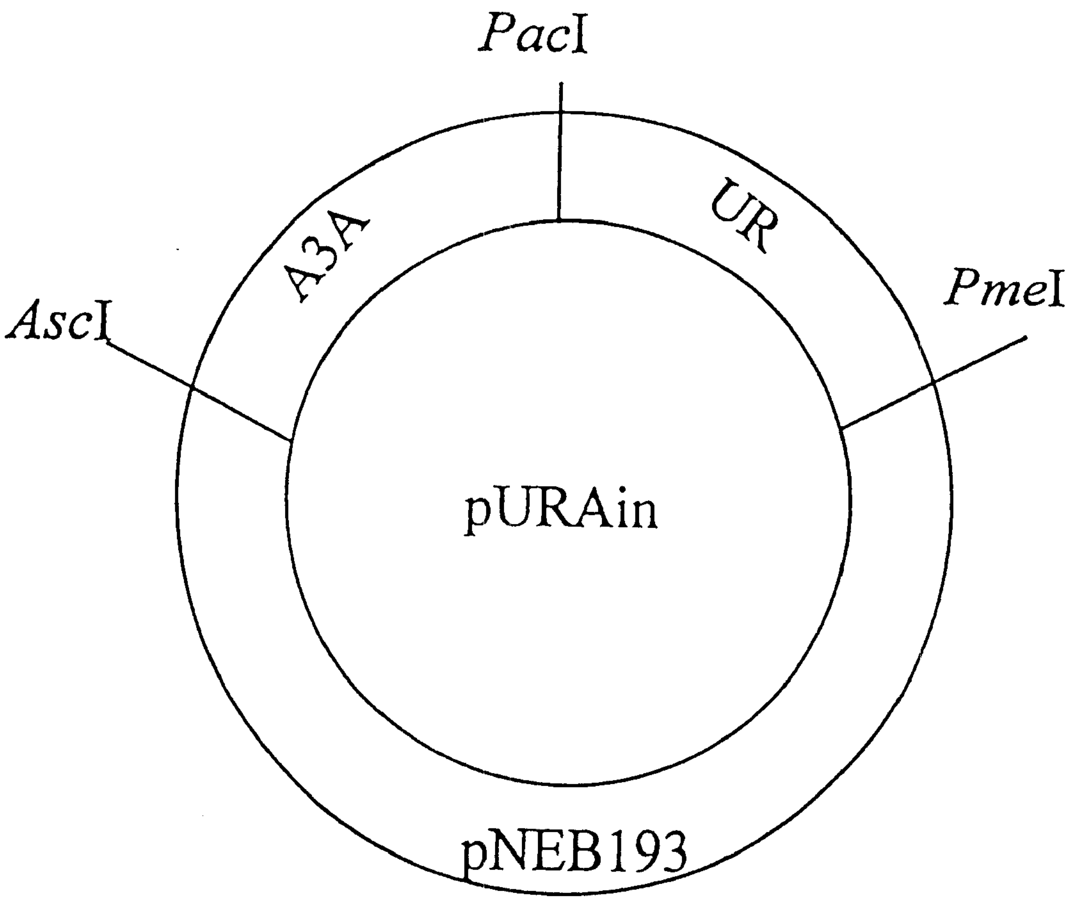
FIG. 30 is a schematic depiction of integration vector pURAin containing modified URA3A in the pNEB193 plasmid.

Primers were designed and synthesized based on the 1712 bp sequence of the URA3A gene of *C. tropicalis* 20336 (see FIG. 28). URA3A Primer Set #1a and #1b (Table 4) was used in PCR with *C. tropicalis* 20336 genomic DNA to amplify URA3A sequences between nucleotide 733 and 1688 as shown in FIG. 28. The primers are designed to introduce unique 5' AscI and 3' PacI restriction sites into the resulting amplified URA3A fragment. AscI and PacI sites were chosen because these sites are not present within CYTb5 or CPRB gene. URA3A Primer Set #2 was used in PCR with *C. tropicalis* 20336 genomic DNA as a template, to amplify URA3A sequences between nucleotide 9 and 758 as shown in FIG. 27. URA3A Primer set #2a and #2b (Table 4) was designed to introduce unique 5' PacI and 3'PmeI restriction sites into the resulting amplified URA3A fragment. The PmeI site is also not present within CYTb5 and CPRB genes. PCR fragments of the URA3A gene were purified, restricted with AscI, PacI and PmeI restriction enzymes and ligated to a gel purified, QiaexII cleaned AscI-PmeI digest of plasmid pNEB193 (FIG. 29) purchased from New England Biolabs (Beverly, Mass.). The ligation was performed with an equimolar number of DNA termini at 16° C. for 16 hr using T4 DNA ligase (New England Biolabs). Ligations were transformed into *E. coli* XL1-Blue cells (Stratagene, LaJolla, Calif.) according to manufacturers recommendations. White colonies were isolated, grown, plasmid DNA isolated and digested with AscI-PmeI to confirm insertion of the modified URA3A into pNEB193. The resulting base integration vector was named pURAin (FIG. 30).

B. Amplification of CYTb5 and CPRB from *C. tropicalis* 20336 Genomic DNA

The gene encoding CYTb5 was amplified via PCR using primers (Primer CYT b5#1, GGGTTAATTAACATACTTCAAGCAGTTTGG; and Primer CYT b5#2, CCCTTAATTAAGGGGGGATGGAAGTGGCCG) to introduce PacI cloning sites. See Table 4. These PCR primers were designed based upon the DNA sequence determined for CYTb5. The Ultma PCR kit (Perkin Elmer Cetus, Foster City, Calif.) was used according to manufacturers specifications. The CYTb5 PCR amplification product was 1998 base pairs in length, yielding 1088 bp of DNA upstream of the CYTb5 start codon and 486 bp downstream of the stop codon for the CYTb5 ORF. In order to generate an error-free PCR product for cloning, an internal BglII fragment from one PCR was replaced with a BglII fragment from a different PCR which contained no mutations in the region. A final error-free CYT b5 product was generated that contained PacI sensitive cloning sites.

The gene encoding CPRB from *C. tropicalis* 20336 was amplified from genomic DNA via PCR using primers (CPR B#1 and CPR B#2) based upon the DNA sequence determined for CPRB (FIGS. 4A–4B). These primers were designed to introduce unique PacI cloning sites. The Expand Hi-Fi Taq PCR kit (Boehringer Mannheim, Indianapolis, Ind.) was used according to manufacturers specifications. The CPRB PCR product was 3266 bp in length, yielding 747 bp pf DNA upstream of the CPRB start codon and 493 bp downstream of the stop codon for the CPRB ORF. The resulting PCR products were isolated via agarose gel electrophoresis, purified using QiaexII and digested with PacI. The PCR fragments were purified, desalted and concentrated using a Microcon 100 (Amicon, Beverly, Mass.).

The above described amplification procedures are also applicable to the CPRA gene (FIGS. 2A–2B) using the respectively indicated primers (see Table 4).

C. Cloning of CPRB Gene into pURAin

The next step was to clone the CPRB gene into the pURAin integration vector. In a preferred aspect of the present invention, no foreign DNA other than that specifically provided by synthetic restriction site sequences are incorporated into the DNA which was cloned into the genome of *C. tropicalis,* i.e., with the exception of restriction site DNA only native *C. tropicalis* DNA sequences are incorporated into the genome. pURAin was digested with PacI, Qiaex II cleaned, and dephosphorylated with Shrimp Alkaline Phosphatase (SAP) (United States Biochemical, Cleveland, Ohio) according the manufacturer's recommendations. Approximately 500 ng of PacI linearized pURAin was dephosphorylated for 1 hr at 37° C. using SAP at a concentration of 0.2 Units of enzyme per 1 pmol of DNA termini. The reaction was stopped by heat inactivation at 65° C. for 20 min.

Prior to its use, the CPRB PacI fragment derived using the primers shown in Table 4 was sequenced and compared to CPRB to confirm that PCR did not introduce DNA base pair changes that would result in an amino acid change. Following confirmation, CPRB was ligated to plasmid pURAin which had also been digested with PacI. PacI digested pURAin was dephosphorylated, and ligated to the CPR Expand Hi-Fi PCR product as described previously. The ligation mixture was transformed into *E. coli* XL1 Blue MRF' (Stratagene) and several resistant colonies were selected and screened for correct constructs which should contain vector sequence, the inverted URA3A gene, and the amplified CPRB gene (FIGS. 4A–4B) of 20336. AscI-PmeI digestion confirmed a successful construct, pURAREDBin.

In a manner similar to the above, the CPRA gene disclosed herein is cloned in the pURAin. PacI fragment of the CPRA gene, whose nucleotide sequence is given in FIGS. 2A–2B, is derivable by methods known to those skilled in the art.

1) Construction of Vectors Used to Generate HDC11

The previously constructed integration vector containing CPRB, pURAREDBin, was chosen as the starting vector. This vector was partially digested with PacI and the linearized fragment was gel-isolated. The active PacI was destroyed by treatment with T4 DNA polymerase and the vector was re-ligated. Subsequent isolation and complete digestion of this new plasmid yielded a vector now containing only one active PacI site. This fragment was gel-isolated, dephosphorylated and ligated to the CYTb5 PacI fragment. Vectors that contain the CYTb5 and CPRB genes oriented in the opposite directions (5' ends connected), pURAin CPR b5 O, were generated.

D. Confirmation of CYTb5 Integration into the Genome of *C. tropicalis*

Based on the construct, pURAin CPR b5 0, used to transform H5343 ura-, a scheme to detect integration was devised. Genomic DNA from transformants was digested with Dra III which is an enzyme that cuts within the URA3A, URA3B, CPRB and CYTb5 genes. Digestion of genomic DNA where an integration had occurred at the URA3A locus would be expected to result in a elucidation of a 3.6 Kb fragment upon Southern hybridization with a CPRB probe. Southern hybridizations of this digest with fragments of the CPRB gene were used to screen for these integration events. Intensity of the band signal from the Southern was used as a measure of the number of integration events (i.e. the more copies of the CYTb5 gene which are present, the stronger the hybridization signal).

*C. tropicalis* H5343 transformed URA prototrophs were grown at 30° C., 170 rpm, in 10 ml SC-uracil media for preparation of genomic DNA. Genomic DNA was isolated by the method described previously. Genomic DNA was digested with DraIII. A 0.95% agarose gel was used to prepare a Southern hybridization blot. The DNA from the gel was transferred to a MagnaCharge nylon filter membrane (MSI Technologies, Westboro, Mass.) according to the alkaline transfer method of Sambrook et al., supra. For the Southern hybridization, a 3.3 Kb CPRB DNA fragment was used as a hybridization probe. 300 ng of CPRB DNA was labeled using a ECL Direct labeling and detection system (Amersham) and the Southern was processed according to the ECL kit specifications. The blot was processed in a volume of 30 ml of hybridization fluid corresponding to 0.125 ml/cm$^2$. Following a prehybridization at 42° C. for 1 hr, 300 ng of CPRB probe was added and the hybridization continued for 16 hr at 42° C. Following hybridization, the blots were washed two times for 20 min each at 42° C. in primary wash containing urea. Two 5 min secondary washes at room temperature were conducted, followed by detection according to directions. The blots were exposed for 16 hours (hr) as recommended.

Integration was confirmed by the detection of a DraIII 3.6 Kb fragment from the genomic DNA of the transformants but not with the *C. tropicalis* 20336 control. The resulting CYTb5 and CPRB integrated strain was named HDC11. Variants of this strain were arbitrarily designated 11-1 through 11-4 based on the relative number of integration events that occurred. When compared with the parent H5343, HDC 11-1, HDC11-3 and HDC11-4 each contained a single additional copy of the CYTb5 gene and HDC11-2 contained two additional copies of the CYTb5 gene.

APPENDIX

| | | | |
|---|---|---|---|
| Media Composition | | Distilled Water | 1,000 ml |
| LB Broth | | NZCYM Top Agarose | |
| Bacto Tryptone | 10 g | Bacto Casein Digest | 10 g |
| Bacto Yeast Extract | 5 g | Bacto Casamino Acids | 1 g |
| Sodium Chloride | 10 g | Bacto Yeast Extract | 5 g |
| Distilled Water | 1,000 ml | Sodium Chloride | 5 g |
| | | Magnesium Sulfate | 0.98 g |
| LB Agar | | (anhydrous) | |
| Bacto Tryptone | 10 g | Agarose | 7 g |
| Bacto Yeast Extract | 5 g | Distilled Water | 1,000 ml |
| Sodium Chloride | 10 g | YEPD Broth | |
| Agar | 15 g | Bacto Yeast Extract | 10 g |
| Distilled Water | 1,000 ml | Bacto Peptone | 20 g |
| | | Glucose | 20 g |
| LB Top Agarose | | Distilled Water | 1,000 ml |
| Bacto Tryptone | 10 g | YEPD Agar* | |
| Bacto Yeast Extract | 5 g | Bacto Yeast Extract | 10 g |
| Sodium Chloride | 10 g | Bacto Peptone | 20 g |
| Agarose | 7 g | Glucose | 20 g |
| Distilled Water | 1,000 ml | Agar | 20 g |
| | | Distilled Water | 1,000 ml |
| NZCYM Broth | | YNB | |
| Bacto Casein Digest | 10 g | Yeast extract | 3 g/L |
| Bacto Casamino Acids | 1 g | Maltose | 3 g/L |
| Bacto Yeast Extract | 5 g | Peptone | 5 g/L |
| Sodium Chloride | 5 g | Dextrose | 10 g/L |
| Magnesium Sulfate | 0.98 g | SC-uracil* | |
| (anhydrous) | | Bacto-yeast nitrogen base without amino acids | 6.7 g |
| Distilled Water | 1,000 ml | Glucose | 20 g |
| NZCYM Agar | | Bacto-agar | 20 g |
| Bacto Casein Digest | 10 g | Drop-out mix | 2 g |
| Bacto Casamino Acids | 1 g | Distilled water | 1,000 ml |
| Bacto Yeast Extract | 5 g | | |
| Sodium Chloride | 5 g | | |
| Magnesium Sulfate | 0.98 g | | |
| (anhydrous) | | | |
| Agar | 15 g | | |
| DCA2 medium | g/l | | |
| Peptone | 3.0 | | |
| Yeast Extract | 6.0 | | |
| Sodium Acetate | 3.0 | | |
| Yeast Nitrogen Base (Difco) | 6.7 | | |
| Glucose (anhydrous) | 50.0 | | |
| Potassium Phosphate (dibasic, trihydrate) | 7.2 | | |
| Potassium Phosphate (monobasic, anhydrous) | 9.3 | | |
| DCA3 medium | g/l | | |
| 0.3M Phosphate buffer containing, pH | 7.5 | | |
| Glycerol | 50 | | |
| Yeast Nitrogen base (Difco) | 6.7 | | |
| Drop-out mix | | | |
| Adenine | 0.5 g | Alanine | 2 g |
| Arginine | 2 g | Asparagine | 2 g |
| Aspartic acid | 2 g | Cysteine | 2 g |
| Glutamine | 2 g | Glutamic acid | 2 g |
| Glycine | 2 g | Histidine | 2 g |
| Inositol | 2 g | Isoleucine | 2 g |
| Leucine | 10 g | Lysine | 2 g |
| Methionine | 2 g | para-Aminobenzoic acid | 0.2 g |
| Phenylalanine | 2 g | Proline | 2 g |
| Serine | 2 g | Threonine | 2 g |
| Tryptophan | 2 g | Tyrosine | 2 g |
| Valine | 2 g | | |

*See Kaiser et al., Methods in Yeast Genetics, Cold Spring Harbor Laboratory Press, USA (1994), incorporated herein by reference.

It will be understood that various modifications may be made to the embodiments and examples described herein. Therefore, the above description should not be construed as limiting, but merely as exemplifications of preferred embodiments. For example, transformation of host cells can be accomplished using biolistic gene transfer techniques.

Although reference has been made herein to production of dicarboxylic acids, it is intended that the present disclosure is applicable to polycarboxylic acids as well. Those with skill in the art will envision other modifications of the various embodiments and examples which are still considered to be within the scope of the claims appended hereto.

What is claimed is:

1. An Isolated nucleic acid encoding the CYTb5 protein (SEQ. ID. NO. 2).

2. The Isolated nucleic acid according to claim 1 wherein the nucleic acid sequence comprises nucleic acid residues numbered 1109 through 1495 of SEQ. ID. NO. 1.

3. Isolated nucleic sequence according to claim 1 wherein the nucleic acid sequence comprises SEQ. ID. NO. 1.

4. An isolated CYTb5 protein comprising the amino acid sequence shown in SEQ. ID. NO. 2.

5. An expression vector comprising a nucleic acid encoding the CYTb5 protein (SEQ. ID. NO. 2).

6. An expression vector according to claim 5 wherein the expression vector is selected from the group consisting of plasmid, phagemid, phage, cosmid, yeast artificial chromosome, linear DNA vector and integration vector.

7. An expression vector according to claim 6 wherein the plasmid is selected from the group consisting of yeast episomal plasmid and yeast replicative plasmid.

8. An expression vector according to claim 5 wherein the nucleic acid encoding the CYTb5 protein comprises nucleic acid residues numbered 1109 through 1495 of SEQ. ID. NO. 1.

9. An expression vector according to claim 5 wherein the nucleic acid encoding the CYTb5 protein comprises SEQ. ID. NO. 1.

10. A host cell transformed with nucleic acid encoding the CYTb5 protein (SEQ. ID. NO. 2).

11. A host cell according to claim 10 wherein the host cell is a yeast cell.

12. A host cell according to claim 11 wherein the yeast cell is selected from the group consisting of Yarrowia, Candida, Bebaromyces, Saccharomyces, Schizosaccharomyces, and Pichia.

13. A host cell according to claim 12 wherein the Candida host cell is selected from the group of *C. tropicalis, C. maltosa, C. apicola, C. paratropicalis, C. albicans, C. cloacae, C. guillermondii, C. intermedia, C. lipolytica, C. parapsilosis,* and *C. zeylenoides.*

14. A host cell according to claim 10 wherein the nucleic acid is contained in an expression vector.

15. A host cell according to claim 14 wherein the expression vector is selected from the group consisting of plasmid, phagemid, phage, cosmid, yeast artificial chromosome, linear DNA vector and integration vector.

16. A host cell according to claim 15 wherein the plasmid is selected from the group consisting of yeast episomal plasmid and yeast replicative plasmid.

17. A host cell according to claim 10 wherein the nucleic acid encoding the CYTb5 protein comprises nucleic acid residues numbered 1109 through 1495 of SEQ. ID. NO. 1.

18. A host cell according to claim 10 wherein the nucleic acid encoding the CYTb5 protein comprises SEQ. ID. NO. 1.

19. A host cell according to claim 10 wherein the host cell contains a disruption of the β-oxidation pathway.

20. A host cell according to claim 10 wherein the host cell contains one or more copies of a gene selected from the group consisting of CPR gene, CYP gene and combinations thereof.

21. A method of producing a CYTb5 protein having the amino acid sequence set forth in SEQ. ID. NO. 2 comprising transforming a host cell with a nucleic acid sequence that encodes the CYTb5 protein and culturing the cell in an appropriate medium.

22. A method of producing a CYTb5 protein according to claim 21 wherein the appropriate medium includes an organic substrate.

* * * * *

SEQUENCE LISTING

<160> NUMBER OF SEQ ID NOS: 45

<210> SEQ ID NO 1
<211> LENGTH: 2710
<212> TYPE: DNA
<213> ORGANISM: Candida tropicalis

<400> SEQUENCE: 1

```
acatacttca agcagtttgg cgacatagtg aacctcaagt tatcacggaa caagacgacg     60
ggcaagagca agcactacgg gtttatagag ttcacgtcgc ctgaagttgc ccagatcgcg    120
gcggagacga tgaacaacta cttgttgttt ggacacttga tcaaatgtga ggttgtcagc    180
gagccgttca aggacttgtt caaggactcg aagaggaagt tcaaggtgat tccctggaag    240
aagatcgcga aggataagca cgataagcca aagtccgcga aggagtgggc gaagttggtg    300
gagaagttcg aagagtccaa gaagaagaag caggaggagt tgaagagtaa aggtattgat    360
tttgatttgg ctgctatata aaggagataa gagaggagga tgacaagcgc aaacgagcat    420
tctgttgatg tgtaaagcag gtatagataa tagcggataa cgtaaaataa gagatctcca    480
acttccaact tccaacttcc gaccctcatc ttttggggga gagggattgg tatgtagtgg    540
tgagggagag gaggatattt tgttttgcct aattgggata aattatccca gtcagttgaa    600
agagcgaggc gtaagccatt tctttttcta actgcaaata gcatacagat gcgatagtta    660
acgaagagag aaatcaagag caggtgacta catacataga tagtgacatt ataataacat    720
ggcgcatcat tggttctatg tagctggcag ggttattatc aagcttgaat agtttaataa    780
aaatcgtacc atgaatgtat gcatagaagc aataaggaag cctgtgcctg tgagtagtag    840
cagtagcggg gggagacgct agtttagggg taaaatgtca gcacatgaac agcagttgaa    900
gtgggtgcca atcaagtaag aacatcttgt gaaaaatcaa aagcaatggt atatgtgttc    960
ctgcatacag tgctggagtc aacgagccaa aaaaaaaaaa gaaagaaaga gagaaaaact   1020
tatcgtataa aaaccacaca aaaatttccc aatcccaatt ccttcattct tcttctttta   1080
ctgatttaac ccacagatac atacaattat gaccgacaca gacaccacga ccaccatcta   1140
cacccacgaa gaggttgccc agcacaccac ccacgacgac ttgtgggtta ttctcaatgg   1200
taaggtctac aacatctcca actatataga cgagcaccca ggtggtgaag aagtcattct   1260
tgattgcgcc ggcacagacg ccactgaagc ctttgacgac attggccact ccgacgaggc   1320
ccacgagatc ttggaaaagt tgtacattgg taacttgaag ggcgctaaga ttgttgaggc   1380
caagcacgcg cagtcgttca gcacggaaga agactcgggt atcaacttcc cattgattgc   1440
tgttggtgtg tttttggctg ctttcggtgt ctactactac aagaccaact ttgcctaagc   1500
ataacaagca gtacagttga aggacagggt agaggagatg agaaaaaacg ggaacccaac   1560
aaagattatt ttcacacatc acatggaggg gctgatccca ctttttgacg tcaatatcca   1620
cagcacgaag aaagaaagaa agaaagaaag tctatggaag aggaaatgga tcacattaga   1680
gcttttcttt atgtaacata tatatatata taaactaata cagatttaca gatacaccac   1740
atcaccgcag ggcttatcat ctgatggtgc ccaaaaaaaa aaatccactg tggatgagcc   1800
tagttaggag atatcggagt agctcattct tttgatatct aggtcttcct ctcttggatt   1860
```

-continued

```
ctacgttggt acttggtgct acacgatgag atcaccaggt gtcattctgg agtttggtgg   1920

aaagtgtgtt gatttttttta gtaagcaaga atttgttgag ttctattgga tgttctggtg   1980

cggccacttc catcccccca ccccttgtct tgtcttgtct tgtcttattt ttttgggtcg   2040

gttggcggaa gtaagacgca cgcacaggag gagcacgacg gataaatatc cactttttttc   2100

acacgcgtcg attgacggct tgtgtgaatt gtggggaata cggataaggg ggtataccac   2160

acacacacat atctaacata tcagaccact ttctataaca gatctcatga tccccttgag   2220

agttgatgca agtctatgct cctgtgatat tgcccccccc cccccaagga agggcggggc   2280

atgttatcag ggacctggat gaacccttga tggcggtgtg agtagatgca agagaggttg   2340

tgctttggaa gtagctgaag gtgtagggac atccggtact atagttctct tgaaggatca   2400

tgccagctcc ctttctgtgg ctctctggaa gctctgcatc ttctcttcgt tgaaacagcg   2460

tggagttacg aaaggtaccc tgtggtgagt tcaaacaaga catggctcta caagctgtcg   2520

aggataaaag taattaaaca acatgtatat atattaataa acggatccgt ggtgctagat   2580

tgtggtagat gtttagtatc gtttatcacc tctagtgaaa actagcattt gattccatta   2640

gtcatcagta cttgatgtta cattcaacca aatgaaggtc ggtccaagat ccaaagaatt   2700

caaaaagctt                                                          2710
```

<210> SEQ ID NO 2
<211> LENGTH: 129
<212> TYPE: PRT
<213> ORGANISM: Candida tropicalis

<400> SEQUENCE: 2

```
Met Thr Asp Thr Asp Thr Thr Thr Thr Ile Tyr Thr His Glu Glu Val
1               5                   10                  15

Ala Gln His Thr Thr His Asp Asp Leu Trp Val Ile Leu Asn Gly Lys
            20                  25                  30

Val Tyr Asn Ile Ser Asn Tyr Ile Asp Glu His Pro Gly Gly Glu Glu
        35                  40                  45

Val Ile Leu Asp Cys Ala Gly Thr Asp Ala Thr Glu Ala Phe Asp Asp
    50                  55                  60

Ile Gly His Ser Asp Glu Ala His Glu Ile Leu Glu Lys Leu Tyr Ile
65                  70                  75                  80

Gly Asn Leu Lys Gly Ala Lys Ile Val Glu Ala Lys His Ala Gln Ser
                85                  90                  95

Phe Ser Thr Glu Glu Asp Ser Gly Ile Asn Phe Pro Leu Ile Ala Val
            100                 105                 110

Gly Val Phe Leu Ala Ala Phe Gly Val Tyr Tyr Tyr Lys Thr Asn Phe
        115                 120                 125

Ala
```

<210> SEQ ID NO 3
<211> LENGTH: 4206
<212> TYPE: DNA
<213> ORGANISM: Candida tropicalis

<400> SEQUENCE: 3

```
catcaagatc atctatgggg ataattacga cagcaacatt gcagaaagag cgttggtcac     60

aatcgaaaga gcctatggcg ttgccgtcgt tgaggcaaat gacagcacca acaataacga    120

tggtcccagt gaagagcctt cagaacagtc cattgttgac gcttaaggca cggataatta    180

cgtggggcaa aggaacgcgg aattagttat ggggggatca aaagcggaag atttgtgttg    240
```

-continued

```
cttgtgggtt ttttccttta tttttcatat gatttctttg cgcaagtaac atgtgccaat    300
ttagtttgtg attagcgtgc cccacaattg gcatcgtgga cgggcgtgtt ttgtcatacc    360
ccaagtctta actagctcca cagtctcgac ggtgtctcga cgatgtcttc ttccacccct    420
cccatgaatc attcaaagtt gttgggggat ctccaccaag ggcaccggag ttaatgctta    480
tgtttctccc actttggttg tgattggggt agtctagtga gttggagatt ttcttttttt    540
cgcaggtgtc tccgatatcg aaatttgatg aatatagaga gaagccagat cagcacagta    600
gattgccttt gtagttagag atgttgaaca gcaactagtt gaattacacg ccaccacttg    660
acagcaagtg cagtgagctg taaacgatgc agccagagtg tcaccaccaa ctgacgttgg    720
gtggagttgt tgttgttgtt gttggcaggg ccatattgct aaacgaagac aagtagcaca    780
aaacccaagc ttaagaacaa aaataaaaaa aattcatacg acaattccaa agccattgat    840
ttacataatc aacagtaaga cagaaaaaac tttcaacatt tcaaagttcc ctttttccta    900
ttacttcttt tttttcttct ttccttcttt ccttctgttt ttcttacttt atcagtcttt    960
tacttgtttt tgcaattcct catcctcctc ctactcctcc tcaccatggc tttagacaag   1020
ttagatttgt atgtcatcat aacattggtg gtcgctgtag ccgcctattt tgctaagaac   1080
cagttccttg atcagcccca ggacaccggg ttcctcaaca cggacagcgg aagcaactcc   1140
agagacgtct tgctgacatt gaagaagaat aataaaaaca cgttgttgtt gtttgggtcc   1200
cagacgggta cggcagaaga ttacgccaac aaattgtcca gagaattgca ctccagattt   1260
ggcttgaaaa cgatggttgc agatttcgct gattacgatt gggataactt cggagatatc   1320
accgaagaca tcttggtgtt tttcattgtt gccacctatg gtgagggtga acctaccgat   1380
aatgccgacg agttccacac ctggttgact gaagaagctg acactttgag taccttgaaa   1440
tacaccgtgt tcgggttggg taactccacg tacgagttct tcaatgccat tggtagaaag   1500
tttgacagat tgttgagcga gaaaggtggt gacaggtttg ctgaatacgc tgaaggtgat   1560
gacggtactg gcaccttgga cgaagatttc atggcctgga aggacaatgt ctttgacgcc   1620
ttgaagaatg atttgaactt tgaagaaaag gaattgaagt acgaaccaaa cgtgaaattg   1680
actgagagag acgacttgtc tgctgctgac tcccaagttt ccttgggtga gccaaacaag   1740
aagtacatca actccgaggg catcgacttg accaagggtc cattcgacca cacccaccca   1800
tacttggcca gaatcaccga gacgagagag ttgttcagct ccaaggacag acactgtatc   1860
cacgttgaat ttgacatttc tgaatcgaac ttgaaataca ccaccggtga ccatctagct   1920
atctggccat ccaactccga cgaaaacatt aagcaatttg ccaagtgttt cggattggaa   1980
gataaactcg acactgttat tgaattgaag gcgttggact ccacttacac catcccattc   2040
ccaaccccaa ttacctacgg tgctgtcatt agacaccatt tagaaatctc cggtccagtc   2100
tcgagacaat tctttttgtc aattgctggg tttgctcctg atgaagaaac aaagaaggct   2160
tttaccagac ttggtggtga caagcaagaa ttcgccgcca aggtcacccg cagaaagttc   2220
aacattgccg atgccttgtt atattcctcc aacaacgctc catggtccga tgttcctttt   2280
gaattcctta ttgaaaacgt tccacacttg actccacgtt actactccat ttcgtcttcg   2340
tcattgagtg aaaagcaact catcaacgtt actgcagttg ttgaagccga agaagaagct   2400
gatggcagac cagtcactgg tgttgtcacc aacttgttga agaacgttga aattgtgcaa   2460
aacaagactg gcgaaaagcc acttgtccac tacgatttga gcggcccaag aggcaagttc   2520
aacaagttca agttgccagt gcatgtgaga agatccaact ttaagttgcc aaagaactcc   2580
```

-continued

```
accaccccag ttatcttgat tggtccaggt actggtgttg ccccattgag aggttttgtc   2640

agagaaagag ttcaacaagt caagaatggt gtcaatgttg gcaagacttt gttgttttat   2700

ggttgcagaa actccaacga ggactttttg tacaagcaag aatgggccga gtacgcttct   2760

gttttgggtg aaaactttga gatgttcaat gccttctcca gacaagaccc atccaagaag   2820

gtttacgtcc aggataagat tttagaaaac agccaacttg tgcacgagtt gttgactgaa   2880

ggtgccatta tctacgtctg tggtgatgcc agtagaatgg ctagagacgt gcagaccaca   2940

atttccaaga ttgttgctaa aagcagagaa attagtgaag acaaggctgc tgaattggtc   3000

aagtcctgga aggtccaaaa tagataccaa gaagatgttt ggtagactca aacgaatctc   3060

tctttctccc aacgcattta tgaatcttta ttctcattga agctttacat atgttctaca   3120

ctttattttt tttttttttt ttattattat attacgaaac ataggtcaac tatatatact   3180

tgattaaatg ttatagaaac aataactatt atctactcgt ctacttcttt ggcattgaca   3240

tcaacattac cgttcccatt accgttgccg ttggcaatgc cgggatattt agtacagtat   3300

ctccaatccg gatttgagct attgtagatc agctgcaagt cattctccac cttcaaccag   3360

tacttatact tcatctttga cttcaagtcc aagtcataaa tattacaagt tagcaagaac   3420

ttctggccat ccacgatata gacgttattc acgttattat gcgacgtatg gatgtggtta   3480

tccttattga acttctcaaa cttcaaaaac aaccccacgt cccgcaacgt cattatcaac   3540

gacaagttct ggctcacgtc gtcggagctc gtcaagttct caattagatc gttcttgtta   3600

ttgatcttct ggtactttct caattgctgg aacacattgt cctcgttgtt caaatagatc   3660

ttgaacaact ttttcaacgg gatcaacttc tcaatctggg ccaagatctc cgccgggatc   3720

ttcagaaaca agtcctgcaa cccctggtcg atggtctccg ggtacaacaa gtccaagggg   3780

cagaagtgtc taggcacgtg tttcaactgg ttcaacgaac atgttcgaca gtagttcgag   3840

ttatagttat cgtacaacca ttttggtttg atttcgaaaa tgacggagct gatgccatca   3900

ttctcctggt tcctctcata gtacaactgg cacttcttcg agaggctcaa ttcctcgtag   3960

ttcccgtcca agatattcgg caacaagagc ccgtaccgct cacggagcat caagtcgtgg   4020

ccctggttgt tcaacttgtt gatgaagtcc gaggtcaaga caatcaactg gatgtcgatg   4080

atctggtgcg ggaacaagtt cttgcatttt agctcgatga agtcgtacaa ctcacacgtc   4140

gagatatact cctgttcctc cttcaagagc cggatccgca agagcttgtg cttcaagtag   4200

tcgttg                                                              4206
```

```
<210> SEQ ID NO 4
<211> LENGTH: 679
<212> TYPE: PRT
<213> ORGANISM: Candida tropicalis

<400> SEQUENCE: 4

Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Leu Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80
```

-continued

```
Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Lys Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220

Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Asp Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Ala Phe Thr Arg Leu Gly Gly Asp Lys Gln Glu Phe Ala Ala Lys Val
385                 390                 395                 400

Thr Arg Arg Lys Phe Asn Ile Ala Asp Ala Leu Leu Tyr Ser Ser Asn
                405                 410                 415

Asn Ala Pro Trp Ser Asp Val Pro Phe Glu Phe Leu Ile Glu Asn Val
            420                 425                 430

Pro His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Val Glu Ile Val Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
```

-continued

```
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675


<210> SEQ ID NO 5
<211> LENGTH: 4145
<212> TYPE: DNA
<213> ORGANISM: Candida tropicalis

<400> SEQUENCE: 5

tatatgatat atgatatatc ttcctgtgta attattattc gtattcgtta atacttacta     60

catttttttt tctttattta tgaagaaaag gagagttcgt aagttgagtt gagtagaata    120

ggctgttgtg catacgggga gcagaggaga gtatccgacg aggaggaact gggtgaaatt    180

tcatctatgc tgttgcgtcc tgtactgtac tgtaaatctt agatttccta gaggttgttc    240

tagcaaataa agtgtttcaa gatacaattt tacaggcaag ggtaaaggat caactgatta    300

gcggaagatt ggtgttgcct gtggggttct tttatttttc atatgatttc tttgcgcgag    360

taacatgtgc caatctagtt tatgattagc gtacctccac aattggcatc ttggacgggc    420

gtgttttgtc ttaccccaag ccttatttag ttccacagtc tcgacggtgt ctcgccgatg    480

tcttctccca cccctcgcag gaatcattcg aagttgttgg gggatctcct ccgcagttta    540

tgttcatgtc tttcccactt tggttgtgat tggggtagcg tagtgagttg gtgattttct    600

tttttcgcag gtgtctccga tatcgaagtt tgatgaatat aggagccaga tcagcatggt    660

atattgcctt tgtagataga gatgttgaac aacaactagc tgaattacac accaccgcta    720

aacgatgcgc acagggtgtc accgccaact gacgttgggt ggagttgttg ttggcagggc    780

catattgcta aacgaagaga agtagcacaa aacccaaggt taagaacaat taaaaaaatt    840

catacgacaa ttccacagcc atttacataa tcaacagcga caaatgagac agaaaaaact    900

ttcaacattt caaagttccc tttttcctat tacttctttt tttctttcct tcctttcatt    960

tcctttcctt ctgcttttat tactttacca gtcttttgct tgtttttgca attcctcatc   1020

ctcctcctca ccatggcttt agacaagtta gatttgtatg tcatcataac attggtggtc   1080
```

-continued

```
gctgtggccg cctattttgc taagaaccag ttccttgatc agccccagga caccgggttc   1140
ctcaacacgg acagcggaag caactccaga gacgtcttgc tgacattgaa gaagaataat   1200
aaaaacacgt tgttgttgtt tgggtcccag accggtacgg cagaagatta cgccaacaaa   1260
ttgtcaagag aattgcactc cagatttggc ttgaaaacca tggttgcaga tttcgctgat   1320
tacgattggg ataacttcgg agatatcacc gaagatatct tggtgttttt catcgttgcc   1380
acctacggtg agggtgaacc taccgacaat gccgacgagt tccacacctg gttgactgaa   1440
gaagctgaca ctttgagtac tttgagatat accgtgttcg ggttgggtaa ctccacctac   1500
gagttcttca atgctattgg tagaaagttt gacagattgt tgagtgagaa aggtggtgac   1560
agatttgctg aatatgctga aggtgacgac ggcactggca ccttggacga agatttcatg   1620
gcctggaagg ataatgtctt tgacgccttg aagaatgact tgaactttga agaaaaggaa   1680
ttgaagtacg aaccaaacgt gaaattgact gagagagatg acttgtctgc tgccgactcc   1740
caagtttcct tgggtgagcc aaacaagaag tacatcaact ccgagggcat cgacttgacc   1800
aagggtccat tcgaccacac ccacccatac ttggccagga tcaccgagac cagagagttg   1860
ttcagctcca aggaaagaca ctgtattcac gttgaatttg acatttctga atcgaacttg   1920
aaatacacca ccggtgacca tctagccatc tggccatcca actccgacga aaacatcaag   1980
caatttgcca agtgtttcgg attggaagat aaactcgaca ctgttattga attgaaggca   2040
ttggactcca cttacaccat tccattccca actccaatta cttacggtgc tgtcattaga   2100
caccatttag aaatctccgg tccagtctcg agacaattct tttgtcgat tgctgggttt    2160
gctcctgatg aagaaacaaa gaagactttc accagacttg gtggtgacaa acaagaattc   2220
gccaccaagg ttacccgcag aaagttcaac attgccgatg ccttgttata ttcctccaac   2280
aacactccat ggtccgatgt tcctttttgag ttccttattg aaaacatcca acacttgact  2340
ccacgttact actccatttc ttcttcgtcg ttgagtgaaa aacaactcat caatgttact   2400
gcagtcgttg aggccgaaga agaagccgat ggcagaccag tcactggtgt tgttaccaac   2460
ttgttgaaga acattgaaat tgcgcaaaac aagactggcg aaaagccact tgttcactac   2520
gatttgagcg gcccaagagg caagttcaac aagttcaagt tgccagtgca cgtgagaaga   2580
tccaacttta agttgccaaa gaactccacc accccagtta tcttgattgg tccaggtact   2640
ggtgttgccc cattgagagg tttcgttaga gaaagagttc aacaagtcaa gaatggtgtc   2700
aatgttggca agactttgtt gttttatggt tgcagaaact ccaacgagga ctttttgtac   2760
aagcaagaat gggccgagta cgcttctgtt ttgggtgaaa actttgagat gttcaatgcc   2820
ttctctagac aagacccatc caagaaggtt tacgtccagg ataagatttt agaaaacagc   2880
caacttgtgc acgaattgtt gaccgaaggt gccattatct acgtctgtgg tgacgccagt   2940
agaatggcca gagacgtcca gaccacgatc tccaagattg ttgccaaaag cagagaaatc   3000
agtgaagaca aggccgctga attggtcaag tcctggaaag tccaaaatag ataccaagaa   3060
gatgtttggt agactcaaac gaatctctct ttctcccaac gcatttatga atattctcat   3120
tgaagtttta catatgttct atatttcatt ttttttttat tatattacga aacataggtc   3180
aactatatat acttgattaa atgttataga aacaataatt attatctact cgtctacttc   3240
tttggcattg gcattggcat tggcattggc attgccgttg ccgttggtaa tgccgggata   3300
tttagtacag tatctccaat ccggatttga gctattgtaa atcagctgca agtcattctc   3360
caccttcaac cagtacttat acttcatctt tgacttcaag tccaagtcat aaatattaca   3420
agttagcaag aacttctggc catccacaat atagacgtta ttcacgttat tatgcgacgt   3480
```

-continued

```
atggatatgg ttatccttat tgaacttctc aaacttcaaa aacaacccca cgtcccgcaa   3540

cgtcattatc aacgacaagt tctgactcac gtcgtcggag ctcgtcaagt tctcaattag   3600

atcgttcttg ttattgatct tctggtactt tctcaactgc tggaacacat tgtcctcgtt   3660

gttcaaatag atcttgaaca acttcttcaa gggaatcaac ttttcgatct gggccaagat   3720

ttccgccggg atcttcagaa acaagtcctg caacccctgg tcgatggtct cggggtacaa   3780

caagtctaag gggcagaagt gtctaggcac gtgtttcaac tggttcaagg aacatgttcg   3840

acagtagttc gagttatagt tatcgtacaa ccactttggc ttgatttcga aaatgacgga   3900

gctgatccca tcattctcct ggttcctttc atagtacaac tggcatttct tcgagagact   3960

caactcctcg tagttcccgt ccaagatatt cggcaacaag agcccgtagc gctcacggag   4020

catcaagtcg tggccctggt tgttcaactt gttgatgaag tccgatgtca agacaatcaa   4080

ctggatgtcg atgatctggt gcggaaacaa gttcttgcac tttagctcga tgaagtcgta   4140

caact                                                               4145
```

<210> SEQ ID NO 6
<211> LENGTH: 679
<212> TYPE: PRT
<213> ORGANISM: Candida tropicalis
<220> FEATURE:
<221> NAME/KEY: MISC_FEATURE
<222> LOCATION: (50)..(50)
<223> OTHER INFORMATION: Xaa = leucine or serine

<400> SEQUENCE: 6

```
Met Ala Leu Asp Lys Leu Asp Leu Tyr Val Ile Ile Thr Leu Val Val
1               5                   10                  15

Ala Val Ala Ala Tyr Phe Ala Lys Asn Gln Phe Leu Asp Gln Pro Gln
            20                  25                  30

Asp Thr Gly Phe Leu Asn Thr Asp Ser Gly Ser Asn Ser Arg Asp Val
        35                  40                  45

Leu Xaa Thr Leu Lys Lys Asn Asn Lys Asn Thr Leu Leu Leu Phe Gly
    50                  55                  60

Ser Gln Thr Gly Thr Ala Glu Asp Tyr Ala Asn Lys Leu Ser Arg Glu
65                  70                  75                  80

Leu His Ser Arg Phe Gly Leu Lys Thr Met Val Ala Asp Phe Ala Asp
                85                  90                  95

Tyr Asp Trp Asp Asn Phe Gly Asp Ile Thr Glu Asp Ile Leu Val Phe
            100                 105                 110

Phe Ile Val Ala Thr Tyr Gly Glu Gly Glu Pro Thr Asp Asn Ala Asp
        115                 120                 125

Glu Phe His Thr Trp Leu Thr Glu Glu Ala Asp Thr Leu Ser Thr Leu
    130                 135                 140

Arg Tyr Thr Val Phe Gly Leu Gly Asn Ser Thr Tyr Glu Phe Phe Asn
145                 150                 155                 160

Ala Ile Gly Arg Lys Phe Asp Arg Leu Leu Ser Glu Lys Gly Gly Asp
                165                 170                 175

Arg Phe Ala Glu Tyr Ala Glu Gly Asp Asp Gly Thr Gly Thr Leu Asp
            180                 185                 190

Glu Asp Phe Met Ala Trp Lys Asp Asn Val Phe Asp Ala Leu Lys Asn
        195                 200                 205

Asp Leu Asn Phe Glu Glu Lys Glu Leu Lys Tyr Glu Pro Asn Val Lys
    210                 215                 220
```

-continued

```
Leu Thr Glu Arg Asp Asp Leu Ser Ala Ala Asp Ser Gln Val Ser Leu
225                 230                 235                 240

Gly Glu Pro Asn Lys Lys Tyr Ile Asn Ser Glu Gly Ile Asp Leu Thr
                245                 250                 255

Lys Gly Pro Phe Asp His Thr His Pro Tyr Leu Ala Arg Ile Thr Glu
            260                 265                 270

Thr Arg Glu Leu Phe Ser Ser Lys Glu Arg His Cys Ile His Val Glu
        275                 280                 285

Phe Asp Ile Ser Glu Ser Asn Leu Lys Tyr Thr Thr Gly Asp His Leu
    290                 295                 300

Ala Ile Trp Pro Ser Asn Ser Asp Glu Asn Ile Lys Gln Phe Ala Lys
305                 310                 315                 320

Cys Phe Gly Leu Glu Asp Lys Leu Asp Thr Val Ile Glu Leu Lys Ala
                325                 330                 335

Leu Asp Ser Thr Tyr Thr Ile Pro Phe Pro Thr Pro Ile Thr Tyr Gly
            340                 345                 350

Ala Val Ile Arg His His Leu Glu Ile Ser Gly Pro Val Ser Arg Gln
        355                 360                 365

Phe Phe Leu Ser Ile Ala Gly Phe Ala Pro Asp Glu Glu Thr Lys Lys
    370                 375                 380

Thr Phe Thr Arg Leu Gly Gly Asp Lys Gln Glu Phe Ala Thr Lys Val
385                 390                 395                 400

Thr Arg Arg Lys Phe Asn Ile Ala Asp Ala Leu Leu Tyr Ser Ser Asn
                405                 410                 415

Asn Thr Pro Trp Ser Asp Val Pro Phe Glu Phe Leu Ile Glu Asn Ile
            420                 425                 430

Gln His Leu Thr Pro Arg Tyr Tyr Ser Ile Ser Ser Ser Ser Leu Ser
        435                 440                 445

Glu Lys Gln Leu Ile Asn Val Thr Ala Val Val Glu Ala Glu Glu Glu
    450                 455                 460

Ala Asp Gly Arg Pro Val Thr Gly Val Val Thr Asn Leu Leu Lys Asn
465                 470                 475                 480

Ile Glu Ile Ala Gln Asn Lys Thr Gly Glu Lys Pro Leu Val His Tyr
                485                 490                 495

Asp Leu Ser Gly Pro Arg Gly Lys Phe Asn Lys Phe Lys Leu Pro Val
            500                 505                 510

His Val Arg Arg Ser Asn Phe Lys Leu Pro Lys Asn Ser Thr Thr Pro
        515                 520                 525

Val Ile Leu Ile Gly Pro Gly Thr Gly Val Ala Pro Leu Arg Gly Phe
    530                 535                 540

Val Arg Glu Arg Val Gln Gln Val Lys Asn Gly Val Asn Val Gly Lys
545                 550                 555                 560

Thr Leu Leu Phe Tyr Gly Cys Arg Asn Ser Asn Glu Asp Phe Leu Tyr
                565                 570                 575

Lys Gln Glu Trp Ala Glu Tyr Ala Ser Val Leu Gly Glu Asn Phe Glu
            580                 585                 590

Met Phe Asn Ala Phe Ser Arg Gln Asp Pro Ser Lys Lys Val Tyr Val
        595                 600                 605

Gln Asp Lys Ile Leu Glu Asn Ser Gln Leu Val His Glu Leu Leu Thr
    610                 615                 620

Glu Gly Ala Ile Ile Tyr Val Cys Gly Asp Ala Ser Arg Met Ala Arg
625                 630                 635                 640

Asp Val Gln Thr Thr Ile Ser Lys Ile Val Ala Lys Ser Arg Glu Ile
```

-continued

```
                645                 650                 655

Ser Glu Asp Lys Ala Ala Glu Leu Val Lys Ser Trp Lys Val Gln Asn
            660                 665                 670

Arg Tyr Gln Glu Asp Val Trp
        675


<210> SEQ ID NO 7
<211> LENGTH: 4115
<212> TYPE: DNA
<213> ORGANISM: Candida tropicalis

<400> SEQUENCE: 7

catatgcgct aatcttcttt ttctttttat cacaggagaa actatcccac ccccacttcg     60

aaacacaatg acaactcctg cgtaacttgc aaattcttgt ctgactaatt gaaaactccg    120

gacgagtcag acctccagtc aaacggacag acagacaaac acttggtgcg atgttcatac    180

ctacagacat gtcaacgggt gttagacgac ggtttcttgc aaagacaggt gttggcatct    240

cgtacgatgg caactgcagg aggtgtcgac ttctccttta ggcaatagaa aaagactaag    300

agaacagcgt ttttacaggt tgcattggtt aatgtagtat ttttttagtc ccagcattct    360

gtgggttgct ctgggtttct agaataggaa atcacaggag aatgcaaatt cagatggaag    420

aacaaagaga taaaaaacaa aaaaaaactg agttttgcac caatagaatg tttgatgata    480

tcatccactc gctaaacgaa tcatgtgggt gatcttctct ttagttttgg tctatcataa    540

aacacatgaa agtgaaatcc aaatacacta cactccgggt attgtccttc gttttacaga    600

tgtctcattg tcttactttt gaggtcatag gagttgcctg tgagagatca cagagattat    660

cacactcaca tttatcgtag tttcctatct catgctgtgt gtctctggtt ggttcatgag    720

tttggattgt tgtacattaa aggaatcgct ggaaagcaaa gctaactaaa ttttctttgt    780

cacaggtaca ctaacctgta aaacttcact gccacgccag tctttcctga ttgggcaagt    840

gcacaaacta caacctgcaa aacagcactc cgcttgtcac aggttgtctc ctctcaacca    900

acaaaaaaat aagattaaac tttctttgct catgcatcaa tcggagttat ctctgaaaga    960

gttgcctttg tgtaatgtgt gccaaactca aactgcaaaa ctaaccacag aatgatttcc   1020

ctcacaatta tataaactca cccacatttc cacagaccgt aatttcatgt ctcactttct   1080

cttttgctct tcttttactt agtcaggttt gataacttcc ttttttatta ccctatctta   1140

tttatttatt tattcattta taccaaccaa ccaaccatgg ccacacaaga aatcatcgat   1200

tctgtacttc cgtacttgac caaatggtac actgtgatta ctgcagcagt attagtcttc   1260

cttatctcca caaacatcaa gaactacgtc aaggcaaaga aattgaaatg tgtcgatcca   1320

ccatacttga aggatgccgg tctcactggt attctgtctt tgatcgccgc catcaaggcc   1380

aagaacgacg gtagattggc taactttgcc gatgaagttt tcgacgagta cccaaaccac   1440

accttctact tgtctgttgc cggtgctttg aagattgtca tgactgttga cccagaaaac   1500

atcaaggctg tcttggccac ccaattcact gacttctcct tgggtaccag acacgcccac   1560

tttgctcctt tgttgggtga cggtatcttc accttggacg gagaaggttg gaagcactcc   1620

agagctatgt tgagaccaca gtttgctaga gaccagattg gacacgttaa agccttggaa   1680

ccacacatcc aaatcatggc taagcagatc aagttgaacc agggaaagac tttcgatatc   1740

caagaattgt tctttagatt taccgtcgac accgctactg agttcttgtt tggtgaatcc   1800

gttcactcct tgtacgatga aaaattgggc atcccaactc caaacgaaat cccaggaaga   1860

gaaaactttg ccgctgcttt caacgtttcc caacactact tggccaccag aagttactcc   1920
```

-continued

```
cagacttttt actttttgac caaccctaag gaattcagag actgtaacgc caaggtccac   1980
cacttggcca agtactttgt caacaaggcc ttgaacttta ctcctgaaga actcgaagag   2040
aaatccaagt ccggttacgt tttcttgtac gaattggtta agcaaaccag agatccaaag   2100
gtcttgcaag atcaattgtt gaacattatg gttgccggaa gagacaccac tgccggtttg   2160
ttgtcctttg ctttgtttga attggctaga cacccagaga tgtggtccaa gttgagagaa   2220
gaaatcgaag ttaactttgg tgttggtgaa gactcccgcg ttgaagaaat taccttcgaa   2280
gccttgaaga gatgtgaata cttgaaggct atccttaacg aaaccttgcg tatgtaccca   2340
tctgttcctg tcaactttag aaccgccacc agagacacca ctttgccaag aggtggtggt   2400
gctaacggta ccgacccaat ctacattcct aaaggctcca ctgttgctta cgttgtctac   2460
aagacccacc gtttggaaga atactacggt aaggacgcta acgacttcag accagaaaga   2520
tggtttgaac catctactaa gaagttgggc tgggcttatg ttccattcaa cggtggtcca   2580
agagtctgct tgggtcaaca attcgccttg actgaagctt cttatgtgat cactagattg   2640
gcccagatgt ttgaaactgt ctcatctgat ccaggtctcg aataccctcc accaaagtgt   2700
attcacttga ccatgagtca caacgatggt gtctttgtca agatgtaaag tagtcgatgc   2760
tgggtattcg attacatgtg tataggaaga ttttggtttt ttattcgttc tttttttaa   2820
tttttgttaa attagtttag agatttcatt aatacataga tgggtgctat ttccgaaact   2880
ttacttctat cccctgtatc ccttattatc cctctcagtc acatgattgc tgtaattgtc   2940
gtgcaggaca caaactccct aacggactta aaccataaac aagctcagaa ccataagccg   3000
acatcactcc ttcttctctc ttctccaacc aatagcatgg acagacccac cctcctatcc   3060
gaatcgaaga cccttattga ctccataccc acctggaagc cctcaagcc acacacgtca   3120
tccagcccac ccatcaccac atccctctac tcgacaacgt ccaaagacgg cgagttctgg   3180
tgtgcccgga aatcagccat cccggccaca tacaagcagc cgttgattgc gtgcatactc   3240
ggcgagccca caatgggagc cacgcattcg gaccatgaag caaagtacat tcacgagatc   3300
acgggtgttt cagtgtcgca gattgagaag ttcgacgatg gatggaagta cgatctcgtt   3360
gcggattacg acttcggtgg gttgttatct aaacgaagat tctatgagac gcagcatgtg   3420
tttcggttcg aggattgtgc gtacgtcatg agtgtgcctt ttgatggacc caaggaggaa   3480
ggttacgtgg ttgggacgta cagatccatt gaaaggttga gctggggtaa agacggggac   3540
gtggagtgga ccatggcgac gacgtcggat cctggtgggt ttatcccgca atggataact   3600
cgattgagca tccctggagc aatcgcaaaa gatgtgccta gtgtattaaa ctacatacag   3660
aaataaaaac gtgtcttgat tcattggttt ggttcttgtt gggttccgag ccaatatttc   3720
acatcatctc ctaaattctc caagaatccc aacgtagcgt agtccagcac gccctctgag   3780
atcttattta atatcgactt ctcaaccacc ggtggaatcc cgttcagacc attgttacct   3840
gtagtgtgtt tgctcttgtt cttgatgaca atgatgtatt tgtcacgata cctgaaataa   3900
taaaacatcc agtcattgag cttattactc gtgaacttat gaaagaactc attcaagccg   3960
ttcccaaaaa acccagaatt gaagatcttg ctcaactggt catgcaagta gtagatcgcc   4020
atgatctgat actttaccaa gctatcctct ccaagttctc ccacgtacgg caagtacggc   4080
aacgagctct ggaagctttg ttgtttgggg tcata                              4115
```

<210> SEQ ID NO 8
<211> LENGTH: 3948
<212> TYPE: DNA

-continued

<213> ORGANISM: Candida tropicalis

<400> SEQUENCE: 8

```
gacctgtgac gcttccggtg tcttgccacc agtctccaag ttgaccgacg cccaagtcat     60
gtaccacttt atttccggtt acacttccaa gatggctggt actgaagaag gtgtcacgga    120
accacaagct actttctccg cttgtttcgg tcaaccattc ttggtgttgc acccaatgaa    180
gtacgctcaa caattgtctg acaagatctc gcaacacaag gctaacgcct ggttgttgaa    240
caccggttgg gttggttctt ctgctgctag aggtggtaag agatgctcat tgaagtacac    300
cagagccatt ttggacgcta tccactctgg tgaattgtcc aaggttgaat acgaaacttt    360
cccagtcttc aacttgaatg tcccaacctc ctgtccaggt gtcccaagtg aaatcttgaa    420
cccaaccaag gcctggaccg gaaggtgttg actccttcaa caaggaaatc aagtctttgg    480
ctggtaagtt tgctgaaaac ttcaagacct atgctgacca agctaccgct gaagtgagag    540
ctgcaggtcc agaagcttaa agatatttat tcattattta gtttgcctat ttatttctca    600
ttacccatca tcattcaaca ctatatataa agttacttcg gatatcattg taatcgtgcg    660
tgtcgcaatt ggatgatttg gaactgcgct tgaaacggat tcatgcacga agcggagata    720
aaagattacg taatttatct cctgagacaa ttttagccgt gttcacacgc ccttctttgt    780
tctgagcgaa ggataaataa ttagacttcc acagctcatt ctaatttccg tcacgcgaat    840
attgaagggg ggtacatgtg gccgctgaat gtgggggcag taaacgcagt ctctcctctc    900
ccaggaatag tgcaacggag gaaggataac ggatagaaag cggaatgcga ggaaaatttt    960
gaacgcgcaa gaaaagcaat atccgggcta ccaggttttg agccagggaa cacactccta   1020
tttctgctca atgactgaac atagaaaaaa caccaagacg caatgaaacg cacatggaca   1080
tttagacctc cccacatgtg atagtttgtc ttaacagaaa agtataataa gaacccatgc   1140
cgtccctttt ctttcgccgc ttcaactttt tttttttat cttacacaca tcacgaccat   1200
gactgtacac gatattatcg ccacatactt caccaaatgg tacgtgatag taccactcgc   1260
tttgattgct tatagagtcc tcgactactt ctatggcaga tacttgatgt acaagcttgg   1320
tgctaaacca tttttccaga aacagacaga cggctgtttc ggattcaaag ctccgcttga   1380
attgttgaag aagaagagcg acggtaccct catagacttc acactccagc gtatccacga   1440
tctcgatcgt cccgatatcc caactttcac attcccggtc ttttccatca accttgtcaa   1500
tacccttgag ccggagaaca tcaaggccat cttggccact cagttcaacg atttctcctt   1560
gggtaccaga cactcgcact ttgctccttt gttgggtgat ggtatcttta cgttggatgg   1620
cgccggctgg aagcacagca gatctatgtt gagaccacag tttgccagag aacagatttc   1680
ccacgtcaag ttgttggagc cacacgttca ggtgttcttc aaacacgtca gaaaggcaca   1740
gggcaagact tttgacatcc aggaattgtt tttcagattg accgtcgact ccgccaccga   1800
gtttttgttt ggtgaatccg ttgagtcctt gagagatgaa tctatcggca tgtccatcaa   1860
tgcgcttgac tttgacggca aggctggctt tgctgatgct tttaactatt cgcagaatta   1920
tttggcttcg agagcggtta tgcaacaatt gtactgggtg ttgaacggga aaaagtttaa   1980
ggagtgcaac gctaaagtgc acaagtttgc tgactactac gtcaacaagg ctttggactt   2040
gacgcctgaa caattggaaa agcaggatgg ttatgtgttt ttgtacgaat tggtcaagca   2100
aaccagagac aagcaagtgt tgagagacca attgttgaac atcatggttg ctggtagaga   2160
caccaccgcc ggtttgttgt cgtttgtttt ctttgaattg gccagaaacc cagaagttac   2220
caacaagttg agagaagaaa ttgaggacaa gtttggactc ggtgagaatg ctagtgttga   2280
```

-continued agacatttcc tttgagtcgt tgaagtcctg tgaatacttg aaggctgttc tcaacgaaac 2340
cttgagattg tacccatccg tgccacagaa tttcagagtt gccaccaaga acactaccct 2400
cccaagaggt ggtggtaagg acgggttgtc tcctgttttg gtgagaaagg gtcagaccgt 2460
tatttacggt gtctacgcag cccacagaaa cccagctgtt tacggtaagg acgctcttga 2520
gtttagacca gagagatggt ttgagccaga gacaaagaag cttggctggg ccttcctccc 2580
attcaacggt ggtccaagaa tctgtttggg acagcagttt gccttgacag aagcttcgta 2640
tgtcactgtc aggttgctcc aggagtttgc acacttgtct atggacccag acaccgaata 2700
tccacctaag aaaatgtcgc atttgaccat gtcgcttttc gacggtgcca atattgagat 2760
gtattagagg gtcatgtgtt attttgattg tttagtttgt aattactgat taggttaatt 2820
catggattgt tatttattga taggggtttg cgcgtgttgc attcacttgg gatcgttcca 2880
ggttgatgtt tccttccatc ctgtcgagtc aaaaggagtt ttgttttgta actccggacg 2940
atgttttaaa tagaaggtcg atctccatgt gattgttttg actgttactg tgattatgta 3000
atctgcggac gttatacaag catgtgattg tggttttgca gccttttgca cgacaaatga 3060
tcgtcagacg attacgtaat ctttgttaga ggggtaaaaa aaaacaaaat ggcagccaga 3120
atttcaaaca ttctgcaaac aatgcaaaaa atgggaaact ccaacagaca aaaaaaaaaa 3180
ctccgcagca ctccgaaccc acagaacaat ggggcgccag aattattgac tattgtgact 3240
tttttacgct aacgctcatt gcagtgtagt gcgtcttaca cggggtattg ctttctacaa 3300
tgcaagggca cagttgaagg tttgcaccta acgttgcccc gtgtcaactc aatttgacga 3360
gtaacttcct aagctcgaat tatgcagctc gtgcgtcaac ctatgtgcag gaaagaaaaa 3420
atccaaaaaa atcgaaaatg cgactttcga ttttgaataa accaaaaaga aaaatgtcgc 3480 actttttttct cgctctcgct ctctcgaccc aaatcacaac aaatcctcgc gcgcagtatt 3540
tcgacgaaac cacaacaaat aaaaaaaaca aattctacac cacttctttt tcttcaccag 3600
tcaacaaaaa acaacaaatt atacaccatt tcaacgattt ttgctcttat aaatgctata 3660
taatggttta attcaactca ggtatgttta ttttactgtt ttcagctcaa gtatgttcaa 3720
atactaacta cttttgatgt ttgtcgcttt tctagaatca aaacaacgcc cacaacacgc 3780
cgagcttgtc gaatagacgg tttgtttact cattagatgg tcccagatta cttttcaagc 3840
caaagtctct cgagttttgt ttgctgtttc cccaattcct aactatgaag ggtttttata 3900
aggtccaaag accccaaggc atagtttttt tggttccttc ttgtcgtg 3948

<210> SEQ ID NO 9
<211> LENGTH: 3755
<212> TYPE: DNA
<213> ORGANISM: Candida tropicalis

<400> SEQUENCE: 9
gctcaacaat tgtctgacaa gatctcgcaa cacaaggcta acgcctggtt gttgaacact 60
ggttgggttg gttcttctgc tgctagaggt ggtaagagat gttcattgaa gtacaccaga 120
gccattttgg acgctatcca ctctggtgaa ttgtccaagg ttgaatacga gactttccca 180
gtcttcaact tgaatgtccc aacctcctgc ccaggtgtcc caagtgaaat cttgaaccca 240
accaaggcct ggaccgaagg tgttgactcc ttcaacaagg aaatcaagtc tttggctggt 300
aagtttgctg aaaacttcaa gacctatgct gaccaagcta ccgctgaagt tagagctgca 360
ggtccagaag cttaaagata tttattcact atttagtttg cctatttatt tctcatcacc 420

-continued

```
catcatcatt caacaatata tataaagtta tttcggaact catatatcat tgtaatcgtg    480
cgtgttgcaa ttgggtaatt tgaaactgta gttggaacgg attcatgcac gatgcggaga    540
taacacgaga ttatctccta agacaatttt ggcctcattc acacgccctt cttctgagct    600
aaggataaat aattagactt cacaagttca ttaaaatatc cgtcacgcga aaactgcaac    660
aataaggaag gggggggtag acgtagccga tgaatgtggg gtgccagtaa acgcagtctc    720
tctctccccc cccccccccc cccccctcagg aatagtacaa cgggggaagg ataacggata    780
gcaagtggaa tgcgaggaaa atttgaatg cgcaaggaaa gcaatatccg ggctatcagg    840
ttttgagcca ggggacacac tcctcttctg cacaaaaact taacgtagac aaaaaaaaaa    900
aactccacca agacacaatg aatcgcacat ggacatttag acctccccac atgtgaaagc    960
ttctctggcg aaagcaaaaa aagtataata aggacccatg ccttccctct tcctgggccg   1020
tttcaacttt ttctttttct ttgtctatca acacacacac acctcacgac catgactgca   1080
caggatatta tcgccacata catcaccaaa tggtacgtga tagtaccact cgctttgatt   1140
gcttataggg tcctcgacta cttttacggc agatacttga tgtacaagct tggtgctaaa   1200
ccgtttttcc agaaacaaac agacggttat ttcggattca aagctccact tgaattgtta   1260
aaaaagaaga gtgacggtac cctcatagac ttcactctcg agcgtatcca agcgctcaat   1320
cgtccagata tcccaacttt tacattccca atcttttcca tcaaccttat cagcaccctt   1380
gagccggaga acatcaaggc tatcttggcc acccagttca acgatttctc cttgggcacc   1440
agacactcgc actttgctcc tttgttgggc gatggtatct ttaccttgga cggtgccggc   1500
tggaagcaca gcagatctat gttgagacca cagtttgcca gagaacagat ttcccacgtc   1560
aagttgttgg agccacacat gcaggtgttc ttcaagcacg tcagaaaggc acagggcaag   1620
acttttgaca tccaagaatt gtttttcaga ttgaccgtcg actccgccac tgagtttttg   1680
tttggtgaat ccgttgagtc cttgagagat gaatctattg ggatgtccat caatgcactt   1740
gactttgacg gcaaggctgg ctttgctgat gcttttaact actcgcagaa ctatttggct   1800
tcgagagcgg ttatgcaaca attgtactgg gtgttgaacg ggaaaaagtt taaggagtgc   1860
aacgctaaag tgcacaagtt tgctgactat tacgtcagca aggctttgga cttgacacct   1920
gaacaattgg aaaagcagga tggttatgtg ttcttgtacg agttggtcaa gcaaaccaga   1980
gacaggcaag tgttgagaga ccagttgttg aacatcatgg ttgccggtag agacaccacc   2040
gccggtttgt tgtcgtttgt tttctttgaa ttggccagaa acccagaggt gaccaacaag   2100
ttgagagaag aaatcgagga caagtttggt cttggtgaga atgctcgtgt tgaagacatt   2160
tcctttgagt cgttgaagtc atgtgaatac ttgaaggctg ttctcaacga aactttgaga   2220
ttgtacccat ccgtgccaca gaatttcaga gttgccacca aaaacactac ccttccaagg   2280
ggaggtggta aggacgggtt atctcctgtt ttggtcagaa agggtcaaac cgttatgtac   2340
ggtgtctacg ctgcccacag aaacccagct gtctacggta aggacgccct tgagtttaga   2400
ccagagaggt ggtttgagcc agagacaaag aagcttggct gggccttcct tccattcaac   2460
ggtggtccaa gaatttgctt gggacagcag tttgccttga cagaagcttc gtatgtcact   2520
gtcagattgc tccaagagtt tggacacttg tctatggacc ccaacaccga atatccacct   2580
aggaaaatgt cgcatttgac catgtccctt ttcgacggtg ccaacattga gatgtattag   2640
aggatcatgt gttatttttg attggtttag tctgtttgta gctattgatt aggttaattc   2700
acggattgtt atttattgat agggggtgcg tgtgtgtgtg tgtgttgcat tcacatggga   2760
tcgttccagg ttgttgtttc cttccatcct gttgagtcaa aaggagtttt gttttgtaac   2820
```

-continued tccggacgat gtcttagata gaaggtcgat ctccatgtga ttgtttgact gctactctga 2880
ttatgtaatc tgtaaagcct agacgttatg caagcatgtg attgtggttt ttgcaacctg 2940
tttgcacgac aaatgatcga cagtcgatta cgtaatccat attatttaga ggggtaataa 3000
aaaataaatg gcagccagaa tttcaaacat tttgcaaaca atgcaaaaga tgagaaactc 3060
caacagaaaa aataaaaaaa ctccgcagca ctccgaacca acaaaacaat gggggggcgcc 3120 agaattattg actattgtga cttttttttta tttttttccgt taactttcat tgcagtgaag 3180
tgtgttacac ggggtggtga tggtgttggt ttctacaatg caagggcaca gttgaaggtt 3240
tccacataac gttgcaccat atcaactcaa tttatcctca ttcatgtgat aaaagaagag 3300
ccaaaaggta attggcagac cccccaaggg gaacacggag tagaaagcaa tggaaacacg 3360
cccatgacag tgccatttag cccacaacac atctagtatt cttttttttt tttgtgcgca 3420
ggtgcacacc tggactttag ttattgcccc ataaagttaa caatctcacc tttggctctc 3480
ccagtgtctc cgcctccaga tgctcgtttt acaccctcga gctaacgaca acacaacacc 3540
catgagggga atgggcaaag ttaaacactt ttggtttcaa tgattcctat ttgctactct 3600
cttgttttgt gttttgattt gcaccatgtg aaataaacga caattatata taccttttcg 3660
tctgtcctcc aatgtctctt tttgctgcca ttttgctttt tgctttttgc ttttgcactc 3720
tctcccactc ccacaatcag tgcagcaaca cacaa 3755

<210> SEQ ID NO 10
<211> LENGTH: 3900
<212> TYPE: DNA
<213> ORGANISM: Candida tropicalis

<400> SEQUENCE: 10
gacatcataa tgacccggtt atttcgccct caggttgctt atttgagccg taaagtgcag 60
tagaaacttt gccttgggtt caaactctag tataatggtg ataactggtt gcactcttgc 120
cataggcatg aaaataggcc gttatagtac tatatttaat aagcgtagga gtataggatg 180
catatgaccg gtttttctat atttttaaga taatctctag taaattttgt attctcagta 240
ggatttcatc aaatttcgca accaattctg gcgaaaaaat gattctttta cgtcaaaagc 300
tgaatagtgc agtttaaagc acctaaaatc acatatacag cctctagata cgacagagaa 360
gctctttatg atctgaagaa gcattagaat agctactatg agccactatt ggtgtatata 420
ttagggattg gtgcaattaa gtacgtacta ataaacagaa gaaaatactt aaccaatttc 480
tggtgtatac ttagtggtga gggacctttt ctgaacattc gggtcaaact tttttttgga 540
gtgcgacatc gatttttcgt ttgtgtaata atagtgaacc tttgtgtaat aaatcttcat 600
gcaagacttg cataattcga gcttgggagt tcacgccaat ttgacctcgt tcatgtgata 660
aaagaaaagc caaaaggtaa ttagcagacg caatgggaac atggagtgga aagcaatgga 720
agcacgccca ggacggagta atttagtcca cactacatct ggggggtttt tttttgtgcg 780
caagtacaca cctggacttt agtttttgcc ccataaagtt aacaatctaa cctttggctc 840
tccaactctc tccgccccca aatattcgtt tttacaccct caagctagcg acagcacaac 900
acccattaga ggaatggggc aaagttaaac acttttggct tcaatgattc ctattcgcta 960
ctacattctt ctcttgtttt gtgctttgaa ttgcaccatg tgaaataaac gacaattata 1020 tataccttttt catccctcct cctatatctc tttttgctac attttgtttt ttacgtttct 1080
tgcttttgca ctctcccact cccacaaaga aaaaaaaact acactatgtc gtcttctcca 1140

-continued

```
tcgtttgccc aagaggttct cgctaccact agtccttaca tcgagtactt tcttgacaac   1200
tacaccagat ggtactactt catacctttg gtgcttcttt cgttgaactt tataagtttg   1260
ctccacacaa ggtacttgga acgcaggttc cacgccaagc cactcggtaa ctttgtcagg   1320
gaccctacgt ttggtatcgc tactccgttg cttttgatct acttgaagtc gaaaggtacg   1380
gtcatgaagt ttgcttgggg cctctggaac aacaagtaca tcgtcagaga cccaaagtac   1440
aagacaactg ggctcaggat tgttggcctc ccattgattg aaaccatgga cccagagaac   1500
atcaaggctg ttttggctac tcagttcaat gatttctctt tgggaaccag acacgatttc   1560
ttgtactcct tgttgggtga cggtattttc accttggacg gtgctggctg gaaacatagt   1620
agaactatgt tgagaccaca gtttgctaga gaacaggttt ctcacgtcaa gttgttggag   1680
ccacacgttc aggtgttctt caagcacgtt agaaagcacc gcggtcaaac gttcgacatc   1740
caagaattgt tcttcaggtt gaccgtcgac tccgccaccg agttcttgtt tggtgagtct   1800
gctgaatcct tgagggacga atctattgga ttgaccccaa ccaccaagga tttcgatggc   1860
agaagagatt tcgctgacgc tttcaactat tcgcagactt accaggccta cagatttttg   1920
ttgcaacaaa tgtactggat cttgaatggc tcggaattca gaaagtcgat tgctgtcgtg   1980
cacaagtttg ctgaccacta tgtgcaaaag gctttggagt tgaccgacga tgacttgcag   2040
aaacaagacg gctatgtgtt cttgtacgag ttggctaagc aaaccagaga cccaaaggtc   2100
ttgagagacc agttattgaa cattttggtt gccggtagag acacgaccgc cggtttgttg   2160
tcatttgttt tctacgagtt gtcaagaaac cctgaggtgt ttgctaagtt gagagaggag   2220
gtggaaaaca gatttggact cggtgaagaa gctcgtgttg aagagatctc gtttgagtcc   2280
ttgaagtctt gtgagtactt gaaggctgtc atcaatgaaa ccttgagatt gtacccatcg   2340
gttccacaca actttagagt tgctaccaga aacactaccc tcccaagagg tggtggtgaa   2400
gatggatact cgccaattgt cgtcaagaag ggtcaagttg tcatgtacac tgttattgct   2460
acccacagag acccaagtat ctacggtgcc gacgctgacg tcttcagacc agaaagatgg   2520
tttgaaccag aaactagaaa gttgggctgg gcatacgttc cattcaatgg tggtccaaga   2580
atctgtttgg gtcaacagtt tgccttgacc gaagcttcat acgtcactgt cagattgctc   2640
caggagtttg cacacttgtc tatggaccca gacaccgaat atccaccaaa attgcagaac   2700
accttgacct tgtcgctctt tgatggtgct gatgttagaa tgtactaagg ttgcttttcc   2760
ttgctaattt tcttctgtat agcttgtgta tttaaattga atcggcaatt gatttttctg   2820
ataccaataa ccgtagtgcg atttgaccaa aaccgttcaa actttttgtt ctctcgttga   2880
cgtgctcgct catcagcact gtttgaagac gaaagagaaa attttttgta aacaacactg   2940
tccaaattta cccaacgtga accattatgc aaatgagcgg ccctttcaac tggtcgctgg   3000
aagcattcgg ggatatctac aacgccctta agtttgaaac agacattgat ttagacacca   3060
tagatttcag cggcatcaag aatgaccttg cccacatttt gacgacccca acaccactgg   3120
aagaatcacg ccagaaacta ggcgatggat ccaagcctgt gaccttgccc aatggagacg   3180
aagtggagtt gaaccaagcg ttcctagaag ttaccacatt attgtcgaat gagtttgact   3240
tggaccaatt gaacgcggca gagttgttat actacgctgg cgacatatcc tacaagaagg   3300
gcacatcaat cgcagacagt gccagattgt cttattattt gagagcaaac tacatcttga   3360
acatacttgg gtatttgatt tcgaagcagc gattggattt gatagtcacg gacaacgacg   3420
cgttgtttga tagtattttg aaaagttttg aaaagatcta caagttgata agcgtgttga   3480
acgatatgat tgacaagcaa aaggtgacaa gcgacatcaa cagtctagca ttcatcaatt   3540
```

-continued gcatcaacta ctcgagaggt caactattct ccgcacacga acttttggga ctggttttgt 3600
ttggattggt cgacatctat ttcaaccagt ttggcacatt agacaactac aagaaggtat 3660
tggcattgat actgaagaac atcagcgatg aagacatctt gatcatacac ttcctcccat 3720
cgacactaca attgtttaag ctggtgttgg acaagaaaga cgacgctgca gttgaacagt 3780
tctacaagta catcacttca acagtgtcac gagactacaa ctccaacatc ggctccacag 3840
ccaaagatga tatcgatttg tccaaaacca aactcagtgg ctttgaggtg ttgacgagtt 3900

<210> SEQ ID NO 11
<211> LENGTH: 3668
<212> TYPE: DNA
<213> ORGANISM: Candida tropicalis

<400> SEQUENCE: 11
cctgcagaat tcgcggccgc gtcgacagag tagcagttat gcaagcatgt gattgtggtt 60
tttgcaacct gtttgcacga caaatgatcg acagtcgatt acgtaatcca tattatttag 120
aggggtaata aaaaataaat ggcagccaga atttcaaaca ttttgcaaac aatgcaaaag 180
atgagaaact ccaacagaaa aaataaaaaa actccgcagc actccgaacc aacaaaacaa 240
tggggggcgc cagaattatt gactattgtg acttttttt attttttccg ttaactttca 300
ttgcagtgaa gtgtgttaca cggggtggtg atggtgttgg tttctacaat gcaagggcac 360
agttgaaggt ttccacataa cgttgcacca tatcaactca atttatcctc attcatgtga 420
taaaagaaga gccaaaaggt aattggcaga ccccccaagg ggaacacgga gtagaaagca 480
atggaaacac gcccatgaca gtgccattta gcccacaaca catctagtat tcttttttt 540 ttttgtgcgc aggtgcacac ctggacttta gttattgccc cataaagtta acaatctcac 600
ctttggctct cccagtgtct ccgcctccag atgctcgttt tacaccctcg agctaacgac 660
aacacaacac ccatgagggg aatgggcaaa gttaaacact tttggtttca atgattccta 720
tttgctactc tcttgttttg tgttttgatt tgcaccatgt gaaataaacg acaattatat 780
ataccttttc gtctgtcctc caatgtctct ttttgctgcc attttgcttt ttgctttttg 840
cttttgcact ctctcccact cccacaatca gtgcagcaac acacaaagaa gaaaaataaa 900
aaaacctaca ctatgtcgtc ttctccatcg tttgctcagg aggttctcgc taccactagt 960
ccttacatcg agtactttct tgacaactac accagatggt actacttcat ccctttggtg 1020
cttctttcgt tgaacttcat cagcttgctc cacacaaagt acttggaacg caggttccac 1080
gccaagccgc tcggtaacgt cgtgttggat cctacgtttg gtatcgctac tccgttgatc 1140
ttgatctact taaagtcgaa aggtacagtc atgaagtttg cctggagctt ctggaacaac 1200
aagtacattg tcaaagaccc aaagtacaag accactggcc ttagaattgt cggcctccca 1260
ttgattgaaa ccatagaccc agagaacatc aaagctgtgt tggctactca gttcaacgat 1320
ttctccttgg gaactagaca cgatttcttg tactccttgt tgggcgatgg tatttttacc 1380
ttggacggtg ctggctggaa acacagtaga actatgttga gaccacagtt tgctagagaa 1440
caggtttccc acgtcaagtt gttggaacca cacgttcagg tgttcttcaa gcacgttaga 1500
aaacaccgcg gtcagacttt tgacatccaa gaattgttct tcagattgac cgtcgactcc 1560
gccaccgagt tcttgtttgg tgagtctgct gaatccttga gagacgactc tgttggtttg 1620
accccaacca ccaaggattt cgaaggcaga ggagatttcg ctgacgcttt caactactcg 1680
cagacttacc aggcctacag atttttgttg caacaaatgt actggatttt gaatggcgcg 1740

-continued

```
gaattcagaa agtcgattgc catcgtgcac aagtttgctg accactatgt gcaaaaggct   1800

ttggagttga ccgacgatga cttgcagaaa caagacggct atgtgttctt gtacgagttg   1860

gctaagcaaa ctagagaccc aaaggtcttg agagaccagt tgttgaacat tttggttgcc   1920

ggtagagaca cgaccgccgg tttgttgtcg tttgtgttct acgagttgtc gagaaaccct   1980

gaagtgtttg ccaagttgag agaggaggtg gaaaacagat ttggactcgg cgaagaggct   2040

cgtgttgaag agatctcttt tgagtccttg aagtcctgtg agtacttgaa ggctgtcatc   2100

aatgaagcct tgagattgta cccatctgtt ccacacaact tcagagttgc caccagaaac   2160

actacccttc caagaggcgg tggtaaagac ggatgctcgc caattgttgt caagaagggt   2220

caagttgtca tgtacactgt cattggtacc cacagagacc caagtatcta cggtgccgac   2280

gccgacgtct tcagaccaga aagatggttc gagccagaaa ctagaaagtt gggctgggca   2340

tatgttccat tcaatggtgg tccaagaatc tgtttgggtc agcagtttgc cttgactgaa   2400

gcttcatacg tcactgtcag attgctccaa gagtttggaa acttgtccct ggatccaaac   2460

gctgagtacc caccaaaatt gcagaacacc ttgaccttgt cactctttga tggtgctgac   2520

gttagaatgt tctaaggttg cttatccttg ctagtgttat ttatagtttg tgtatttaaa   2580

ttgaatcggc gattgatttt tctggtacta ataactgtag tgggttttga ccaaaaccgt   2640

tcaaactttt tttttttttt tcttccccct accttcgttg ctcgctcatc agcactgttt   2700

gaaaacgaaa aaagaaaatt ttttgtaaac aacattgccc aaacttaccc aacgtgaacc   2760

attataacca aatgagcggc gctttcaact ggtcactgga ggcattcggg gatatctaca   2820

acacccttaa gtttgaggaa gacattgatt tagacaccat agatttcagc ggcatcaaga   2880

atgaccttgt ccacattttg acaaccccaa caccactgga agaatcgcgc cagaaactag   2940

gcgatggatc caagcctgtg gccttgccca atggagacga agtggagttg aaccaagcgt   3000

tcctagaagt taccacatta ttgtcgaacg agtttgactt ggaccaattg aacgcggccg   3060

agttgttata ctacgccggc gacatatcct acaagaaggg cacatcaatt gccgacagtg   3120

ccagattgtc ttactatttg agagcaaact acatcttgaa catacttggg tactttattt   3180

cgaagcagcg attggatgtg atagtcaccg acaacaacgc gttgtttgat aatattttga   3240

aaagttttga aaagatctac aagttgataa gcgcgttgaa cgatatgatt gacaagcaaa   3300

aggtgacaag cgacatcaac agtctagcat ttatcaactg catcaactac tcgaggggtc   3360

aactattctc cgcacacgaa cttttgggac tggttttgtt tggattggtt gacaactatt   3420

tcaaccagtt tggctcatta gacaactaca agaaagtatt ggcattgata ctgaagaaca   3480

tcagtgatga agatatcttg atcgtacgct tcctcccatc gacactacaa ttgtttaagc   3540

tggtgttgga taagaaagac gacgccactg ttgaccagtt ctacaagtac atcacctcaa   3600

cagtgtcgca agactacaac tccaacatcg gagccacagc caaagatgat atcgatttgt   3660

ccaaagcc                                                            3668
```

<210> SEQ ID NO 12
<211> LENGTH: 3348
<212> TYPE: DNA
<213> ORGANISM: Candida tropicalis

<400> SEQUENCE: 12

```
gatgtggtgc ttgatttctc gagacacatc cttgtgaggt gccatgaatc tgtacctgtc     60

tgtaagcaca gggaactgct tcaacacctt attgcatatt ctgtctattg caagcgtgtg    120

ctgcaacgat atctgccaag gtatatagca gaacgtgctg atggttcctc cggtcatatt    180
```

-continued

```
ctgttggtag ttctgcaggt aaatttggat gtcaggtagt ggagggaggt ttgtatcggt    240
tgtgttttct tcttcctctc tctctgattc aacctccacg tctccttcgg gttctgtgtc    300
tgtgtctgag tcgtactgtt ggattaagtc catcgcatgt gtgaaaaaaa gtagcgctta    360
tttagacaac cagttcgttg ggcgggtatc agaaatagtc tgttgtgcac gaccatgagt    420
atgcaacttg acgagacgtc gttaggaatc cacagaatga tagcaggaag cttactacgt    480
gagagattct gcttagagga tgttctcttc ttgttgattc cattaggtgg gtatcatctc    540
cggtggtgac aacttgacac aagcagttcc gagaaccacc cacaacaatc accattccag    600
ctatcacttc tacatgtcaa cctacgatgt atctcatcac catctagttt cttggcaatc    660
gtttatttgt tatgggtcaa catccaatac aactccacca atgaagaaga aaaacggaaa    720
gcagaatacc agaatgacag tgtgagttcc tgaccattgc taatctatgg ctatatctag    780
tttgctatcg tgggatgtga tctgtgtcgt cttcatttgc gtttgtgttt atttcgggta    840
tgaatattgt tatactaaat acttgatgca caaacatggc gctcgagaaa tcgagaatgt    900
gatcaacgat gggttctttg ggttccgctt acctttgcta ctcatgcgag ccagcaatga    960
gggccgactt atcgagttca gtgtcaagag attcgagtcg gcgccacatc cacagaacaa   1020
gacattggtc aaccgggcat tgagcgttcc tgtgatactc accaaggacc cagtgaatat   1080
caaagcgatg ctatcgaccc agtttgatga cttttccctt gggttgagac tacaccagtt   1140
tgcgccgttg ttggggaaag gcatctttac tttggacggc ccagagtgga agcagagccg   1200
atctatgttg cgtccgcaat ttgccaaaga tcgggtttct catatcctgg atctagaacc   1260
gcattttgtg ttgcttcgga agcacattga tggccacaat ggagactact tcgacatcca   1320
ggagctctac ttccggttct cgatggatgt ggcgacgggg tttttgtttg gcgagtctgt   1380
ggggtcgttg aaagacgaag atgcgaggtt cctggaagca ttcaatgagt cgcagaagta   1440
tttggcaact agggcaacgt tgcacgagtt gtactttctt tgtgacgggt ttaggtttcg   1500
ccagtacaac aaggttgtgc gaaagttctg cagccagtgt gtccacaagg cgttagatgt   1560
tgcaccggaa gacaccagcg agtacgtgtt tctccgcgag ttggtcaaac acactcgaga   1620
tcccgttgtt ttacaagacc aagcgttgaa cgtcttgctt gctggacgcg acaccaccgc   1680
gtcgttatta tcgtttgcaa catttgagct agcccggaat gaccacatgt ggaggaagct   1740
acgagaggag gttatcctga cgatgggacc gtccagtgat gaaataaccg tggccgggtt   1800
gaagagttgc cgttacctca aagcaatcct aaacgaaact cttcgactat acccaagtgt   1860
gcctaggaac gcgagatttg ctacgaggaa tacgacgctt cctcgtggcg gaggtccaga   1920
tggatcgttt ccgattttga taagaaaggg ccagccagtg gggtatttca tttgtgctac   1980
acacttgaat gagaaggtat atgggaatga tagccatgtg tttcgaccgg agagatgggc   2040
tgcgttagag ggcaagagtt tgggctggtc gtatcttcca ttcaacggcg gcccgagaag   2100
ctgccttggt cagcagtttg caatccttga agcttcgtat gttttggctc gattgacaca   2160
gtgctacacg acgatacagc ttagaactac cgagtaccca ccaaagaaac tcgttcatct   2220
cacgatgagt cttctcaacg gggtgtacat ccgaactaga acttgattat gtgtttatgg   2280
ttaatcgggg caaagcactg caagtcattg atgtttgtgg aagcccagca ttggtgttcc   2340
ggagcatcaa taaccaatgt cttgaagggt ttgattttct tgaccttctt cttcctgagc   2400
ttctttccgt caaacttgta cagaatggcc atcatttcag gaacaaccac gtacgacggc   2460
cggtaccgca tctggagtat ctcgccgtcg ttcaagtagc acgaaaacag caacgacgtc   2520
```

-continued

```
accatctgct tcccaatctt gacacccaca gataccoctg cggcttcatg gatcaaaaac   2580

gtcggcaacc ccgcgtatat gtccatgtaa ttctccatgg ccacctccat caacacactg   2640

atggagcgac tgacggtgcc accactgccc tcggttgagt caaggcagta tgatgccggg   2700

atccagtact ccaatgggaa cctctgcacg gtgtcgctgc agtttttgag gcgtatttcg   2760

atccatgatc gttctttggt gctgtagtat aacgagctct tggtgtcctt gaaatggaac   2820

aggttggatg tgttgttgag tttgtctgcg tgcttggttt gcaagtcttc gatcgagcgt   2880

agtgagtaga cagttggcgg gggtggtggc tcgggcttta ttctgtgttt gtgtttcctt   2940

cttagtcttg gaatgacgct gttatcgacg gttcgtagta taagtagcgc caatatgaga   3000

atgtatatcc gcatcaccca agactcttca gcctgttaca acgactgagg ctgttggccg   3060

tgtgaccaat tggtttcttt ggtgacctag attggtcccg cagggaaagc aagggctgct   3120

agggggcat accaaacaag gtcgtgtaat cagtatctat ggtgctacca tgtgtgtggt   3180

tgggggaaa ttcccgcatt tttgtgtaac gaaagttcta gaaagttctc gtgggttctg   3240

agaatctgct ggaaccatcc acccgcattt ccgttgccaa agtgggaaga gcaatcaacc   3300

caccctgctt tgcccaatca gccattcccc tgggaatata aattcaac                3348
```

<210> SEQ ID NO 13
<211> LENGTH: 3826
<212> TYPE: DNA
<213> ORGANISM: Candida tropicalis

<400> SEQUENCE: 13

```
tggagtcgcc agacttgctc acttttgact cccttcgaaa ctcaaagtac gttcaggcgg     60

tgctcaacga aacgctccgt atctacccgg gggtaccacg aaacatgaag acagctacgt    120

gcaacacgac gttgccacgc ggaggaggca aagacggcaa ggaacctatc ttggtgcaga    180

agggacagtc cgttgggttg attactattg ccacgcagac ggacccagag tattttgggg    240

ccgacgctgg tgagtttaag ccggagagat ggtttgattc aagcatgaag aacttggggt    300

gtaaatactt gccgttcaat gctgggccac ggacttgctt ggggcagcag tacactttga    360

ttgaagcgag ctacttgcta gtccggttgg cccagaccta ccgggcaata gatttgcagc    420

caggatcggc gtacccacca agaaagaagt cgttgatcaa catgagtgct gccgacgggg    480

tgtttgtaaa gctttataag gatgtaacgg tagatggata gttgtgtagg aggagcggag    540

ataaattaga tttgattttg tgtaaggttt tggatgtcaa cctactccgc acttcatgca    600

gtgtgtgtga cacaagggtg tactacgtgt gcgtgtgcgc caagagacag cccaaggggg    660

tggtagtgtg tgttggcgga agtgcatgtg acacaacgcg tgggttctgg ccaatggtgg    720

actaagtgca ggtaagcagc gacctgaaac attcctcaac gcttaagaca ctggtggtag    780

agatgcggac caggctattc ttgtcgtgct acccggcgca tggaaaatca actgcgggaa    840

gaataaattt atccgtagaa tccacagagc ggataaattt gcccacctcc atcatcaacc    900

acgccgccac taactacatc actcccctat tttctctctc tctctttgtc ttactccgct    960

cccgtttcct tagccacaga tacacaccca ctgcaaacag cagcaacaat tataaagata   1020

cgccaggccc accttctttc tttttcttca cttttttgac tgcaactttc tacaatccac   1080

cacagccacc accacagccg ctatgattga acaactccta gaatattggt atgtcgttgt   1140

gccagtgttg tacatcatca aacaactcct tgcatacaca aagactcgcg tcttgatgaa   1200

aaagttgggt gctgctccag tcacaaacaa gttgtacgac aacgctttcg gtatcgtcaa   1260

tggatggaag gctctccagt tcaagaaaga gggcagggct caagagtaca acgattacaa   1320
```

-continued gtttgaccac tccaagaacc caagcgtggg cacctacgtc agtattcttt tcggcaccag 1380
gatcgtcgtg accaaagatc cagagaatat caaagctatt ttggcaaccc agtttggtga 1440
tttttctttg ggcaagaggc acactctttt taagcctttg ttaggtgatg ggatcttcac 1500
attggacggc gaaggctgga agcacagcag agccatgttg agaccacagt ttgccagaga 1560
acaagttgct catgtgacgt cgttggaacc acacttccag ttgttgaaga agcatattct 1620
taagcacaag ggtgaatact ttgatatcca ggaattgttc tttagattta ccgttgattc 1680
ggccacggag ttcttatttg gtgagtccgt gcactcctta aaggacgaat ctattggtat 1740
caaccaagac gatatagatt ttgctggtag aaaggacttt gctgagtcgt tcaacaaagc 1800
ccaggaatac ttggctatta gaaccttggt gcagacgttc tactggttgg tcaacaacaa 1860
ggagtttaga gactgtacca agctggtgca caagttcacc aactactatg ttcagaaagc 1920
tttggatgct agcccagaag agcttgaaaa gcaaagtggg tatgtgttct tgtacgagct 1980
tgtcaagcag acaagagacc ccaatgtgtt gcgtgaccag tctttgaaca tcttgttggc 2040
cggaagagac accactgctg ggttgttgtc gtttgctgtc tttgagttgg ccagacaccc 2100
agagatctgg gccaagttga gagaggaaat tgaacaacag tttggtcttg gagaagactc 2160
tcgtgttgaa gagattacct ttgagagctt gaagagatgt gagtacttga aagcgttcct 2220
taatgaaacc ttgcgtattt acccaagtgt cccaagaaac ttcagaatcg ccaccaagaa 2280
cacgacattg ccaaggggcg gtggttcaga cggtacctcg ccaatcttga tccaaaaggg 2340
agaagctgtg tcgtatggta tcaactctac tcatttggac cctgtctatt acggccctga 2400
tgctgctgag ttcagaccag agagatggtt tgagccatca accaaaaagc tcggctgggc 2460
ttacttgcca ttcaacggtg gtccaagaat ctgtttgggt cagcagtttg ccttgacgga 2520
agctggctat gtgttggtta gattggtgca agagttctcc cacgttaggc tggacccaga 2580
cgaggtgtac ccgccaaaga ggttgaccaa cttgaccatg tgtttgcagg atggtgctat 2640
tgtcaagttt gactagcggc gtggtgaatg cgtttgattt tgtagtttct gtttgcagta 2700
atgagataac tattcagata aggcgagtgg atgtacgttt tgtaagagtt tccttacaac 2760
cttggtgggg tgtgtgaggt tgaggttgca tcttggggag attacacctt ttgcagctct 2820
ccgtatacac ttgtactctt tgtaacctct atcaatcatg tggggggggg ggttcattgt 2880
ttggccatgg tggtgcatgt taaatccgcc aactacccaa tctcacatga aactcaagca 2940
cactaaaaaa aaaaaagatg ttgggggaaa actttggttt cccttcttag taattaaaca 3000
ctctcactct cactctcact ctctccactc agacaaacca accacctggg ctgcagacaa 3060
ccagaaaaaa aaagaacaaa atccagatag aaaaacaaag ggctggacaa ccataaataa 3120
acaatctagg gtctactcca tcttccactg tttcttcttc ttcagactta gctaacaaac 3180
aactcacttc accatggatt acgcaggcat cacgcgtggc tccatcagag gcgaggcctt 3240
gaagaaactc gcagaattga ccatccagaa ccagccatcc agcttgaaag aaatcaacac 3300
cggcatccag aaggacgact ttgccaagtt gttgtctgcc accccgaaaa tccccaccaa 3360
gcacaagttg aacggcaacc acgaattgtc tgaggtcgcc attgccaaaa aggagtacga 3420
ggtgttgatt gccttgagcg acgccacaaa agacccaatc aaagtgacct cccagatcaa 3480
gatcttgatt gacaagttca aggtgtactt gtttgagttg cctgaccaga agttctccta 3540
ctccatcgtg tccaactccg tcaacatcgc cccctggacc ttgctcgggg agaagttgac 3600
cacgggcttg atcaacttgg ccttccagaa caacaagcag cacttggacg aggtcattga 3660

-continued

```
catcttcaac gagttcatcg acaagttctt tggcaacacg gagccgcaat tgaccaactt   3720

cttgaccttg tgcggtgtgt tggacgggtt gattgaccat gccaacttct tgagcgtgtc   3780

ctcgcggacc ttcaagatct tcttgaactt ggactcgtat gtggac                   3826
```

<210> SEQ ID NO 14
<211> LENGTH: 3910
<212> TYPE: DNA
<213> ORGANISM: Candida tropicalis

<400> SEQUENCE: 14

```
ttacaatcat ggagctcgct aggaacccag atgtctggga gaagctccgc gaagaggtca     60

acacgaactt tggcatggag tcgccagact tgctcacttt tgactctctt agaagctcaa    120

agtacgttca ggcggtgctc aacgaaacgc ttcgtatcta cccgggggtg ccacgaaaca    180

tgaagacagc tacgtgcaac acgacgttgc cgcgtggagg aggcaaagac ggtaaggaac    240

ctattttggt gcagaagggc cagtccgttg ggttgattac tattgccacg cagacggacc    300

cagagtattt tggggcagat gctggtgagt tcaaaccgga gagatggttt gattcaagca    360

tgaagaactt ggggtgtaag tacttgccgt tcaatgctgg gccccggact tgtttggggc    420

agcagtacac tttgattgaa gcgagctatt tgctagtcag gttggcgcag acctaccggg    480

taatcgattt gctgccaggg tcggcgtacc caccaagaaa gaagtcgttg atcaatatga    540

gtgctgccga tggggtggtt gtaaagtttc acaaggatct agatggatat gtaaggtgtg    600

taggaggagc ggagataaat tagatttgat tttgtgtaag gtttagcacg tcaagctact    660

ccgcactttg tgtgtaggga gcacatactc cgtctgcgcc tgtgccaaga gacggcccag    720

gggtagtgtg tggtggtgga agtgcatgtg acacaatacc ctggttctgg ccaattgggg    780

atttagtgta ggtaagctgc gacctgaaac actcctcaac gcttgagaca ctggtgggta    840

gagatgcggg ccaggaggct attcttgtcg tgctacccgt gcacggaaaa tcgattgagg    900

gaagaacaaa tttatccgtg aaatccacag agcggataaa tttgtcacat tgctgcgttg    960

cccacccaca gcattctctt ttctctctct ttgtcttact ccgctcctgt ttccttatcc   1020

agaaatacac accaactcat ataaagatac gctagcccag ctgtctttct ttttcttcac   1080

tttttttggt gtgttgcttt tttggctgct actttctaca accaccacca ccaccaccac   1140

catgattgaa caaatcctag aatattggta tattgttgtg cctgtgttgt acatcatcaa   1200

acaactcatt gcctacagca agactcgcgt cttgatgaaa cagttgggtg ctgctccaat   1260

cacaaaccag ttgtacgaca acgttttcgg tatcgtcaac ggatggaagg ctctccagtt   1320

caagaaagag ggcagagctc aagagtacaa cgatcacaag tttgacagct ccaagaaccc   1380

aagcgtcggc acctatgtca gtattctttt tggcaccaag attgtcgtga ccaaggatcc   1440

agagaatatc aaagctattt tggcaaccca gtttggcgat ttttctttgg gcaagagaca   1500

cgctcttttt aaacctttgt taggtgatgg gatcttcacc ttggacggcg aaggctggaa   1560

gcatagcaga tccatgttaa gaccacagtt tgccagagaa caagttgctc atgtgacgtc   1620

gttggaacca cacttccagt tgttgaagaa gcatatcctt aaacacaagg gtgagtactt   1680

tgatatccag gaattgttct ttagatttac tgtcgactcg gccacggagt tcttatttgg   1740

tgagtccgtg cactccttaa aggacgaaac tatcggtatc aaccaagacg atatagattt   1800

tgctggtaga aaggactttg ctgagtcgtt caacaaagcc caggagtatt tgtctattag   1860

aattttggtg cagaccttct actggttgat caacaacaag gagtttagag actgtaccaa   1920

gctggtgcac aagtttacca actactatgt tcagaaagct ttggatgcta ccccagagga   1980
```

-continued acttgaaaag caaggcgggt atgtgttctt gtatgagctt gtcaagcaga cgagagaccc 2040
caaggtgttg cgtgaccagt ctttgaacat cttgttggca ggaagagaca ccactgctgg 2100
gttgttgtcc tttgctgtgt ttgagttggc cagaaaccca cacatctggg ccaagttgag 2160
agaggaaatt gaacagcagt ttggtcttgg agaagactct cgtgttgaag agattacctt 2220
tgagagcttg aagagatgtg agtacttgaa agcgttcctt aacgaaacct tgcgtgttta 2280
cccaagtgtc ccaagaaact tcagaatcgc caccaagaat acaacattgc caaggggtgg 2340
tggtccagac ggtacccagc caatcttgat ccaaaaggga gaaggtgtgt cgtatggtat 2400
caactctacc cacttagatc ctgtctatta tggccctgat gctgctgagt tcagaccaga 2460
gagatggttt gagccatcaa ccagaaagct cggctgggct tacttgccat tcaacggtgg 2520
gccacgaatc tgtttgggtc agcagtttgc cttgaccgaa gctggttacg ttttggtcag 2580
attggtgcaa gagttctccc acattaggct ggacccagat gaagtgtatc caccaaagag 2640
gttgaccaac ttgaccatgt gtttgcagga tggtgctatt gtcaagtttg actagtacgt 2700
atgagtgcgt ttgattttgt agtttctgtt tgcagtaatg agataactat tcagataagg 2760
cgggtggatg tacgttttgt aagagtttcc ttacaaccct ggtgggtgtg tgaggttgca 2820
tcttagggag agatagcacc ttttgcagct ctccgtatac agttttactc tttgtaacct 2880
atgccaatca tgtggggatt cattgtttgc ccatggtggt gcatgcaaaa tccccccaac 2940
tacccaatct cacatgaaac tcaagcacac tagaaaaaaa agatgttgcg tgggttcttt 3000
tgatgttggg gaaaactttc gtttcctttc tcagtaatta aacgttctca ctcagacaaa 3060
ccacctgggc tgcagacaac cagaaaaaac aaaatccaga tagaagaaga aagggctgga 3120
caaccataaa taaacaacct agggtccact ccatctttca cttcttcttc ttcagactta 3180
tctaacaaac gactcacttc accatggatt acgcaggtat cacgcgtggg tccatcagag 3240
gcgaagcctt gaagaaactc gccgagttga ccatccagaa ccagccatcc agcttgaaag 3300
aaatcaacac cggcatccag aaggacgact ttgccaagtt gttgtcttcc accccgaaaa 3360
tccacaccaa gcacaagttg aatggcaacc acgaattgtc cgaagtcgcc attgccaaaa 3420
aggagtacga ggtgttgatt gccttgagcg acgccacgaa agaaccaatc aaagtcacct 3480
cccagatcaa gatcttgatt gacaagttca aggtgtactt gtttgagttg cccgaccaga 3540
agttctccta ctccatcgtg tccaactccg ttaacattgc cccctggacc ttgctcggtg 3600
agaagttgac cacgggcttg atcaacttgg cgttccagaa caacaagcag cacttggacg 3660
aagtcatcga catcttcaac gagttcatcg acaagttctt tggcaacaca gagccgcaat 3720
tgaccaactt cttgaccttg tccggtgtgt tggacgggtt gattgaccat gccaacttct 3780
tgagcgtgtc ctccaggacc ttcaagatct tcttgaactt ggactcgttt gtggacaact 3840
cggacttctt gaacgacgtg gagaactact ccgacttttt gtacgacgag ccgaacgagt 3900
accagaactt 3910

<210> SEQ ID NO 15
<211> LENGTH: 3150
<212> TYPE: DNA
<213> ORGANISM: Candida tropicalis

<400> SEQUENCE: 15
gaattctttg gatctaattc cagctgatct tgctaatcct tatcaacgta gttgtgatca 60
ttgtttgtct gaattataca caccagtgga agaatatggt ctaatttgca cgtcccactg 120

-continued

```
gcattgtgtg tttgtggggg gggggggggtg cacacatttt tagtgccatt ctttgttgat    180
taccccctccc ccctatcatt cattcccaca ggattagttt tttcctcact ggaattcgct    240
gtccacctgt caacccccccc cccccccccc cccactgccc taccctgccc tgccctgcac    300
gtcctgtgtt ttgtgctgtg tctttcccac gctataaaag ccctggcgtc cggccaaggt    360
ttttccaccc agccaaaaaa acagtctaaa aaatttggtt gatccttttt ggttgcaagg    420
ttttccacca ccacttccac cacctcaact attcgaacaa aagatgctcg atcagatctt    480
acattactgg tacattgtct tgccattgtt ggccattatc aaccagatcg tggctcatgt    540
caggaccaat tatttgatga agaaattggg tgctaagcca ttcacacacg tccaacgtga    600
cgggtggttg ggcttcaaat tcggccgtga attcctcaaa gcaaaaagtg ctgggagact    660
ggttgattta atcatctccc gtttccacga taatgaggac actttctcca gctatgcttt    720
tggcaaccat gtggtgttca ccagggaccc cgagaatatc aaggcgcttt tggcaaccca    780
gtttggtgat tttcattgg gcagcagggt caagttcttc aaaccattat tggggtacgg    840
tatcttcaca ttggacgccg aaggctggaa gcacagcaga gccatgttga gaccacagtt    900
tgccagagaa caagttgctc atgtgacgtc gttggaacca cacttccagt tgttgaagaa    960
gcatatcctt aaacacaagg gtgagtactt tgatatccag gaattgttct ttagatttac   1020
tgtcgactcg gccacggagt tcttatttgg tgagtccgtg cactccttaa aggacgagga   1080
aattggctac gacacgaaag acatgtctga agaaagacgc agatttgccg acgcgttcaa   1140
caagtcgcaa gtctacgtgg ccaccagagt tgctttacag aacttgtact ggttggtcaa   1200
caacaaagag ttcaaggagt gcaatgacat tgtccacaag tttaccaact actatgttca   1260
gaaagccttg gatgctaccc cagaggaact tgaaaagcaa ggcgggtatg tgttcttgta   1320
tgagcttgtc aagcagacga gagaccccaa ggtgttgcgt gaccagtctt tgaacatctt   1380
gttggcagga agagacacca ctgctgggtt gttgtccttt gctgtgtttg agttggccag   1440
aaacccacac atctgggcca agttgagaga ggaaattgaa cagcagtttg gtcttggaga   1500
agactctcgt gttgaagaga ttacctttga gagcttgaag agatgtgagt acttgaaggc   1560
cgtgttgaac gaaactttga gattacaccc aagtgtccca agaaacgcaa gatttgcgat   1620
taaagacacg actttaccaa gaggcggtgg ccccaacggc aaggatccta tcttgatcag   1680
gaaggatgag gtggtgcagt actccatctc ggcaactcag acaaatcctg cttattatgg   1740
cgccgatgct gctgatttta gaccggaaag atggtttgaa ccatcaacta gaaacttggg   1800
atgggctttc ttgccattca acggtggtcc aagaatctgt ttgggacaac agtttgcttt   1860
gactgaagcc ggttacgttt tggttagact tgttcaggag tttccaaact tgtcacaaga   1920
ccccgaaacc aagtacccac cacctagatt ggcacacttg acgatgtgct tgtttgacgg   1980
tgcacacgtc aagatgtcat aggtttcccc atacaagtag ttcagtaatt atacactgtt   2040
tttactttct cttcatacca aatggacaaa agttttaagc atgcctaaca acgtgaccgg   2100
acaattgtgt cgcactagta tgtaacaatt gtaaaaatag tgtacactaa tttgtggtgg   2160
ccggagataa attacagttt ggttttgtgt aaactcgcgg atatctctgg cagtttctct   2220
tctccgcagc agctttgcca cgggtttgct ctggggccaa caaattcaaa agggggagaa   2280
acttaacacc ccttatctct ccactctagg ttgtagctct tgtggggatg caattgtcgt   2340
acgtttttta tgttttgtct agactttgat gattacgttg gatttcttat gtctgaggcg   2400
tgcttgaaag aagtgtcaaa atgtgacagg cgacgctatt cgacatgaac gcgaaagggt   2460
tatttgcatc aatacgaggg gctgactcta gtctaggatg gcagtcctag gttgcaaaca   2520
```

-continued tgttgcacca tatccctcct ggagttggtc gacctcgcct acgccaccct cagcgatcgg 2580
cactttccgt tgttcaatat ttctccttcc cattgttcca ggggttatca acaacgttgc 2640
cggcctcctc cccaaattac aagaaaaata aattgtcgca cggcaccgat ctgtcaaaga 2700
tacagataaa ccttaaatct gcaaaaacaa gacccctccc catagcctag aagcaccagc 2760
aagatgatgg agcaactcct ccagtactgg tacatcgcac tctctgtatg gttcatcctt 2820
cgctacttgg cttcccacgc acgagccgtc tacttgcgcc acaagctcgg cgcggcgcca 2880
ttcacgcaca cccagtacga cggctggtat gggttcaagt ttgggcggga gtttctcaag 2940
gcgaagaaga tcgggcggca gacggacttg gtgcatgcgc ggttccgtgg cggcatggac 3000
accttctcga gctacacttt cggcatccat atcatcctta cccgggaccc ggagaacatc 3060
aaggcggtct tggcgacgca gttcgatgac ttctcgctcg gtggcaggat caggttcttg 3120
aagccgttgt tggggtatgg gatattcacg 3150

<210> SEQ ID NO 16
<211> LENGTH: 3579
<212> TYPE: DNA
<213> ORGANISM: Candida tropicalis

<400> SEQUENCE: 16
aaaaccgata caagaagaag acagtcaaca agaacgttaa tgtcaaccag gcgccaagaa 60
gacggtttgg cggacttgga agaatgtggc atttgcccat gatgtttatg ttctggagag 120
gtttttcaag gaatcgtcat cctccgccac cacaagaacc accagttaac gagatccata 180
ttcacaaccc accgcaaggt gacaatgctc aacaacaaca gcaacaacaa caaccccccac 240 aagaacagtg gaataatgcc agtcaacaaa gagtggtgac agacgaggga gaaaacgcaa 300
gcaacagtgg ttctgatgca agatcagcta caccgcttca tcaggaaaag caggagctcc 360
caccaccata tgcccatcac gagcaacacc agcaggttag tgtatagtag tctgtagtta 420
agtcaatgca atgtaccaat aagactatcc cttcttacaa ccaagttttc tgccgcgcct 480
gtctggcaac agatgctggc cgacacactt tcaactgagt ttggtctaga attcttgcac 540
atgcacgaca aggaaactct tacaaagaca acacttgtgc tctgatgcca cttgatcttg 600
ctaagcctta tcaacgtaat tgagatcatt gtttgtctga attatacaca ccagtggaag 660
aatctggtct aatctgcacg cctcatgggc attgtgtgtt ttgggggggg gggggggggt 720
gcacacattt ttagtgcgaa tgtttgtttg ctggttcccc ctcccccctc cccccctatca 780 tgcccacagg attagttttt tcctcactgg aattcgctgt ccacctgtca accccctcac 840
tgccctgccc tgccctgcac gccctgtgtt ttgtgctgtg gcactcccac gctataaaag 900
ccctggcgta cggccaaggt tttcctcac agccaaaaaa aaatttggct gatccttttg 960
ggctgcaagg tttttcacca ccaccaccac caccacctca actattcaaa caaaggatgc 1020
tcgaccagat cttccattac tggtacattg tcttgccatt gttggtcatt atcaagcaga 1080
tcgtggctca tgccaggacc aattatttga tgaagaagtt gggcgctaag ccattcacac 1140
atgtccaact agacgggtgg tttggcttca aatttggccg tgaattcctc aaagctaaaa 1200
gtgctgggag gcaggttgat ttaatcatct cccgtttcca cgataatgag gacactttct 1260
ccagctatgc ttttggcaac catgtggtgt tcaccaggga ccccgagaat atcaaggcgc 1320
ttttggcaac ccagtttggt gatttttcat tgggaagcag ggtcaaattc ttcaaaccat 1380
tgttggggta cggtatcttc accttggacg gcgaaggctg gaagcacagc agagccatgt 1440

-continued

```
tgagaccaca gtttgccaga gagcaagttg ctcatgtgac gtcgttggaa ccacatttcc   1500

agttgttgaa gaagcatatt cttaagcaca agggtgaata ctttgatatc caggaattgt   1560

tctttagatt taccgttgat tcagcgacgg agttcttatt tggtgagtcc gtgcactcct   1620

taagggacga ggaaattggc tacgatacga aggacatggc tgaagaaaga cgcaaatttg   1680

ccgacgcgtt caacaagtcg caagtctatt tgtccaccag agttgcttta cagacattgt   1740

actggttggt caacaacaaa gagttcaagg agtgcaacga cattgtccac aagttcacca   1800

actactatgt tcagaaagcc ttggatgcta ccccagagga acttgaaaaa caaggcgggt   1860

atgtgttctt gtacgagctt gccaagcaga cgaaagaccc caatgtgttg cgtgaccagt   1920

ctttgaacat cttgttggct ggaagggaca ccactgctgg gttgttgtcc tttgctgtgt   1980

ttgagttggc caggaaccca cacatctggg ccaagttgag agaggaaatt gaatcacact   2040

ttgggctggg tgaggactct cgtgttgaag agattacctt tgagagcttg aagagatgtg   2100

agtacttgaa agccgtgttg aacgaaacgt tgagattaca cccaagtgtc ccaagaaacg   2160

caagatttgc gattaaagac acgactttac caagaggcgg tggccccaac ggcaaggatc   2220

ctatcttgat cagaaagaat gaggtggtgc aatactccat ctcggcaact cagacaaatc   2280

ctgcttatta tggcgccgat gctgctgatt ttagaccgga aagatggttt gagccatcaa   2340

ctagaaactt gggatgggct tacttgccat tcaacggtgg tccaagaatc tgcttgggac   2400

aacagtttgc tttgaccgaa gccggttacg ttttggttag acttgttcag gaattcccta   2460

gcttgtcaca ggaccccgaa actgagtacc caccacctag attggcacac ttgacgatgt   2520

gcttgtttga cggggcatac gtcaagatgc aataggtttt ggtttgactt tgtttccata   2580

tgcaagtagt tcagtaatta cacactaatt tgtggtggcc ggcgataaat taccgtttgg   2640

ttttgtgtaa aaattcggac atctctggtg gtttcccttc tccgcagcag ctttgccacg   2700

ggtttgctct gcggccaaca aattcgaaag gggggggggg gggggagaaa gttaacaccc   2760

cctgttccca ccgtaggctg tagctcttgt ggggggatgt aattgtcgta cgttttcatg   2820

tttggcccag actttgatga ttacgtaggc tttcttatgt ctaaggcgtg cttgacacaa   2880

gtgtcaaaag gtgacaggcg acgttattcg acatgaacgc aaaagggtaa tttgcatcga   2940

tacgaggggt tgcctctggt ctaagaagga ccccccaggt tgcaaacatg ttgcactgca   3000

tcccactcag agttggtcga ccacgcctac gcttaccctc agcgatcggc actttccgtt   3060

gctcaatatt tctctccccc ctgcttcccc ccattgttcc agggattatc aacaacgttg   3120

ccggtctcct ctcccccccc tccccccagt tatgtacaag aaaattaaat tgtcgcacgg   3180

caccgatacg tcaaagatac agagaaacct taatccctcc catagcctag aagcatcaaa   3240

aagatgattg agcaactcct ccagtactgg tacattgcac tccctgtatg gttcattctc   3300

cgctacgtgg cttcccacgc acgaaccatc tacttgcgcc acaagctcgg cgcggcgccg   3360

ttcacgcaca cccagtacga cggatggtat gggttcaagt ttgggcggga gtttctcaag   3420

gcgaagaaga ttggaaggca gacggacttg gtgcatgcgc ggttccgtgg agggggcatg   3480

gatactttct cgagctatac tttcggcatc catatcattc ttactcggga cccggagaac   3540

atcaaggcgg tcttggcgac gcagttcgat gacttttcg                          3579
```

<210> SEQ ID NO 17
<211> LENGTH: 31
<212> TYPE: DNA
<213> ORGANISM: Primer

<400> SEQUENCE: 17

-continued ccttaattaa gaggtcgttg gttgagtttt c 31

<210> SEQ ID NO 18
<211> LENGTH: 29
<212> TYPE: DNA
<213> ORGANISM: Primer

<400> SEQUENCE: 18
ccttaattaa ttgataatga cgttgcggg 29

<210> SEQ ID NO 19
<211> LENGTH: 33
<212> TYPE: DNA
<213> ORGANISM: Primer

<400> SEQUENCE: 19
aggcgcgccg gagtccaaaa agaccaacct ctg 33

<210> SEQ ID NO 20
<211> LENGTH: 34
<212> TYPE: DNA
<213> ORGANISM: Primer

<400> SEQUENCE: 20
ccttaattaa tacgtggata ccttcaagca agtg 34

<210> SEQ ID NO 21
<211> LENGTH: 35
<212> TYPE: DNA
<213> ORGANISM: Primer

<400> SEQUENCE: 21
ccttaattaa gctcacgagt tttgggattt tcgag 35

<210> SEQ ID NO 22
<211> LENGTH: 35
<212> TYPE: DNA
<213> ORGANISM: Primer

<400> SEQUENCE: 22
gggtttaaac cgcagaggtt ggtctttttg gactc 35

<210> SEQ ID NO 23
<211> LENGTH: 10
<212> TYPE: DNA
<213> ORGANISM: Primer

<400> SEQUENCE: 23
gggtttaaac 10

<210> SEQ ID NO 24
<211> LENGTH: 9
<212> TYPE: DNA
<213> ORGANISM: Primer

<400> SEQUENCE: 24 aggcgcgcc 9

<210> SEQ ID NO 25
<211> LENGTH: 10
<212> TYPE: DNA
<213> ORGANISM: Primer

-continued

<400> SEQUENCE: 25
ccttaattaa 10

<210> SEQ ID NO 26
<211> LENGTH: 21
<212> TYPE: DNA
<213> ORGANISM: Primer

<400> SEQUENCE: 26
tcycaaacwg gtacwgcwga a 21

<210> SEQ ID NO 27
<211> LENGTH: 21
<212> TYPE: DNA
<213> ORGANISM: Primer

<400> SEQUENCE: 27
ggtttgggta aytcwactta t 21

<210> SEQ ID NO 28
<211> LENGTH: 20
<212> TYPE: DNA
<213> ORGANISM: Primer

<400> SEQUENCE: 28
cgttattayt cyatttcttc 20

<210> SEQ ID NO 29
<211> LENGTH: 20
<212> TYPE: DNA
<213> ORGANISM: Primer

<400> SEQUENCE: 29
gcmacaccrg tacctggacc 20

<210> SEQ ID NO 30
<211> LENGTH: 18
<212> TYPE: DNA
<213> ORGANISM: Primer

<400> SEQUENCE: 30
atcccaatcg taatcagc 18

<210> SEQ ID NO 31
<211> LENGTH: 18
<212> TYPE: DNA
<213> ORGANISM: Primer

<400> SEQUENCE: 31
acttgtcttc gtttagca 18

<210> SEQ ID NO 32
<211> LENGTH: 18
<212> TYPE: DNA
<213> ORGANISM: Primer

<400> SEQUENCE: 32
ctacgtctgt ggtgatgc 18

<210> SEQ ID NO 33
<211> LENGTH: 25
<212> TYPE: DNA
<213> ORGANISM: Primer

<400> SEQUENCE: 33
ctcgggaagc gcgccattgt gttgg          25

<210> SEQ ID NO 34
<211> LENGTH: 29
<212> TYPE: DNA
<213> ORGANISM: Primer

<400> SEQUENCE: 34
taatacgact cactataggg cgaattggc      29

<210> SEQ ID NO 35
<211> LENGTH: 30
<212> TYPE: DNA
<213> ORGANISM: Primer

<400> SEQUENCE: 35
gggttaatta acatacttca agcagtttgg    30

<210> SEQ ID NO 36
<211> LENGTH: 30
<212> TYPE: DNA
<213> ORGANISM: Primer

<400> SEQUENCE: 36
cccttaatta aggggggatg gaagtggccg    30

<210> SEQ ID NO 37
<211> LENGTH: 39
<212> TYPE: DNA
<213> ORGANISM: Primer

<400> SEQUENCE: 37
ataagaatgc ggccgctgaa cgagaaccac atccaggag    39

<210> SEQ ID NO 38
<211> LENGTH: 33
<212> TYPE: DNA
<213> ORGANISM: Primer

<400> SEQUENCE: 38
ccttaattaa ggataaccac atccatacgt cgc    33

<210> SEQ ID NO 39
<211> LENGTH: 23
<212> TYPE: DNA
<213> ORGANISM: Primer

<400> SEQUENCE: 39
cacaccaccc acgacgactt gtg            23

<210> SEQ ID NO 40
<211> LENGTH: 21
<212> TYPE: DNA
<213> ORGANISM: Primer

<400> SEQUENCE: 40
cttccgtgct gaacgactgc g              21

<210> SEQ ID NO 41
<211> LENGTH: 46
<212> TYPE: DNA

-continued

<213> ORGANISM: Primer

<400> SEQUENCE: 41
taatacgact cactataggg aggcacacca cccacgacga cttgtg 46

<210> SEQ ID NO 42
<211> LENGTH: 42
<212> TYPE: DNA
<213> ORGANISM: Primer

<400> SEQUENCE: 42
cttccgtgct gaacgactgc gaatcttagc gcccttcaag tt 42

<210> SEQ ID NO 43
<211> LENGTH: 222
<212> TYPE: DNA
<213> ORGANISM: vector

<400> SEQUENCE: 43
caggaaacag ctatgaccat gattacgcca agcttggtac cgagctcgga tccactagta 60
acggccgcca gtgtgctgga attcgccctt aagggcgaat tctgcagata tccatcacac 120
tggcggccgc tcgagcatgc atctagaggg cccaattcgc cctatagtga gtcgtattac 180
aattcactgg ccgtcgtttt acaacgtcgt gactgggaaa ac 222

<210> SEQ ID NO 44
<211> LENGTH: 222
<212> TYPE: DNA
<213> ORGANISM: vector

<400> SEQUENCE: 44
gtcctttgtc gatactggta ctaatgcggt tcgaaccatg gctcgagcct aggtgatcat 60
tgccggcggt cacacgacct taagccggaa ttcccgctta agacgtctat aggtagtgtg 120
accgccggcg agctcgtacg tagatctccc gggttaagcg ggatatcact cagcataatg 180
ttaagtgacc ggcagcaaaa tgttgcagca ctgacccttt tg 222

<210> SEQ ID NO 45
<211> LENGTH: 1712
<212> TYPE: DNA
<213> ORGANISM: Candida tropicalis

<400> SEQUENCE: 45
ggtaccgagc tcacgagttt tgggattttc gagtttggat tgtttccttt gttgattgaa 60
ttgacgaaac cagaggtttt caagacagat aagattgggt ttatcaaaac gcagtttgaa 120
atattccagt tggtttccaa gatatcttga agaagattga cgatttgaaa tttgaagaag 180
tggagaagat ctggtttgga ttgttggaga atttcaagaa tctcaagatt tactctaacg 240
acgggtacaa cgagaattgt attgaattga tcaagaacat gatcttggtg ttacagaaca 300
tcaagttctt ggaccagact gagaatgcca cagatataca aggcgtcatg tgataaaatg 360
gatgagattt atcccacaat tgaagaaaga gtttatggaa agtggtcaac cagaagctaa 420
acaggaagaa gcaaacgaag aggtgaaaca agaagaagaa ggtaaataag tattttgtat 480
tatataacaa acaaagtaag gaatacagat ttatacaata aattgccata ctagtcacgt 540
gagatatctc atccattccc caactcccaa gaaaaaaaaa aagtgaaaaa aaaaatcaaa 600
cccaaagatc aacctcccca tcatcatcgt catcaaaccc ccagctcaat tcgcaatggt 660
tagcacaaaa acatacacag aaagggcatc agcacacccc tccaaggttg cccaacgttt 720

-continued

| | |
|---|---|
| attccgctta atggagtcca aaaagaccaa cctctgcgcc tcgatcgacg tgaccacaac | 780 |
| cgccgagttc ctttcgctca tcgacaagct cggtccccac atctgtctcg tgaagacgca | 840 |
| catcgatatc atctcagact tcagctacga gggcacgatt gagccgttgc ttgtgcttgc | 900 |
| agagcgccac gggttcttga tattcgagga caggaagttt gctgatatcg gaaacaccgt | 960 |
| gatgttgcag tacacctcgg gggtataccg gatcgcggcg tggagtgaca tcacgaacgc | 1020 |
| gcacggagtg actgggaagg gcgtcgttga agggttgaaa cgcggtgcgg agggggtaga | 1080 |
| aaaggaaagg ggcgtgttga tgttggcgga gttgtcgagt aaaggctcgt tggcgcatgg | 1140 |
| tgaatatacc cgtgagacga tcgagattgc gaagagtgat cgggagttcg tgattgggtt | 1200 |
| catcgcgcag cgggacatgg ggggtagaga agaagggttt gattggatca tcatgacgcc | 1260 |
| tggtgtgggg ttggatgata aaggcgatgc gttgggccag cagtatagga ctgttgatga | 1320 |
| ggtggttctg actggtaccg atgtgattat tgtcgggaga gggttgtttg gaaaaggaag | 1380 |
| agaccctgag gtggagggaa agagatacag ggatgctgga tggaaggcat acttgaagag | 1440 |
| aactggtcag ttagaataaa tattgtaata aataggtcta tatacataca ctaagcttct | 1500 |
| aggacgtcat tgtagtcttc gaagttgtct gctagtttag ttctcatgat ttcgaaaacc | 1560 |
| aataacgcaa tggatgtagc agggatggtg gttagtgcgt tcctgacaaa cccagagtac | 1620 |
| gccgcctcaa accacgtcac attcgccctt tgcttcatcc gcatcacttg cttgaaggta | 1680 |
| tccacgtacg agttgtaata caccttgaag aa | 1712 |